(12) United States Patent
Zotchev et al.

(10) Patent No.: US 8,415,312 B2
(45) Date of Patent: Apr. 9, 2013

(54) COMPOUND WHICH IS A NYSTATIN DERIVATIVE

(75) Inventors: Sergey Borisovich Zotchev, Trondheim (NO); Sven Even Finn Borgos, Trondheim (NO); Trygve Brautaset, Trondheim (NO); Trond Erling Ellingsen, Trondheim (NO); Evgenia Nikolaevna Olsufyeva, Trondheim (NO); Maria Nikolaevna Preobrazhenskaya, Trondheim (NO); Havard Sletta, Trondheim (NO)

(73) Assignee: Biosergen AS, Trondheim (NO)

( * ) Notice: Subject to any disclaimer, the term of this patent is extended or adjusted under 35 U.S.C. 154(b) by 0 days.

(21) Appl. No.: 12/667,434

(22) PCT Filed: Jun. 30, 2008

(86) PCT No.: PCT/GB2008/002238
§ 371 (c)(1),
(2), (4) Date: Jun. 9, 2010

(87) PCT Pub. No.: WO2009/004322
PCT Pub. Date: Jan. 8, 2009

(65) Prior Publication Data
US 2010/0286077 A1  Nov. 11, 2010

(30) Foreign Application Priority Data

Jul. 3, 2007 (GB) .................................... 0712881.2

(51) Int. Cl.
*A61K 31/70* (2006.01)
*C07H 17/08* (2006.01)
(52) U.S. Cl. .......................................... 514/31; 536/6.5
(58) Field of Classification Search ..................... 536/6.5
See application file for complete search history.

(56) References Cited

U.S. PATENT DOCUMENTS

| 3,244,590 A | 4/1966 | Schaffner et al. |
| 3,945,993 A | 3/1976 | Schaffner et al. |
| 4,294,958 A | 10/1981 | Falkowski et al. |

FOREIGN PATENT DOCUMENTS

| DE | 2417993 A1 | 10/1975 | |
| DE | 27 06 156 | 8/1978 | |
| EP | 0 431 874 A1 | 12/1990 | 17/8 |
| GB | 2027698 A | 2/1980 | |
| WO | WO 96/35701 | 11/1996 | |
| WO | WO 01/59126 A2 | 8/2001 | |
| WO | WO 02/097082 | 12/2002 | |
| WO | WO 02/097082 A2 | 12/2002 | |

OTHER PUBLICATIONS

Antibiotiki I Khimioterapiya, 1991, vol. 36(9), pp. 11-13 & Chemical Abstracts, abstr. No. 116:17169; Belakhov et al, "Comparative Study of Fungicidal and Herbicidal Activities of Salts of Polyenic Macrolide Antibiotics", All-Union Res. Technol. Inst. Antibiot. Med. Enzymes, Leningrad, USSR.

Khimiko-Farmatsevticheskii Zhurnal, 1986, vol. 20(6), pp. 739-746 & Chemical Abstracts, abstr. No. 105:19429a & 19432a.

Cybulska et al., "Identification of the structural elements of amphotericin B and other polyene macrolide antibiotics of the heptaene group influencing ionic selectivity of the permeability pathways formed in the red cell membrane", *Biochimica Et Biophysica ACTA*, vol. 1240, 1995, pp. 167-178, XP002513856.

Falkowski et al., "The preparation of methyl esters of trimethylammonium derivatives of polyenes macrolide antibiotics and their biological properties", *ACTA Polonae Pharmaceutica*, vol. 37, 1980, pp. 631-634, XP009111728.

Carmody et al, "Biosynthesis of Amphotericin Derivatives Lacking Exocyclic Carboxyl Groups", The Journal of Biological Chemistry, vol. 280, No. 41, pp. 34420-34426, Oct. 14, 2005.

Brautaset et al, "Biosynthesis of the polyene antifungal antibiotic nystatin in *Streptomyces noursei* ATCC 11455: analysis of the gene cluster and deduction of the biosynthetic pathway", Chemistry & Biology 2000, vol. 7:395-403.

Seco et al, "A Tailoring Activity is Responsible for Generating Polyene Amide Derivatives in *Streptomyces diastaticus* var. 108", Chemistry & Biology, vol. 12, 1093-1101, Oct. 2005.

Szlinder-Richert et al, "MFAME, N-methyl-N-D-Fructosyl Amphotericin B . . . ", Biochimica et Biophysica Acta 1520 (2001) 15-24.

Paquet et al., "Significant Improvement of Antifungal Activity of Polyene Macrolides by Bisalkylation of the Mycosamine", *Organic Letters*, vol. 8, 2006, pp. 1807-1809, XP002503416.

Grzybowska et al., "Preparation of (N,N-dimethylamino) acyl methyl esters and 3-(dimethylamino) propylamides of polyene macrolides as fungicides", *Database Caplus Chemical Abstracts Service*, Sep. 16, 1989, XP002513858.

Grzybowska et al., "Process for preparing L-asparaginates of 3-(N,N-dimethylamino) propylamides of polyene macrolide antibiotics", *Database Caplus Chemical Abstracts Service*, Aug. 10, 1991, XP002503417.

(Continued)

*Primary Examiner* — Elli Peselev
(74) *Attorney, Agent, or Firm* — Nixon & Vanderhye PC

(57) ABSTRACT

The present invention relates to compounds which are nystatin derivatives and are anti-fungal agents.

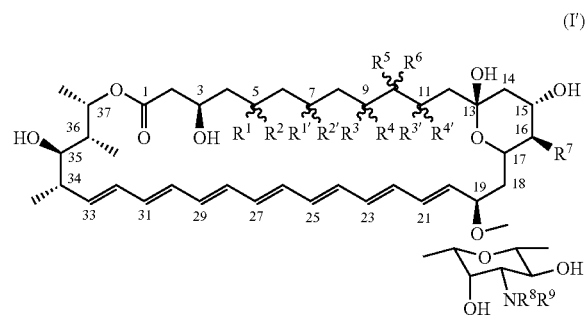

8 Claims, 22 Drawing Sheets

OTHER PUBLICATIONS

Grzybowska et al, Process for preparing L-asparaginates of 3-(N,N-dimethylamino) . . . , Polish patent PL 138831 Nov. 1986; XP-002513857.

Grzybowska et al., "Hydrazides—A Novel Type of Derivatives of Polyene Macrolide Antifungal Antibiotics", *The Journal of Antibiotics*, vol. 43, 1990, pp. 907-908, XP009111791.

GB Search Report in GB 0712881.2 dated Mar. 4, 2008.

International Search Report for PCT/GB2008/002238, mailed Mar. 3, 2009.

Written Opinion for PCT/GB2008/002238, mailed Mar. 3, 2009.

Borgos et al., "Effect of glucose limitation and specific mutations in the module 5 enoyl reductase domains in the nystatin and amphotericin polyketide synthases on polyene macrolide biosynthesis", Arch Microbiol, vol. 185, (2006), pp. 165-171.

1

2

4

5-16

17-23

S44HP standard

Compound 1.

Reference strain

Compound 2

Reference strain

Compound 3

Reference strain

Compound 4

*Figure 13 Scheme 4.*
Synthesis of N-(4-aminomethylbenzoyl) S44HP.
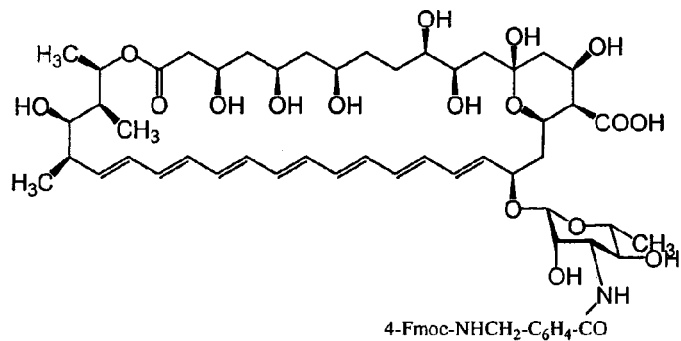
N-(4-Fmoc-aminomethylbenzoyl) S44HP
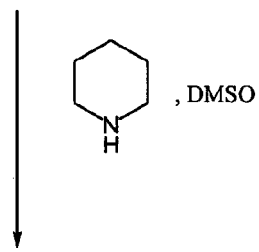, DMSO
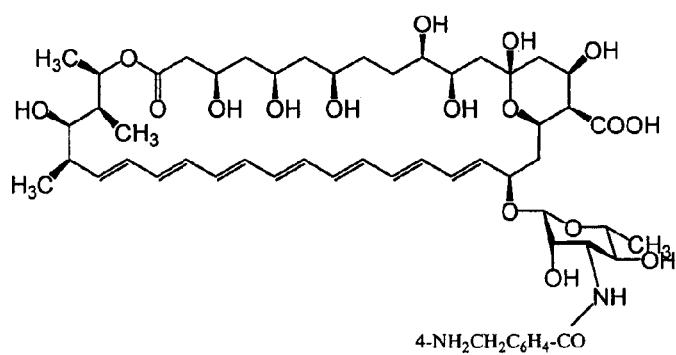
N-(4-aminomethylbenzoyl) S44HP FIG. 14    Scheme 5.  Synthesis of S44HP DMAE amide
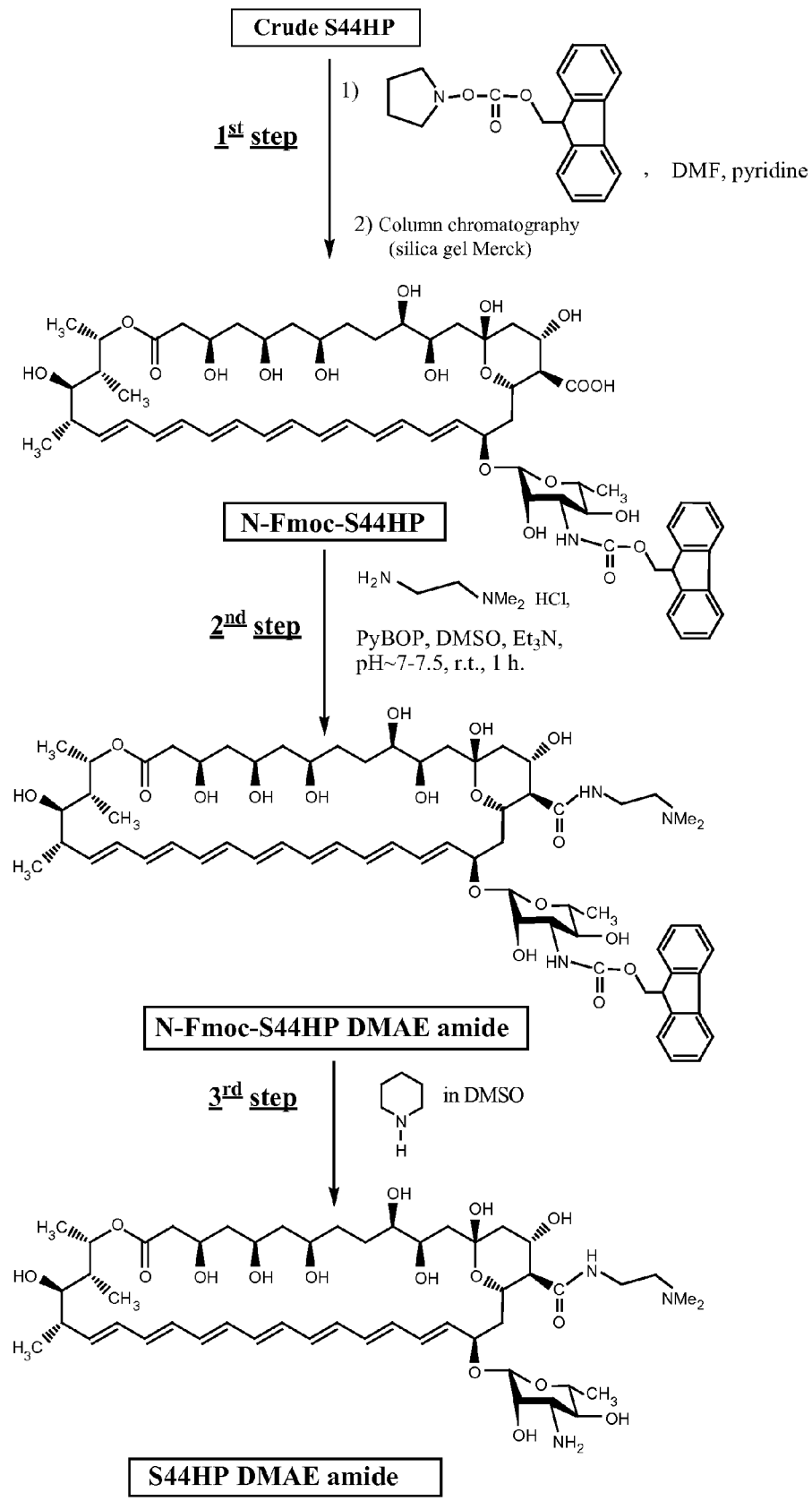

*Scheme 6.* Purification of Compound 1, starting from crude Comp 1.

Scheme 7. N-Fructopyranosyl-Comp 1 (N-alkyl-derivative, Amadori rearrangement); N-(4-N,N-Di-methylaminobenzyl) Comp 1 (N-alkyl-derivative, reductive alkylation); N-L-Lysyl-Comp 1 (N-aminoacyl-derivative, N-Fmoc-aminoacylation); N,N-Di-(3-aminopropyl) Comp 1 (N,N-di-alkyl-derivative, reductive alkylation).

SEQUENCE LISTING

```
<160> NUMBER OF SEQ ID NOS: 26

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ttttgaattc ttcaagccga tgagcc                                          26

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ttttaagctt ggtcgaacag gtccgg                                          26

<210> SEQ ID NO 3
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ctacggtgtc caccagtcga cgggccagaa cctggtgc                             38
```

<210> SEQ ID NO 4
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gcaccaggtt ctggcccgtc gactggtgga caccgtag                          38

<210> SEQ ID NO 5
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tcggctacgg tgtccacgct agcctgggcc agaacctgg                         39

<210> SEQ ID NO 6
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ccaggttctg gcccaggcta gcgtggacac cgtagccga                         39

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ttttctgcag gccgcggtgc gcgc                                         24

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tccggcatgg tccgtgaaac c                                            21

<210> SEQ ID NO 9
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gccccggcca gggcaacttc gaagccggca acacgttcc                         39

<210> SEQ ID NO 10

```
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ggaacgtgtt gccggcttcg aagttgccct ggccggggc                          39

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ttttgaattc ccgacggcct ctcctacc                                      28

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ttttaagctt gccgagtcgg ttgcgc                                        26

<210> SEQ ID NO 13
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ccgggccagg ccaacttcga agccggcaac accttcctcg                         40

<210> SEQ ID NO 14
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
cgaggaaggt gttgccggct tcgaagttgg cctggcccgg                         40

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ttttctgcag ccgaccggca ccgtcc                                        26

<210> SEQ ID NO 16
<211> LENGTH: 25
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 16
ttttaagctt cctggaccgc gcggg                                      25

<210> SEQ ID NO 17
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ccccggccag gccggcttcg aagccgccaa cgcggtcc                        38

<210> SEQ ID NO 18
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ggaccgcgtt ggcggcttcg aagccggcct ggccgggg                        38

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ttcggcggcg taatctcc                                              18

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ttttaagctt ccacggcgag gtgc                                       24

<210> SEQ ID NO 21
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
cccgggccag gccaacttcg aagctgccaa cgccgtcctg                      40

<210> SEQ ID NO 22
<211> LENGTH: 40
<212> TYPE: DNA
<213> ORGANISM: Artificial Sequence
<220> FEATURE:

-continued

```
<223> OTHER INFORMATION: Description of Artificial Sequence: Synthetic
      oligonucleotide

<400> SEQUENCE: 22
caggacggcg ttggcagctt cgaagttggc ctggcccggg                              40

<210> SEQ ID NO 23
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
cacccctggc tcgccgactt cgtcgtcggc ggcatggtc                               39

<210> SEQ ID NO 24
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gaccatgccg ccgacgacga agtcggcgag ccaggggtg                               39

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ccttcctcga actcggcc                                                     18

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gcgtagatct cggtgtcg                                                     18
```

COMPOUND WHICH IS A NYSTATIN DERIVATIVE

This application is the U.S. national phase of International Application No. PCT/GB2008/002238 filed 30 Jun. 2008 which designated the U.S. and claims priority to GB Application No. 0712881.2 filed 3 Jul. 2007, the entire contents of each of which are hereby incorporated by reference.

SEQUENCE LISTING

The instant application contains a Sequence Listing which has been submitted via EFS-Web and is hereby incorporated by reference in its entirety. Said ASCII copy, created on May 11, 2010, is named 613-151.txt and is 6,466 bytes in size.

The present invention relates to new derivatives of nystatin and to processes for the preparation thereof. The invention particularly concerns use of the novel nystatin derivatives in medicine, especially as anti-fungal agents.

Nystatin is a naturally occurring complex of anti-fungal substances produced by certain strains of the gram-positive bacteria *Streptomyces noursei*. The main component of nystatin is nystatin $A_1$ which is a polyene macrolide having the structure shown below:

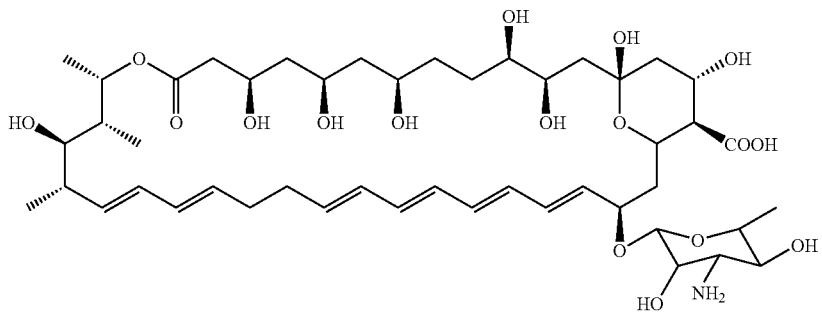 [SMILES: CC1OC(O[C@H]2/C=C/C=C/C=C/C=C/CC/C=C/C=C/[C@H](C)[C@@H](O)[C@@H](C)[C@H](C)OC(=O)C[C@H](O)C[C@H](O)C[C@H](O)CC[C@@H](O)[C@H](O)C[C@]3(O)C[C@H](O)[C@@H](C(=O)O)C(C2)O3)C(O)C(N)C1O]

Nystatin is the active agent present in a number of proprietory preparations (e.g. Infestat, Nyspes, Nystamont, Nystan, Mycostatin and Nilstat) for use in the treatment of candidiasis of the skin and mucous membranes. It is usually administered orally or topically even though it is only poorly absorbed from the gastro-intestinal tract or through skin and membranes. This is because it is toxic when given parenterally.

Nystatin is part of a family of polyene macrolide antibiotics. Other members of the family include pimaricin, rimocidin, candicidin, aureofacin, levorin and amphotericin. Amphotericin is the most commonly used antifungal agent as it is generally considered to be the most effective. It has broad spectrum anti-fungal activity but, like nystatin, it has the major disadvantage of toxicity which limits the administration routes and doses that can be used.

Research efforts on macrolide polyketide antibiotics have therefore focused on amphotericin and, in particular, on the identification of new amphotericin analogues with lower toxicity. Two separate approaches have generally been adopted. In a first approach, researchers have used chemical modifications to try to reduce the toxicity and/or improve anti-fungal activity of amphotericin. Since the total synthesis of amphotericin is not economically feasible, however, the starting material is usually amphotericin B obtained from *Streptomyces nodosus* cultures. As a result, chemical modifications have concentrated on derivatisation of the functional groups present on the amphotericin B ring.

Much more recently, researchers have adopted a different approach that targets the biosynthetic pathway of amphotericin, which is comprised of an assembly line of different enzymes. The carbon chain of amphotericin is assembled from acetate and proprionate units by modular (type 1) polyketide synthases and the resulting macrolide is subsequently modified by other enzymes which cause oxidation, glycosylation and hydroxylation. The genes encoding for the enzymes involved in this biosynthesis have been identified thus researchers have been able to introduce changes to the natural biosynthetic pathway by, for example, removing, adding or modifying a gene and thereby removing, adding or modifying an enzyme involved in the synthesis. The net result is modified amphotericin molecules.

A large number of modified amphotericin molecules have therefore been made and tested, especially chemically modified derivatives. Despite these efforts, however, few promising drug candidates have been identified having an appropriate balance of pharmacological properties, namely high antifungal activity, low toxicity and water solubility. Hence there still remains a need for new antibiotics to treat infectious diseases and in particular acute systemic fungal infections which are increasing in incidence. This requirement is becoming increasingly urgent as resistance to existing anti-fungal agents develops.

Compared to amphotericin, very little research has been carried out on modifying nystatin presumably because it has lower activity than amphotericin, yet suffers from the same disadvantages of toxicity and water insolubility. As a result, it has not been considered an attractive starting molecule for such work.

In a recent study (Organic Letters, 2006, 8 (9), 1807-1809), two derivatives of nystatin were prepared by reductive alkylation of the amino group of mycosamine. The resulting derivatives were found to have higher anti-fungal activity that nystatin, but were less active that the amphotericin B derivatives prepared in the same way. Modification of amphotericin B was therefore considered more promising and the toxicity of these derivatives was tested was shown to be considerably lower compared to the parent molecule.

In WO01/59126 the cloning and sequencing of the gene cluster encoding the polyketide synthase and other enzymes responsible for nystatin synthesis is described. WO01/59126 also goes on to suggest a plethora of potential manipulations that could in theory be carried out on the gene cluster to afford modified nystatin structures. These include modifications to remove or add double bonds from the polyene fragment of nystatin, modifications to remove or reposition the C16 carboxyl group, modifications to add further hydroxyl groups and modifications to truncate the macrolactone ring.

It will be immediately clear from the afore-going that a vast number (approximately $10^{17}$) of different modified nystatin structures could be prepared by carrying out one or more of the modifications suggested in WO01/59126. The possibility of then further modifying any of the compounds produced by genetic manipulation with further chemical modifications means that quintillions of compounds are theoretically possible. Since so little work has been carried out on nystatin, however, no data is available to suggest which of these vast number of compounds might exhibit lower toxicity compared to nystatin and/or amphotericin (i.e. those active agents currently used).

However it has now been surprisingly found that certain derivatives of nystatin have significantly lower toxicity than amphotericin and advantageously, the same derivatives also been found to exhibit useful anti-fungal activity. Unlike the vast majority of modified amphotericin compounds that have been prepared, the nystatin derivatives now been identified are "second generation" derivatives. In other words, these compounds are derivatives of a derivative of nystatin and thus comprise two or more modifications relative to the structure of nystatin $A_1$.

Thus viewed from a first aspect the invention provides a compound which is a nystatin derivative having an additional double bond present between C28 and C29 and which is further modified relative to nystatin at one or more of positions C5, C9, C10, C16 or at the amino group of mycosamine, or a pharmaceutically acceptable salt thereof.

Viewed from another aspect the invention provides a compound which is a nystatin derivative having an additional double bond present between C28 and C29 and which is further modified relative to nystatin at one or more of positions C5, C7, C9, C10, C11, C16 or at the amino group of mycosamine, or a pharmaceutically acceptable salt thereof.

BRIEF DESCRIPTION OF THE DRAWINGS

FIG. 13 shows scheme 4, a scheme for the preparation of N-(4-aminomethylbenzoyl) S44HP.

FIG. 14 shows scheme 5, a scheme for the synthesis of S44HP DMAE amide.

Figure 1A:
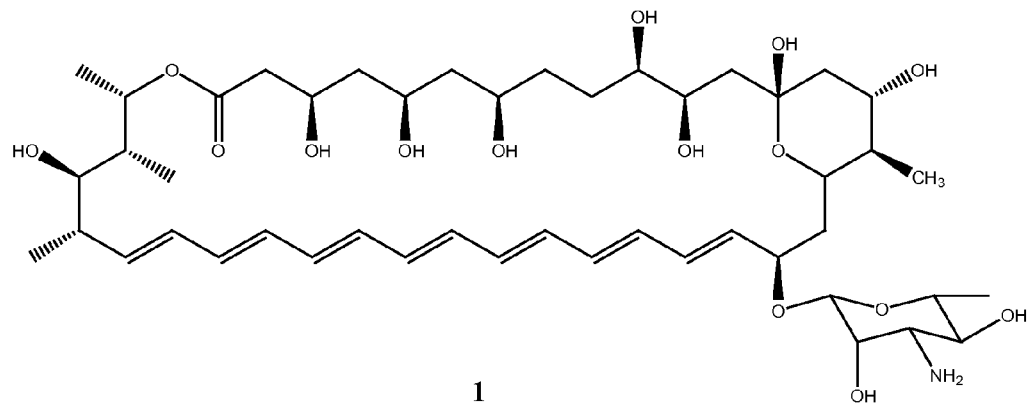
FIG. 1 shows the structure of a number of compounds of the invention.
Figure 1B:
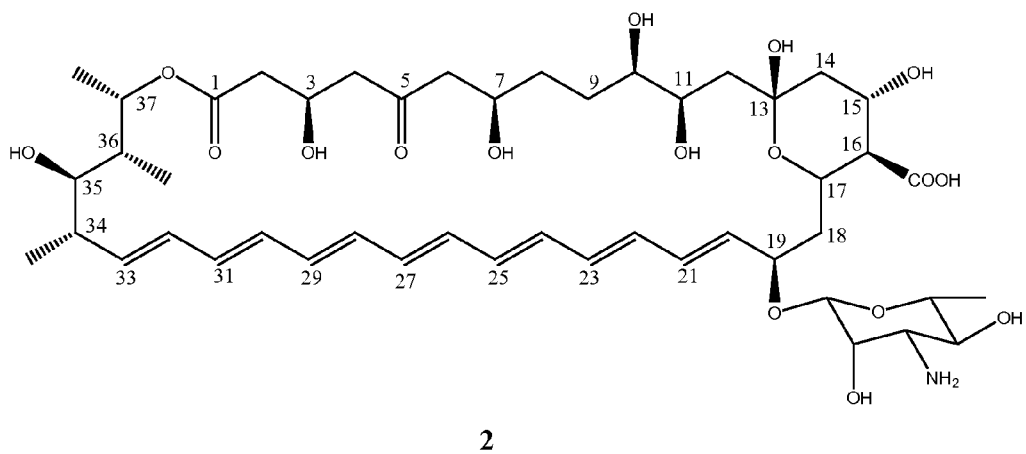
Figure 1C:
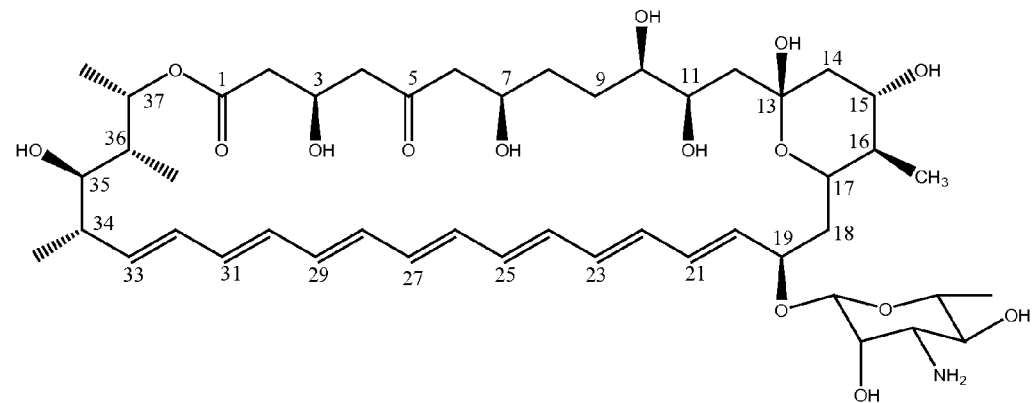
Figure 1D:
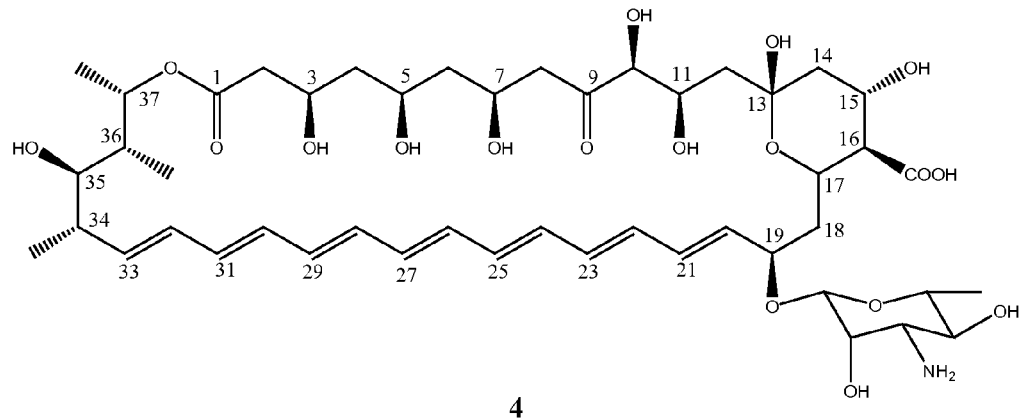
Figure 1E:
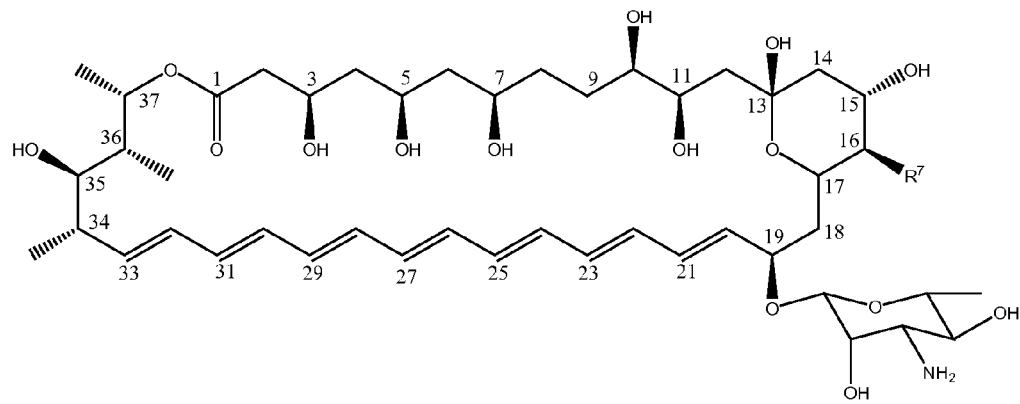
Figure 1F:
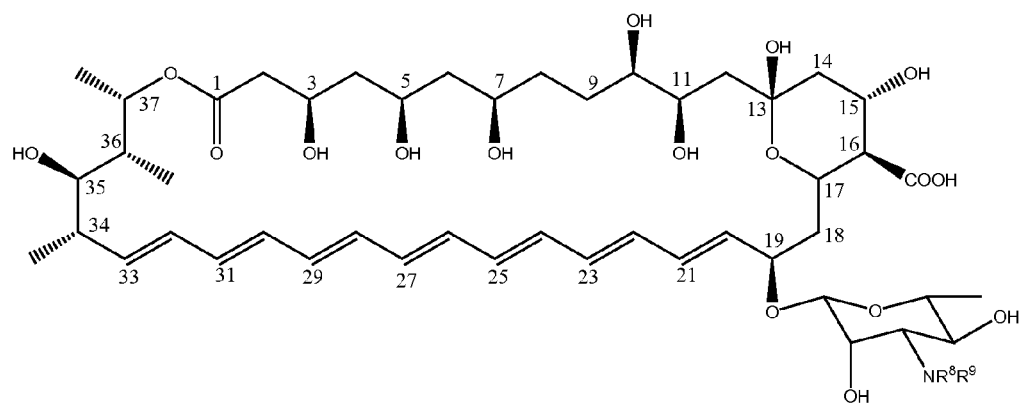

Preferred compounds of the invention are compounds of formula I,

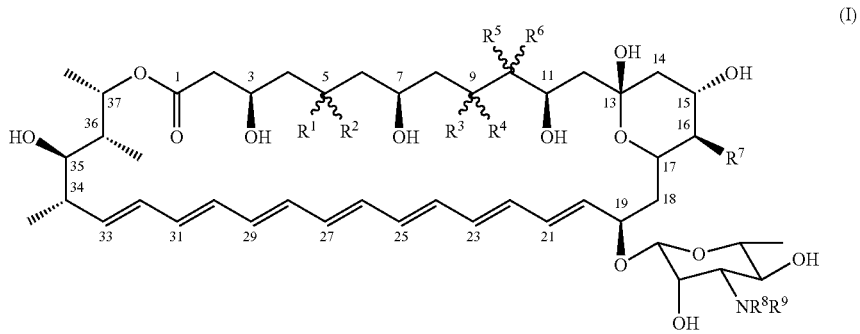

(I)

wherein, $R^1$ and $R^2$ each independently represent a hydrogen atom, a hydroxyl group, an alkoxy group, an acyloxy group or an alkyl group or together form a carbonyl group (e.g. $R^1$ and $R^2$ each independently represent a hydrogen atom or a hydroxyl group or together form a carbonyl group;

$R^3$ and $R^4$ each independently represent a hydrogen atom, a hydroxyl group, an alkoxy group, an acyloxy group or an alkyl group or together form a carbonyl group (e.g. $R^3$ and $R^4$ each independently represent a hydrogen atom or a hydroxyl group or together form a carbonyl group;

$R^5$ and $R^6$ each independently represent a hydrogen atom, a hydroxyl group, an alkoxy group, an acyloxy group or an alkyl group (e.g. a hydrogen atom or a hydroxyl group);

$R^7$ represents a hydrogen atom, COOH, an alkyl group, an alkoxy group, a carboxylic acid ester group or an amide group (e.g. COOH, an alkyl group, a carboxylic acid ester group or an amide group);

$R^8$ and $R^9$ each independently represent a hydrogen atom, an alkylamino group, a sugar group or an acyl group;

or a pharmaceutically acceptable salt thereof, with the proviso that the compound is not compound (II)

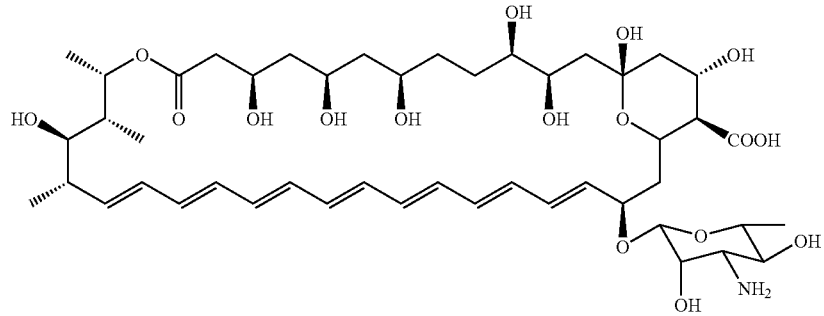

(II)

or the compound mycoheptin (depicted below)

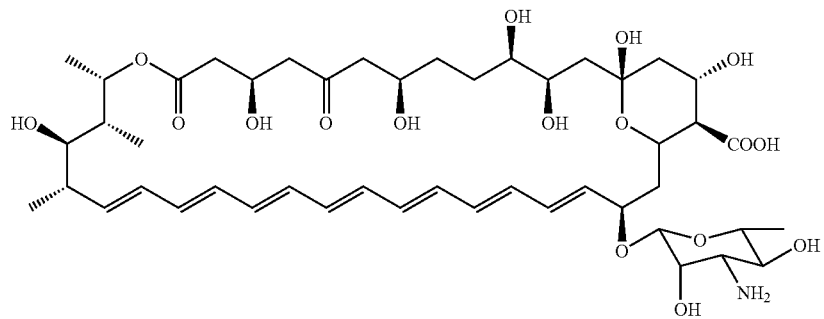 [SMILES: CC1OC(O[C@H]2/C=C/C=C/C=C/C=C/C=C/C=C/C=C/[C@H](C)[C@@H](O)[C@@H](C)[C@H](C)OC(=O)C[C@H](O)CC(=O)C[C@H](O)CC[C@@H](O)[C@H](O)C[C@]3(O)C[C@H](O)[C@@H](C(=O)O)C(C2)O3)C(O)C(N)C1O]

A further preferred compound of the invention, subject also to the provisos above, is of formula (I) but wherein the —OH group at carbon 7 and/or carbon 11 is converted, e.g. to a oxo group. This is formula (I'), i.e.

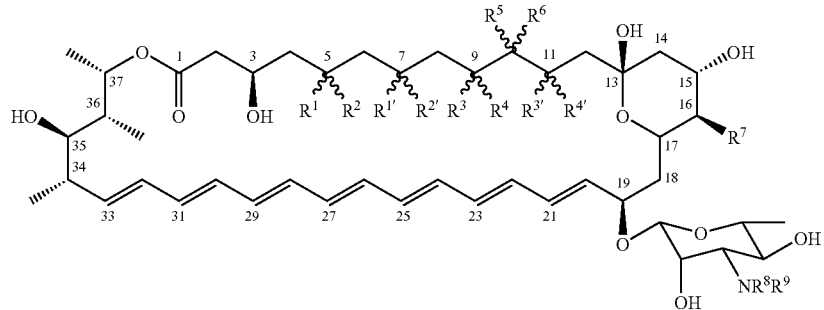

(I')

where all substituents are as defined for formula (I) and $R^{1'}$, $R^{2'}$, $R^{3'}$ and $R^{4'}$ are each independently as defined for $R^1$-$R^4$ respectively and with the additional proviso that the compound of formula (I') is not candidin (depicted below)

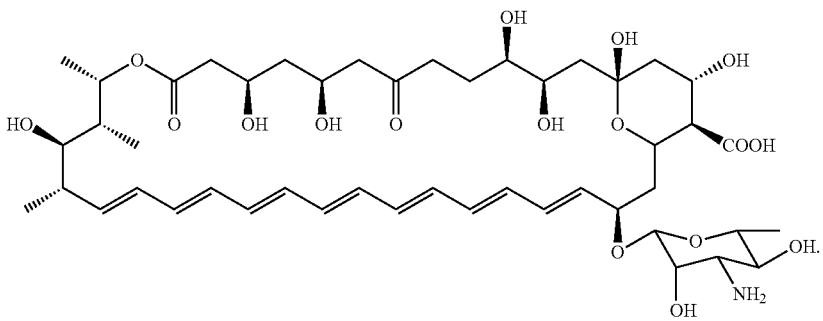 [SMILES: CC1OC(O[C@H]2/C=C/C=C/C=C/C=C/C=C/C=C/C=C/[C@H](C)[C@@H](O)[C@@H](C)[C@H](C)OC(=O)C[C@H](O)C[C@H](O)CC(=O)CC[C@@H](O)[C@H](O)C[C@]3(O)C[C@H](O)[C@@H](C(=O)O)C(C2)O3)C(O)C(N)C1O]

Viewed from a further aspect, the invention provides a process for making compounds as hereinbefore described comprising:

(i) modifying a gene cluster encoding the polyketide synthase system responsible for nystatin synthesis to produce a nystatin derivative having a double bond between C28 and C29; and (ii) additionally modifying said gene cluster to produce nystatin derivative which is further modified at one or more of positions C5, C9, C10, C16 or at the amino group of mycosamine,

OR (iii) modifying the resulting derivative at one or more of positions C5, C9, C10, C16 or at the amino group of mycosamine by a chemical reaction.

Viewed from a further aspect, the invention provides a process for making compounds as hereinbefore described comprising:

(i) modifying a gene cluster encoding the polyketide synthase system responsible for nystatin synthesis to produce a nystatin derivative having a double bond between C28 and C29; and (ii) additionally modifying said gene cluster to produce nystatin derivative which is further modified at one or more of positions C5, C7, C9, C10, C11, C16 or at the amino group of mycosamine,

OR (iii) modifying the resulting derivative at one or more of positions C5, C7, C9, C10, C11, C16 or at the amino group of mycosamine by a chemical reaction.

Viewed from a still further aspect, the invention provides a composition comprising a compound as hereinbefore described and a carrier, diluent or excipient. Preferred compositions are pharmaceutical compositions.

Viewed from a yet further aspect, the invention provides a compound as hereinbefore described for use in therapy.

Use of a compound as hereinbefore described for the manufacture of a composition for treatment of a fungal infections forms a further aspect of the invention.

A method of treatment of a fungal infection in an animal (e.g. human), comprising administering to said animal a compound as hereinbefore defined forms a still further aspect.

As used herein, the term "nystatin derivative" is intended to encompass compounds that have an identical structure to nystatin $A_1$ other than the specific modifications specified. Thus preferred derivatives have the same macrolactone ring as nystatin with the exception of the additional double bond at C28-C29 and have the same functional groups as nystatin with the exception of a modification at one or more of positions C5, C7, C9, C10, C11, C16 or at the amino group of mycosamine. Preferred derivatives therefore comprise the glycosylated macrolactone ring skeleton shown below:

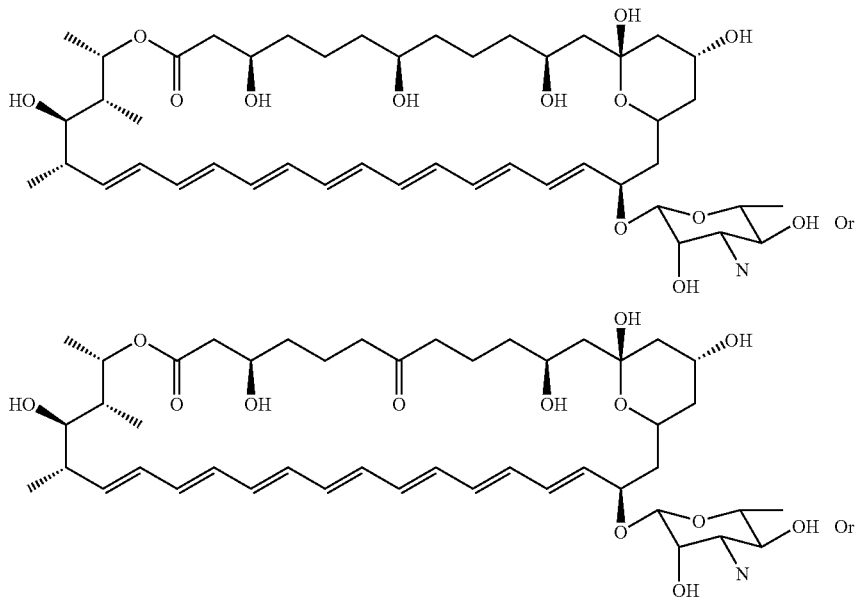

-continued

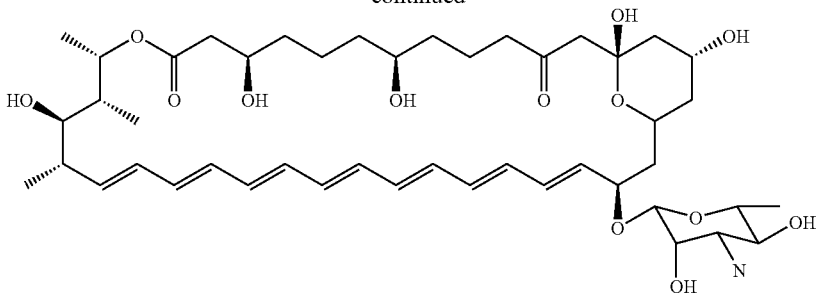

It will be appreciated that in these formulae, there can be modifications at C5, C9, C10, C16 and on the N of the mycosamine. What is shown are therefore only the atoms which must be present. These figures show the chemical skeleton which can be present.

As used herein the term "polyketide synthase system" denotes the collection of enzymes that are responsible for polyketide synthesis and modifications. This includes polyketide synthases, monooxygenases, glycosyltransferase and aminotransferase.

The term "alkyl group" is used herein to represent a cyclic or acyclic, straight-chained or branched, saturated hydrocarbon group. Such groups may contain up to 20 carbon atoms, but groups containing 1 to 12 carbon atoms, more preferably 1 to 6 carbon atoms are preferred.

Alkyl groups may be unsubstituted or substituted. Substituents which may be present in substituted alkyl groups include hydroxy, alkoxy, acyloxy and amino.

Alkyl groups may also be interrupted by one or more groups, e.g. -aryl- (such as Ph), —O—, —NR$^{12}$— or —S—, wherein R$^{12}$ represents a hydrogen atom or a C$_{1-6}$ alkyl group.

The term "alkoxy" is used herein to represent a group —OR$^{13}$, wherein R$^{13}$ is an alkyl group as hereinbefore defined. In preferred alkoxy groups, R$^{13}$ contains 1 to 6 carbon atoms, more preferably 1 to 4 carbon atoms. A preferred alkoxy group is —OC$_{1-6}$, e.g. —OCH$_3$ The term "acyloxy" is used herein to represent a group —OCOR$^{14}$, wherein R$^{14}$ is an alkyl group as hereinbefore defined. In preferred acyloxy groups, R$^{14}$ contains 1 to 6 carbon atoms, more preferably 1 to 4 carbon atoms. A preferred acyloxy group is —OCOC$_{1-6}$, e.g. —OCOCH$_3$.

The term "carboxylic acid ester group" is used herein to represent a group —COOR$^{15}$, wherein R$^{15}$ is an alkyl group as hereinbefore defined. In preferred carboxylic acid ester groups, R$^{15}$ contains 1 to 6 carbon atoms, more preferably 1 to 4 carbon atoms. A preferred carboxylic acid ester group is —COOC$_{1-6}$, e.g. —COOCH$_3$.

The term "amide group" is used herein to represent a group of formula III:

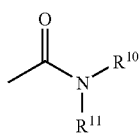

III wherein R$^{10}$ and R$^{11}$ each independently represent a hydrogen atom or an optionally substituted alkyl group as hereinbefore defined or together form an alkyl ring as hereinbefore defined.

The term "alkylamino group" is used herein to represent a group —(CH$_2$)$_x$NR$^{16}$R$^{17}$ wherein x is 1 to 10, preferably 2 to 6 (e.g. 3) and R$^{16}$ and R$^{17}$ each independently represent a hydrogen atom or a C$_{1-6}$ alkyl group.

The term "sugar" is used herein to represent saccharides, especially oligo- and monosaccharides. Sugars present in the compounds of the compounds of invention may comprise any number of saccharide units, but preferred compounds comprise 1 to 10 saccharide units, e.g. 1 or 2 saccharide units.

The term "acyl" is used herein to represent a group —COR$^{18}$ wherein R$^{18}$ is an alkyl group as hereinbefore defined. In preferred acyl groups, R$^{18}$ is a substituted alkyl group, e.g. an amino substituted alkyl group. Particularly preferred acyl groups are amino acyl groups.

As hereinbefore described, the compounds of the present invention are nystatin derivatives having an additional double bond present between C28 and C29 and which are further modified relative to nystatin at one or more of positions C5, C7, C9, C10, C11, C16 or at the amino group of mycosamine.

Preferred compounds of the present invention are modified at C5 relative to nystatin. In nystatin C5 is substituted by a hydroxyl group and a hydrogen atom and is a R stereocentre. Thus in preferred compounds of the invention C5 is substituted by groups other than a hydroxyl group and a hydrogen atom and/or C5 is a S stereocentre. In preferred compounds, different groups are present at C5, e.g. C5 may be substituted by two hydroxyl groups or by two hydrogen atoms. In particularly preferred compounds, C5 is substituted by a carbonyl group.

Other preferred compounds of the invention are modified at C16 relative to nystatin. In nystatin C16 is substituted by a carboxylic acid and a hydrogen atom and is a R steroecentre. Hence in preferred compounds of the invention, C16 is substituted by groups other than a carboxylic acid group and a hydrogen atom and/or C16 is a S stereocentre. In preferred compounds, different groups are present, e.g. an alkyl group (e.g. methyl) and a hydrogen atom or an amide group and a hydrogen atom. In particularly preferred compounds, C16 is substituted by a methyl group and a hydrogen atom. In preferred compounds C16 is a R stereocentre.

Further preferred compounds of the invention are modified at C9 relative to nystatin. In nystatin C9 is substituted by two hydrogen atoms. Hence in preferred compounds of the invention, C9 is substituted by groups other than two hydrogen atoms. In preferred compounds, different groups are present, e.g. a hydroxyl group and a hydrogen atom or a carbonyl group.

Further preferred compounds of the invention can be modified at C7 relative to nystatin. In nystatin C7 is substituted by hydroxyl. Hence in some compounds of the invention, C7 is substituted by groups other than hydroxyl. In preferred compounds a carbonyl group is present. Where a carbonyl is present it will also be necessary for a further modification of the compound at C5, C7, C9, C10, C11, C16 or of the N of the mycosamine relative to nystatin to be present to exclude the compound candidin depicted above.

Further preferred compounds of the invention can be modified at C11 relative to nystatin. In nystatin C11 is substituted by hydroxyl. Hence in some compounds of the invention, C11 is substituted by groups other than hydroxyl. In preferred compounds a carbonyl group is present.

Still further preferred compounds of the invention are modified at C10 relative to nystatin. In nystatin C10 is substituted by a hydroxyl group and a hydrogen atom and is a R stereocentre. Hence in preferred compounds of the invention, C10 is substituted by groups other than a hydroxyl group and a hydrogen atom and/or C10 is a S stereocentre. In preferred compounds, different groups are present, e.g. two hydrogen atoms or a carbonyl group. In particularly preferred compounds, C10 is substituted by two hydrogen atoms.

Yet further preferred compounds of the invention are modified at the amino group of mycosamine relative to nystatin. In nystatin the amino group of mycosamine is unsubstituted, i.e. it is —$NH_2$. Hence in preferred compounds of the invention, amino group of mycosamine is substituted, e.g. by one or more alkylamino or sugar groups.

Where compounds of the invention have a carbonyl at C5 or C7, it is especially preferred if further modifications of the compound at C5, C7, C9, C10, C11, C16 or of the N of the mycosamine relative to nystatin are also present. For example, the amine of the mycosamine could be functionalised to carry at least one substituent $R^8/R^9$ which is other than hydrogen.

Whilst the compounds of the invention can contain only one change relative to known materials such as S44HP, ideally in any compound of the invention, it will comprise two changes at C5, C7, C9, C10, C11, C16 or of the N of the mycosamine relative to nystatin. Preferred compounds can comprise three changes at C5, C7, C9, C10, C11, C16 or of the N of the mycosamine relative to nystatin. Further preferred compounds will comprise at least two changes at C5, C7, C9, C10, C11, C16 or of the N of the mycosamine relative to S44HP. Other preferred compounds will comprise at least two changes at C5, C7, C9, C10, C11, C16 or of the N of the mycosamine relative to mycoheptin. Further preferred compounds will comprise at least two changes at C5, C7, C9, C10, C11, C16 or of the N of the mycosamine relative to candidin.

Especially preferred compounds will comprise at least two changes at C5, C7, C9, C10, C11, C16 or of the N of the mycosamine relative to all of nystatin, S44HP, mycopehptin and candidin.

Particularly preferred compounds of the invention are those of formula (I) or (I') as set out above.

In preferred compounds of formula (I), $R^1$ represents a hydrogen atom, a hydroxyl group, an alkoxy group, an acyloxy group or an alkyl group. Still more preferably, $R^1$ represents a hydrogen atom, a hydroxyl group or an alkoxy group (e.g. a group —$OC_{1-6}$), especially a hydrogen atom or a hydroxyl group (e.g. a hydroxyl group). In preferred compounds $R^2$ is a hydrogen atom. In alternative preferred compounds, $R^1$ and $R^2$ together form a carbonyl group. When C5 is a stereocentre, it preferably is a R centre.

Preferred compounds of formula (I) are also those wherein $R^3$ represents represent a hydrogen atom, a hydroxyl group, an alkoxy group, an acyloxy group or an alkyl group. Still more preferably, $R^3$ represents a hydrogen atom, a hydroxyl group or an alkoxy group (e.g. a group —$OC_{1-6}$), especially a hydrogen atom or a hydroxyl group (e.g. a hydrogen atom). In preferred compounds, $R^4$ is a hydrogen atom. In alternative preferred compounds, $R^3$ and $R^4$ together form a carbonyl group. When C9 is a stereocentre, it preferably is a R centre.

Further preferred compounds of formula (I) are those wherein $R^5$ represents a hydrogen atom, a hydroxyl group, an alkoxy group, an acyloxy group or an alkyl group. Still more preferably $R^5$ represents a hydrogen atom, a hydroxyl group or an alkoxy group (e.g. a group —$OC_{1-6}$), especially a hydrogen atom or a hydroxyl group (e.g. a hydroxyl group). In preferred compounds $R^6$ is a hydrogen atom. When C10 is a stereocentre, it preferably is a R centre.

Still further preferred compounds of formula (I) are those wherein $R^7$ represents COOH, an alkyl group, a carboxylic acid ester group or an amide group. A preferred carboxylic acid ester group is —$COOC_{1-6}$, more preferably —$COOC_{1-4}$, e.g. —$COOCH_3$.

Particularly preferred compounds of formula (I) are those wherein $R^7$ is an alkyl group or an amide group. Preferred alkyl groups are $C_{1-6}$ alkyl, e.g. methyl, ethyl, propyl or butyl, especially methyl.

Preferred amides are those of formula III as hereinbefore defined. Particularly preferred amides are those wherein $R^{10}$ and $R^{11}$ each independently represent a hydrogen atom or a $C_{1-10}$ branched or unbranched $C_{1-10}$ alkyl group optionally substituted by hydroxyl, carboxylic acid ester or amino groups and optionally interrupted by oxygen or nitrogen atoms or $R^{10}$ and $R^{11}$ together form a $C_{1-8}$ cyclic alkyl group, optionally substituted by hydroxy, acyloxy or amino groups and optionally interrupted by oxygen or nitrogen atoms.

In some preferred amides, $R^{10}$ is hydrogen. In further preferred amides $R^{11}$ is a group of formula IV:

$$—(CHR^{18})_y Z \qquad (IV)$$

wherein $R^{18}$ is hydrogen or an alkyl group containing up to 6 carbon atoms (e.g. methyl or $CH(CH_3)_2$);
y is 1 to 6, preferably 2-4, e.g. 3; and
Z is OH, $NR^{19}R^{20}$ or $COOR^{21}$ wherein $R^{18}$, $R^{19}$ and $R^{21}$ are each independently hydrogen or a $C_{1-6}$ alkyl (e.g methyl). In especially preferred amides, $R^{18}$ is hydrogen.

In other preferred amides, $R^{10}$ and $R^{11}$ together form a cyclic alkyl group, preferably a cyclic alkyl group of formula V $$—N\underset{(CH_2)_b}{\overset{(CH_2)_a}{\diagup\!\!\diagdown}}N—(CH_2)_c—Z \qquad V$$

wherein a, b and c each independently represent 1 to 6, preferably 2-4, e.g. 2; and
Z is as hereinbefore defined in relation to formula IV.

Representative examples of particularly preferred amide groups of formula III are those shown below:

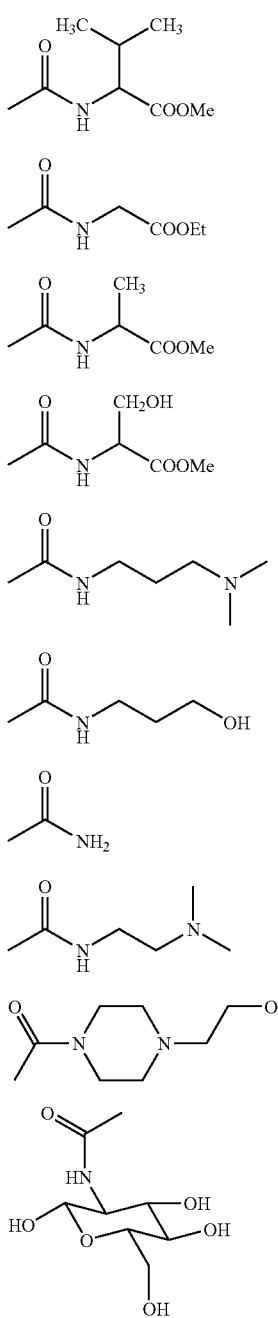

Amide groups 4, 6, 7, 8 and 10 are especially preferred, especially amide group 7 and 10.

Further preferred compounds of formula (I) are those wherein $R^8$ represents a hydrogen atom, an alkylamino group, a sugar group or an acyl group. In preferred compounds $R^9$ is identical to $R^8$ or is a hydrogen atom, e.g. $R^9$ is a hydrogen atom.

Preferred alkylamino groups are those of the formula —$(CH_2)_xNH_2$ wherein x is 2 to 6 (e.g. 3) or alkylated analogues thereof —$(CH_2)_xNC_{1-6}$alkyl$_2$, e.g —$(CH_2)_xNMe_2$. Another preferred group is a lysine residue $COCH[(CH_2)_4NH_2]NH_2$.

Preferred sugar groups comprise 1 to 5 saccharide units, more preferably 2 or 3 saccharide units.

When the sugar group is a monosaccharide, it may be present as a linear, cyclic or mixture of linear and cyclic conformers. When the sugar group comprises more than one saccharide unit, each monosaccharide may be cyclic, linear or a mixture of linear and cyclic conformers. Moreover the saccharide units present may be the same or different.

In compounds of formula (I) preferred monosaccharides are pentoses and hexoses, e.g. glucose, galactose, glucopyranose, mannopyranose, galactopyranose, fructopyranose and tagotopyranose. Preferred di- and oligosaccharides include lactose, melibiose, sucrose, maltose and cellobiose. D-glucose, D-galactose and lactose are especially preferred.

Further preferred acyl groups (for $R^8$) include —$(CH_2)Ph(CH_2)_xNH_2$ or —$(CH_2)Ph(CH_2)_xNMe_2$ where x is 0/1.

Particularly preferred compounds of the invention are those of formula I wherein $R^1$ and $R^2$ together form a carbonyl group. More preferably, when $R^1$ and $R^2$ form a carbonyl group, $R^3$, $R^4$ and $R^6$ are hydrogen atoms and $R^5$ is a hydroxyl group. In such compounds, preferably at least one of $R^8$ and $R^9$ (e.g. both $R^8$ and $R^9$) are hydrogen atoms. Especially preferably C10 is a R stereocentre.

Other particularly preferred compounds of the invention are those of formula I wherein $R^7$ is $C_{1-6}$ alkyl (e.g. methyl). More preferably, when $R^7$ is $C_{1-6}$ alkyl (e.g. methyl), at least one of $R^8$ and $R^9$ (e.g. both $R^8$ and $R^9$) are hydrogen atoms. In such compounds, $R^5$ is preferably a hydroxyl group and $R^6$ a hydrogen atom. Still more preferably $R^3$ and $R^4$ are hydrogen atoms. Especially preferably C10 is a R stereocentre.

Yet further preferred compounds of the invention are those of formula I wherein $R^7$ is an amide group, preferably an amide group of formula III are hereinbefore defined. More preferably, when $R^7$ is an amide group, at least one of $R^8$ and $R^9$ (e.g. both $R^8$ and $R^9$) are hydrogen atoms. In such compounds, $R^5$ is preferably a hydroxyl group and $R^6$ a hydrogen atom. Still more preferably $R^3$ and $R^4$ are hydrogen atoms. Especially preferably C10 is a R stereocentre.

Still further preferred compounds of the invention are those of formula I wherein $R^8$ is a sugar group or an alkylamino group as hereinbefore defined. More preferably, when $R^8$ is a sugar group or an alkylamino group, $R^9$ is a hydrogen atom. In such compounds, $R^7$ is preferably COOH. Still more preferably $R^5$ is a hydroxyl group and $R^6$ is a hydrogen atom and/or $R^3$ and $R^4$ are hydrogen atoms. Especially preferably C10 is a R stereocentre.

For compounds of formula (I'), preferred options are those set out above in connection with formula (I). In addition, in preferred compounds of formula (I'), $R^{1'}$ represents a hydroxyl and $R^{2'}$ is a hydrogen atom or $R^{1'}$ and $R^{2'}$ together form a carbonyl group. When C7 is a stereocentre, it preferably is a R centre.

Preferred compounds of formula (I') are also those wherein $R^{3'}$ represents a hydroxyl group and R4' a hydrogen atom or $R^{3'}$ and $R^{4'}$ represent a carbonyl group. When C11 is a stereocentre, it preferably is a R centre.

Preferably only one of $R^{1'}/R^{2'}$ together or $R^{3'}/R^{4'}$ together represent carbonyl.

Representative examples of preferred compounds of the invention are shown in FIG. 1. Particularly preferred compounds are compound numbers 1, 2, 9, 11, 12, 13, 14, 15, 16, 17, 18, 21 and 22, especially compound numbers 1, 2, 9, 11, 12, 13, 14, 21 and 22, e.g. compound numbers 1 and 11.

Further preferred compounds are those in which the C16 carboxy group is converted to dimethylethylamide. Compounds in which the same carboxy group is converted to a methyl group are also preferred. Especially preferred compounds include those with one of the C16 alterations above as well as changes in the polyol region (C5-C11).

As mentioned above, the compounds of the invention may take the form of pharmaceutically acceptable salts. Such salts include acid addition salts with physiologically acceptable organic or inorganic acids. Examples of suitable acids for the formation of such salts include acetic, aspartic, benzenesulfonic, benzoic, bicarbonic, bisulfuric, bitartaric, butyric, calcium edetate, camsylic, carbonic, chlorobenzoic, citric, edetic, edisylic, estolic, esyl, esylic, formic, fumaric, gluceptic, gluconic, glutamic, glycollylarsanilic, hexamic, hexylresorcinoic, hydrabamic, hydrobromic, hydrochloric, hydroiodic, hydroxynaphthoic, isethionic, lactic, lactobionic, maleic, malic, malonic, mandelic, methanesulfonic, methylnitric, methylsulfuric, mucic, muconic, napsylic, nitric, oxalic, p-nitromethanesulfonic, pamoic, pantothenic, phosphoric, monohydrogen phosphoric, dihydrogen phosphoric, phthalic, polygalactouronic, propionic, salicylic, stearic, succinic, sulfamic, sulfanilic, sulfonic, sulfuric, tannic, tartaric, teoclic and toluenesulfonic. Glutamate salts are especially preferred. Alternatively salts may be formed with bases. Examples of suitable bases for the formation of such salts include primary, secondary, and tertiary amines, substituted amines including naturally occurring substituted amines, cyclic amines, arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine and tripropylamine. The pharmaceutically acceptable salts may be in hydrated form. Procedures for conversion of compounds of formula I into such salts are conventional in the art.

Highly preferred compounds of the invention can be derived from the following skeletons (where the COOH group on position 16 or amino group is functionalised as desired, e.g. where COOH is replaced by R7) Note that in general hydrogen atoms are not drawn on these skeletons. It will be appreciated that these are still present (i.e. to form hydroxyl groups on atoms —O):

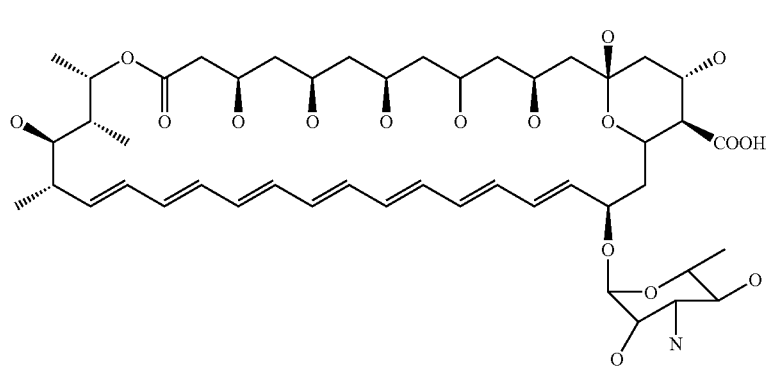

B1

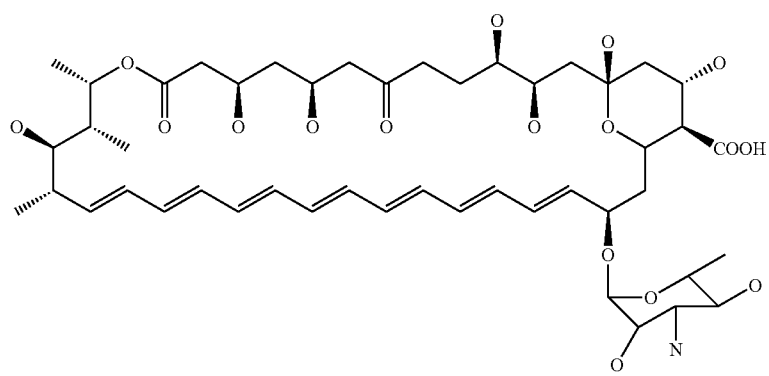

B2

(where the COOH group on position 16 or N group is functionalised)

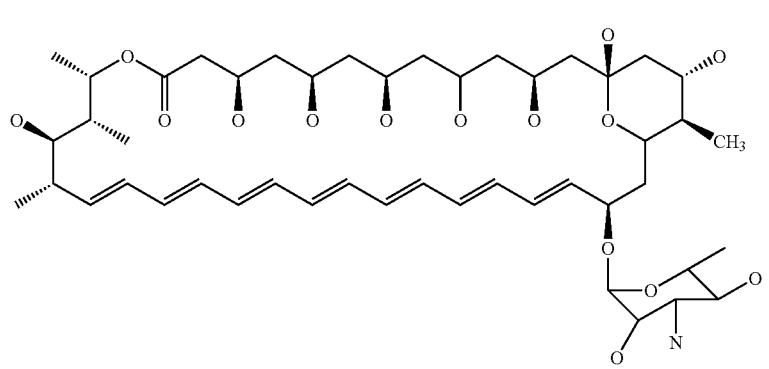

B3

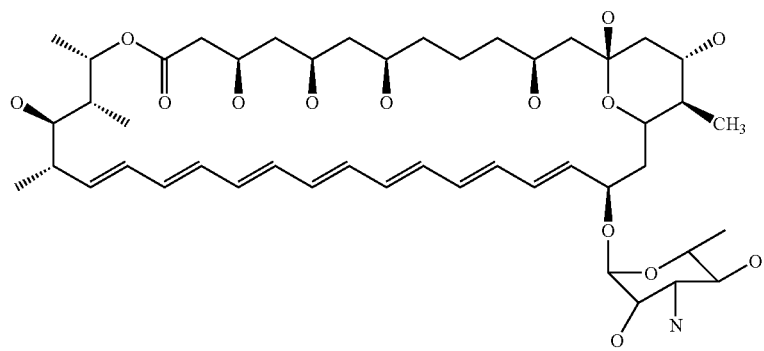
B4
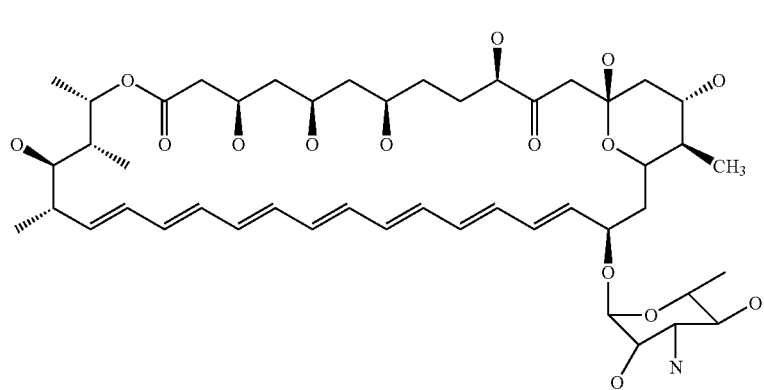
B5
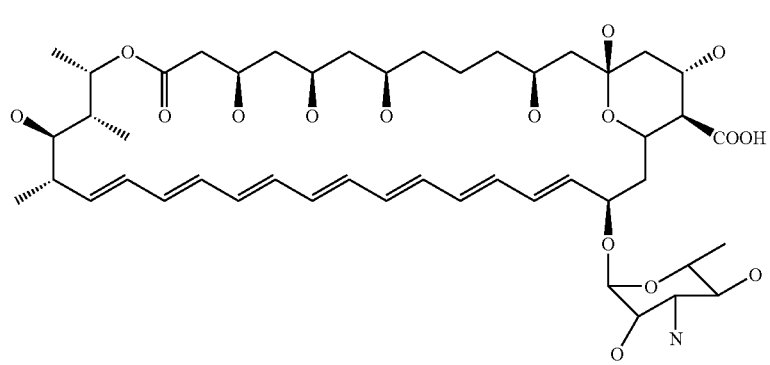
B6
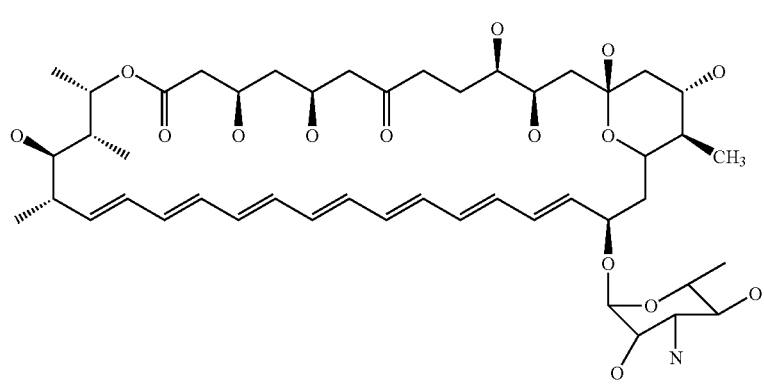
B7

Compound 1 (of the Examples)

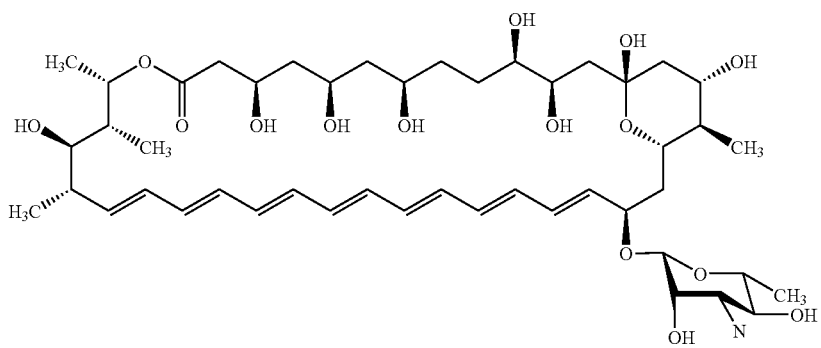

S44HP (where the COOH group on position 16 or N group is functionalised)

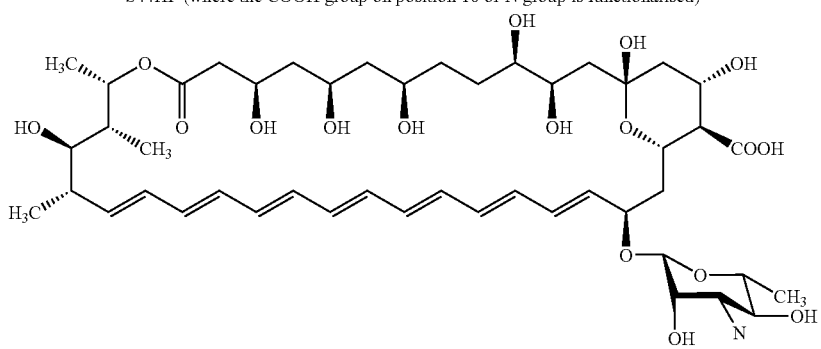

It will be appreciated that there are a number of variables in the compounds of the invention. For the avoidance of doubt it is stressed that each disclosure of the definition of a variable is deemed disclosed in connection with all definitions of other variables in the application. In particular, therefore, preferred options for each variable can be combined with less preferred and preferred options for any other variable.

The compounds of the invention may be prepared using procedures known in the art including conventional synthetic chemistry, genetic manipulation or a combination thereof.

As mentioned above, an aspect of the present invention provides a process for making compounds as hereinbefore described comprising:

(i) modifying a gene cluster encoding the polyketide synthase system responsible for nystatin synthesis to produce a nystatin derivative having a double bond between C28 and C29; and (ii) additionally modifying said gene cluster to produce nystatin derivative which is further modified at one or more of positions C5, C7, C9, C10, C11, C16 or at the amino group of mycosamine,

OR (iii) modifying the resulting derivative at one or more of positions C5, C7, C9, C10, C11, C16 or at the amino group of mycosamine by a chemical reaction.

A preferred process of the invention comprises steps (i) and (ii), i.e. modifying a gene cluster encoding the polyketide synthase system responsible for nystatin synthesis to produce a nystatin derivative having a double bond between C28 and C29 and a further modification relative to nystatin at one or more of positions C5, C7, C9, C10, C11, C16 or at the amino group of mycosamine (e.g. at one or more of positions C5, C9, C10 or C16).

A second preferred process of the invention comprises steps (i) and (iii). Modification of a gene cluster encoding the polyketide synthase system responsible for nystatin synthesis may be carried out according to conventional procedures, e.g. as described in WO01/59126. The nystatin polyketide synthase gene cluster encodes a number of repeated units (modules) each of which is responsible for the one condensation cycle in the synthesis of a polyketide chain. There is a loading module (nysA) which determines the nature of the "starter" unit (carboxylic acid) for initiation of polyketide chain synthesis and 18 "extension" modules which to incorporate (condense onto the chain) further "extender" units (the next carboxylic acids which are added onto the chain). Each such module thus encodes a number of enzymatic activities (e.g. enzymes) which result in the synthesis of the molecule; the module contains domains which separately encode such activities. Thus, a module may typically comprise an acyltransferase (AT) domain, an acyl carrier protein (ACP) domain and a β-ketoacyl synthase (KS) domain for synthesis and extension (ketoreductase (KR), dehydratase (DH) and enoyl reductase (ER) domains which determine the reduced state of the incorporated starter/extender unit. The gene cluster further contain genes (or open reading frames, ORFs) encoding other enzymes (or enzymatic activities) involved in nystatin biosynthesis. Thus, a thioesterase (TE) may permit release of the polyketide from the PKS. Further the genes or gene sequences in the gene cluster may encode enzymes or enzyme activities which may modify the synthesised molecule (polyketide chain) further, for example, by hydroxylation, e.g., monooxygenases (e.g. nysN or nysL) or by glycosylation (e.g. glucuronosyl transferase activity, e.g. nys DI).

Thus, modules and/or domains of the PKS gene cluster may be modified e.g. by insertion, deletion or inactivation or by substitution of a domain or module or by mutation of a domain or module to alter its activity. Thus the number of modules and/or domains may be modified, or they may be altered, to change their activity. Other genes or gene sequences encoding other enzyme activities e.g. monooxygenase or glycosyltransferase may also be modified. Typically, the "reductive" domains (e.g. ER, DH and/or KR) may be modified (e.g. inactivated) in one or more modules, or gene sequences encoding monoxygenase activities (e.g. NysL, NysN) may be modified (e.g. inactivated).

The double bond between C28 and C29 may, for example, be introduced by inactivation of the ER domain in module 5 of polyketide synthase as described in Example 2 of WO01/59126.

Further modifications relative to nystatin at, for example, one or more of positions C5, C9, C10 or C16 may be introduced by other modifications to the gene cluster encoding the polyketide synthase system. When further modifications to the gene cluster are made, they preferably produce a modification relative to nystatin at one or more of positions C5, C9, C10 or C16.

Modification of the nystatin structure at C5 may be brought about by inactivation of the ketoreductase domain in module 17 of the nystatin polyketide synthase, e.g. by the method described in the examples.

Modification of the nystatin structure at C9 may be brought about by inactivation of the ketoreductase domain in module 15 of the nystatin polyketide synthase, e.g. by the method described in the examples.

Modification of the nystatin structure at C10 may be brought about by inactivation of the gene for NysL monooxygenase responsible for C10 hydroxylation, e.g. by the method described in the examples.

Modification of the nystatin structure at C7 may be brought about by inactivation of KR16 domains Modification of the nystatin structure at C11 may be brought about by inactivation of KR14 domains.

Modification of the nystatin structure at C16 may be brought about by inactivation of P540 monooxygenase-encoding genes nysN, e.g. by the method described in the examples.

Further modification of the compounds resulting from step (i), and optionally step (ii), at one or more of positions C5, C7, C9, C10, C11, C16 or at the amino group of mycosamine by chemical reaction may be carried out by any known procedure. Conventional protecting group chemistry may also be employed whenever necessary. When further modifications are introduced by chemical reaction, they preferably produce a modification relative to nystatin at position C16 and/or the amino group of mycosamine.

A preferred chemical reaction is amide formation at C16. Conversion of the nystatin COOH group to an amide may be carried out by reacting the nystatin derivative with the appropriate amine, optionally in the presence of activating agent (e.g. PyBOP).

Another preferred chemical reaction is reductive alkylation at the amino group of mycosamine. Reductive alkylation may be carried out by reacting the nystatin derivative with an appropriate aldehyde to form an imine and reducing the imine, preferably in situ, by addition of a reducing agent. A preferred reducing agent is $NaBH_3CN$.

A further preferred chemical reaction is the Amadori reaction at the amino group of mycosamine. The Amadori reaction may be carried out by reacting the nystatin derivative with an appropriate reducing sugar(s).

A preferred process of the invention affords compounds of formula (I) as hereinbefore described. In such processes, modifications at position C5 modify $R^1$ and/or $R^2$ relative to nystatin, modifications at C9 modify $R^3$ and/or $R^4$ relative to nystatin, modifications at C10 modify $R^5$ and/or $R^6$ relative to nystatin and modifications at C16 modify $R^7$ relative to nystatin. Modifications at the amino group of mycosamine modify $R^8$ and $R^9$ relative to nystatin. Preferred processes are those yielding $R^1$-$R^9$ specified herein as being preferred in relation to the compounds of formula I.

The compounds may be purified by any conventional technique, e.g. crystallisation, chromatography etc. The compounds of Formula I of the invention contain a number of chiral centres and as such exist in a different stereoisomeric forms. Particularly preferred compounds are shown in FIG. 1.

The compounds of the invention may be used in a wide variety of applications to inhibit the growth of, or kill, fungi. For example, the compounds of the invention may be used as disinfectants or as preservatives (e.g. in foodstuffs and cosmetics). Use of the compounds of the invention as a disinfectant or as a preservative forms a further aspect of the invention.

For use as a disinfectant or preservative, the compounds of the invention may be use alone or in combination with other antifungal and/or antibacterial agents. The compounds may be used per se or more preferably in admixture with a carrier, diluent or excipient.

The compounds of the invention are particularly suited to the treatment or prevention of fungal infections. The compounds and pharmaceutical compositions of the invention are especially suited for the treatment or prevention of fungal infections of internal and external areas of the body. Examples of areas of the body that may be treated include the skin, mouth, vagina and gastro-intestinal tract. The compounds and compositions are particularly suited for the treatment of invasive (e.g. systemic) fungal infections.

The compounds of the invention ideally have a broad spectrum of activity but are especially suited to treatment of fungal infections caused by *Candida, Cryptococcus, Aspergillus, Colletotrichum, Geotrichum, Hormonema, Lecythophora, Paecilomyces, Penicillium, Rhodotorula, Fusarium, Saccharomyces, Trichoderma, Trichophyton* and *Scopularilopsis* species, especially *Candida* and *Cryptococcus* species (e.g. *Candida* species).

For use in such treatment, the compounds may be formulated as pharmaceutical compositions in any conventional manner with one or more carrier, excipient and/or diluents. The specific pharmaceutical formulation will depend upon the desired mode of administration and will be readily determined by those skilled in the art. Examples of suitable carriers, excipients and diluents include water, ethanol, glycerol, polyethylene glycol, sodium chloride, sodium deoxycholate, sugars (e.g. glucose, sucrose or lactose), starches (e.g. corn starch or maize starch), microcrystalline cellulose, gums (e.g. gum tragacanth), sorbitol, mannitol, xylitol, magnesium stearate, polyvinylpyrrolidone, fatty acids (e.g. stearic acid), fats, waxes, calcium carbonate, calcium chloride and citric acid.

Such pharmaceutical compositions may additionally comprise one or more wetting agents, sweetening agents (e.g. a sugar, aspartame or saccharin), lubricating agents, stabilising agents, emulsifying agents, suspending agents, preserving agents, flavouring agents (e.g. vanillin, peppermint oil or a fruit flavouring) and/or absorption enhancers.

The compounds of the invention may if desired be co-administered with further (e.g. one, two or three) pharmaceutically active substances. An advantage associated with the use of a combination of the compounds of the invention and further (e.g. one) active substance(s) is that it may increase the spectrum of diseases for which the composition is suitable for use as a medicament. Additionally or alternatively, a lowering of the dose of the compound of the invention and/or the further active substance(s) may advantageously be achieved. This is particularly advantageous when such a further active substance is associated with known side effects.

Additional active substances which may be used in compositions of the invention include other anti-fungal agents and antibiotics. Representative anti-fungal agents are azoles and echinocandins. Representative antibiotics include demeclocycline, triamcinolone acetonide, neomycin sulfate, gramicidin, oxytetracycline and erythromycin.

Pharmaceutical compositions used in accordance with the invention may be administered orally, rectally (e.g. using a suppository), topically or systemically. The route chosen will depend, for example, on the disease and/or the subject to be treated, although compositions for oral and systemic administration are preferred. Compositions for systemic administration are particularly preferred.

The compositions may be presented in any form adapted for use in the administration route selected. Forms suitable for oral administration include, for example, plain or coated tablets, sustained release tablets, chewable tablets, soft capsules, hard capsules, suspensions and syrups. Preferred forms for use according to the invention are tablets, suspensions and syrups, particularly tablets.

Forms suitable for systemic administration may, for example, be formulations for intradermal, intraperitoneal or intravenous injection or infusion. Formulations for intravenous injection are particularly preferred.

Forms adapted for topical administration include compositions for administration to the skin and mucosa (e.g. gels, creams, sprays, lotions, salves and aerosols). The compounds may also be formulated in rectal or vaginal compositions such as suppositories or retention enemas The quantity of the compound of the invention to be used in any application will be readily determined by the skilled man in the art. For example, for use as a disinfectant or preservative, the amount of compound that is required is that which inhibits the growth of, or is lethal to, a target fungi. Whilst the actual amount will depend on a particular target fungi and application, for use as a disinfectant or preservative, the compounds of the invention are typically used in amounts of 0.5 to 5% wt, more preferably 1 to 3% wt of the disinfectant solution or material to be preserved.

For use to treat fungal infections, the quantity of the compound of the invention, as well as any other optional active substance(s) present in admixture therewith, may be readily determined by those skilled in the art and will depend on several factors, including the nature of any optional further active substance(s), the method of administration, the disease to be treated and the weight of the subject. Generally, however, the compounds of the invention may be used in amounts of from 0.01-50 wt % of the composition, preferably 1-20 wt %.

EXAMPLES

Preparation of Compounds

The compounds listed in Table 1 were prepared. The precise stereochemistry of each of these compounds is shown in FIG. 1.

TABLE 1

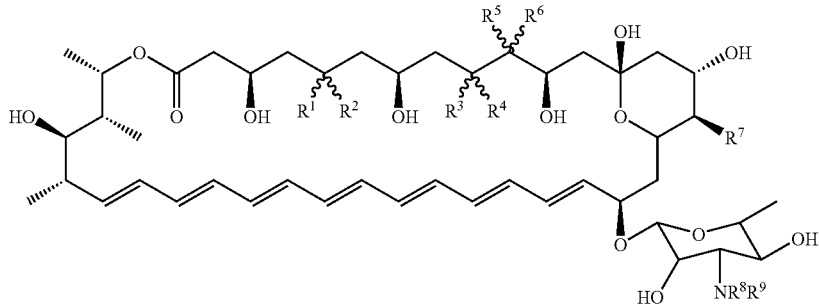

| | $R^1$ | $R^2$ | $R^3$ | $R^4$ | $R^5$ | $R^6$ | $R^7$ | $R^8$ | $R^9$ |
|---|---|---|---|---|---|---|---|---|---|
| S44HP | OH | H | H | H | OH | H | COOH | H | H |
| 1 | OH | H | H | H | OH | H | $CH_3$ | H | H |
| 2 | =O | | H | H | OH | H | COOH | H | H |
| 3 | =O | | H | H | OH | H | $CH_3$ | H | H |
| 4 | OH | H | =O | | OH | H | COOH | H | H |
| 5 | OH | H | H | H | OH | H | $CONHCH_2CH_2OH$ | H | H |
| 6 | OH | H | H | H | OH | H | $CONHCH_3$ | H | H |
| 7 | OH | H | H | H | OH | H | $CONH_2$ | H | H |
| 8 | OH | H | H | H | OH | H | $CONHCH(CH(CH_3)_2)COOCH_3$ (L) | H | H |
| 9 | OH | H | H | H | OH | H | $CONHCH_2COOEt$ | H | H |
| 10 | OH | H | H | H | OH | H | $CONHCH(CH_3)COOCH_3$ (L) | H | H |
| 11 | OH | H | H | H | OH | H | $CONH(CH_2)_3N(CH_3)_2$ | H | H |
| 12 | OH | H | H | H | OH | H | $CONH(CH_2)_3OH$ | H | H |
| 13 | OH | H | H | H | OH | H | $CONHCH(CH_2OH)COOCH_3$ (L) | H | H |
| 14 | OH | H | H | H | OH | H | $CONHCH(CH_2OH)COOCH_3$ (DL) | H | H |
| 15 | OH | H | H | H | OH | H | (piperazine acetyl-ethoxy group) | H | H |

TABLE 1-continued

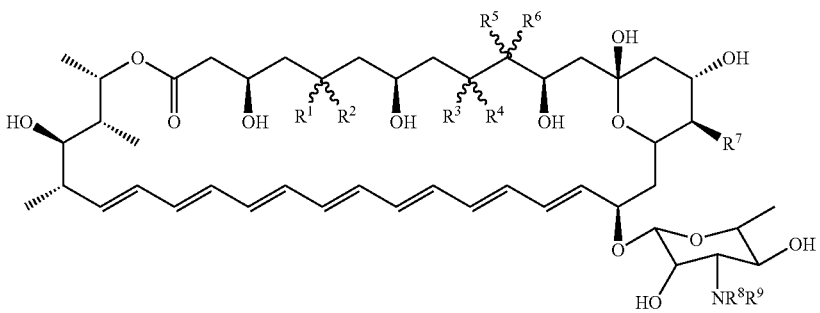

| | R¹ | R² | R³ | R⁴ | R⁵ | R⁶ | R⁷ | R⁸ | R⁹ |
|---|---|---|---|---|---|---|---|---|---|
| 16 | OH | H | H | H | OH | H | (sugar structure) | H | H |
| 17 | OH | H | H | H | OH | H | COOH | (sugar structure) | H |
| 18 | OH | H | H | H | OH | H | COOH | (sugar structure) | H |
| 19 | OH | H | H | H | OH | H | COOH | (disaccharide structure) | H |
| 20 | OH | H | H | H | OH | H | COOH | (aryl structure) | =R⁸ |
| 21 | OH | H | H | H | OH | H | COOH | (CH₂)₃NH₂ | H |
| 22 | OH | H | H | H | OH | H | COOH | (CH₂)₃NH₂ | (CH₂)₃NH₂ |
| 23 | OH | H | H | H | OH | H | COOH | COCH[(CH₂)₄NH₂]NH₂ (L) | H |
| 24 | OH | H | OH | H | H | H | CONH(CH₂)₂N(CH₃)₂ | H | H* |
| 25 | OH | H | H | H | H | H | CH3 | H | H* |
| 26 | OH | H | OH | H | H | H | CH3 | H | H* |
| 27 | OH | H | H | H | H | H | CONH(CH₂)₂N(CH₃)₂ | H | H* |
| 28 | OH | H | H | H | OH | H | CONH(CH₂)₂N(CH₃)₂ | H | H* |
| 29 | OH | H | H | H | OH | H | CH3 | H | H* |

*as glutamate salt

Synthesis of S44HP

This compound was prepared as described in Borgos S. E. et al., *Arch Microbiol.* 2006 April; 185(3):165-71.

Synthesis of Compounds 1-4

Compounds 1-4 were prepared by genetic manipulation using the following combinations of site-specific mutations in the nystatin biosynthetic gene cluster (sequence—in Brautaset, T., et al., *Chem Biol.* 2000 June; 7(6):395-403:
Compound 1 mutations at ER5+NysN;
Compound 2 mutations at ER5+KR17;
Compound 3 mutations at ER5+KR17+NysN;
Compound 4 mutations at ER5+KR15.

The ER5 inactivation vector as described in Borgos S. E. et al., *Arch Microbiol.* 2006 April; 185(3):165-71 was used.

The following constructs were designed and prepared by the applicant:

NysN:
Vectors pSOK201nysN4.1-CL346ST and pSOK201nysN4.1-CL346AS for Introducing Mutations CL346ST and CL346AS, Respectively, in nysN The 4.1 kb NcoI/XbaI fragment of recombinant lambda clone N95 (Brautaset, T., et al., *Chem Biol.* 2000 June; 7(6):395-403) was cloned into the corresponding sites of plasmid pLITMUS28. From the resulting construct the entire 4.1 kb insert was excised with EcoRI/HindIII and cloned into the corresponding sites of pGEM11zf(+). From the resulting plasmid, denoted pGEM11nysN4.1, the 1.5 kb region including the NysN active site was PCR amplified by using the following primers:

```
                                         (SEQ ID NO: 1)
conA-1F: 5'-ttttgaaTTCTTCAAGCCGATGAGCC-3' (sense),
and
                                         (SEQ ID NO: 2)
conA-1R: 5'-ttttaagctTGGTCGAACAGGTCCGG-3'
(antisense).
```

The primers have introduced EcoRI and HindIII sites (underlined), which were used to clone the obtained PCR fragment into corresponding sites of pGEM11zf(+), yielding plasmid pGEM11nysN1.5. The latter plasmid was used as a template for site-directed mutagenesis (using QuickChange kit, Stratagene), by using the following mutagenic oligonucleotides:

```
Mutation CL346ST:
                                         (SEQ ID NO: 3)
CL346ST-F:
5'-CTACGGTGTCCACCAGTCGACGGGCCAGAACCTGGTGC-3'

(SEQ ID NO: 4)
CL346ST-R:
5'-GCACCAGGTTCTGGCCCGTCGACTGGTGGACACCGTAG-3'

Mutation CL346AS:
CL346AS-F:
                                         (SEQ ID NO: 5)
5'-TCGGCTACGGTGTCCACGCTAGCCTGGGCCAGAACCTGG-3'

CL346AS-R: 5'-
                                         (SEQ ID NO: 6)
5'-CCAGGTTCTGGCCCAGGCTAGCGGACACCGTAGCCGA-3'
```

Mutated nucleotides are indicated in bold while new restriction site introduced (SalI for mutation CL346ST; NheI for mutation CL346AS) are underlined in the sequences. Mutations were identified with SalI or NheI restriction analysis and the complete inserts of correctly mutated vectors were verified by DNA sequencing. The mutated 1.3 kb FspAI/Bpu1102I fragments from the resulting plasmids were used to replace the corresponding fragment of plasmid pGM11nysN4.1, yielding plasmid pGM11nysN4.1-CL346ST and pGM11nysN4.1-CL346AS. From the latter constructs, the 4.1 kb inserts containing mutated nysN genes were excised with EcoRI/HindIII and ligated into the 3.1 kb EcoRI/HindIII backbone of pSOK201, yielding the nysN inactivation plasmids pSOK201nysN4.1-CL346ST and pSOK201nysN4.1-CL346AS.

For inactivation of nysN in strain producing compound 1, the construct pSOK201nysN4.1-CL346ST was used. For inactivation of nysN in strain producing compound 3, the construct pSOK201nysN4.1-CL346AS was used.

KR17:
Vector pKR17m for Introducing Mutation YA5145FE in KR17 of NysJ

The 4.0 kb PmlI/BamHI fragment of plasmid pL98E (Brautaset, T., et al., *Chem Biol.* 2000 June; 7(6):395-403) was excised and ligated into the HincII/BamHI sites of vector pGEM3zf(+), yielding plasmid pBB4.0. A 1.5 kb DNA fragment, including
the KR17 active site region, was PCR amplified from pBB4.0 by using the following primers:

```
                                         (SEQ ID NO: 7)
KR17-F: 5'-ttttctgCAGGCCGCGGTGCGCGC-3' (sense),
and
                                         (SEQ ID NO: 8)
KR17-R: 5'-TCCGGCATGGTCCGTGAAACC-3' (antisense)
```

The PCR product was end-digested with PstI (recognition site underlined in the primer) and SacI (recognition site in the amplified DNA fragment), and the 1.4 kb fragment was ligated into the corresponding sites of pLITMUS28. The resulting plasmid, pLIT1.4, was used as a template for site-directed mutagenesis with the following mutagenic oligonucleotides:

```
KR17-mut1:
                                         (SEQ ID NO: 9)
5'-GCCCCGGCCAGGGCAACTTCGAAGCCGGCAACACGTTCC-3'

KR17-mut2:
                                         (SEQ ID NO: 10)
5'-GGAACGTGTTGCCGGCTTCGAAGTTGCCCTGGCCGGGGC-3'.
```

Mutated nucleotides are indicated in bold while new BstBI restriction site introduced is underlined in the sequences. Correct mutation was verified with BstBI digestion and the entire insert of the mutated plasmid was verified by DNA sequencing. From the resulting plasmid, pLIT1.4m, the 1072 bp BclI/AccIII fragment was excised and used to replace the corresponding fragment of plasmid pBB4.0, yielding plasmid pBB4.0m. The entire 4.0 insert of pBB4.0m was excised with EcoRI+HindIII and ligated together with the 3.0 kb EcoRI/HindIII backbone of plasmid pSOK201, yielding the KR17 inactivation vector pKR17m.

KR15:
Vector pKR15m for Introducing Mutation YA1888FE in KR15 of NysJ

The 3.6 kb KpnI/PmlI fragment of pL20X (Brautaset, T., et al., *Chem Biol.* 2000 June; 7(6):395-403) was excised and ligated into the KpnI/HincII sites of pGEM3zf(+), yielding pKP3.6. The latter plasmid was used as a template for the PCR amplification of a 1.1 kb DNA fragment using the following primers:

```
                                              (SEQ ID NO: 11)
KR15-F1: 5'-ttttgaaTTCCCGACGGCCTCTCCTACC-3'
(sense),
and (SEQ ID NO: 12)
KR15-R1: 5'-ttttaagCTTGCCGAGTCGGTTGCGC-3'
(antisense)
```

The resulting PCR product was end-digested with EcoRI/HindIII (restriction sites are underlined in the primers), and ligated into the corresponding sites of pLITMUS28, yielding pLIEH1.1. The latter plasmid served as a template for site-directed mutagenesis using the following mutagenic oligonucleotides:

```
mutKR15-1F: 5'-
                                              (SEQ ID NO: 13)
CCGGGCCAGGCCAACTTCGAAGCGGCAACACCTTCCTCG-3' mutKR15-1R: 5'-
                                              (SEQ ID NO: 14)
CGAGGAAGGTGTTGCCGCTTCGAAGTTGGCCTGGCCCGG-3'
```

Mutated nucleotides are shown in bold and underlined is the new BstBI site introduced. Correct mutation was verified by BstBI digestion and the entire insert of the mutated plasmid was verified by DNA sequencing. From the mutated plasmid the 1045 bp FspAl/AccIII-fragment was excised and used to replace the corresponding region of pKP3.6, yielding pKP3.6mut. The entire 3.6 kb insert of pKP3.6mut was then excised with EcoRI/HindIII and ligated with the 3.2 kb EcoRI/HindIII fragment of pSOK201, yielding the KR15 inactivation vector pKR15m.

Introduction of Replacement Vectors to *S. noursei* Strains:

All inactivations vectors constructed were transformed to *Escherichia coli* ET12567 (pUZ8002) and the resulting recombinant strains were used for conjugation of inactivation vectors into *S. noursei* strains as described previously (Brautaset, T., et al., *Chem Biol.* 2000 June; 7(6):395-403);

- Verification of 1st crossover by Southern Blot+PCR
- Selection of $2^{nd}$ crossover candidates (apramycin-sensitive)
- Genetic characterization of $2^{nd}$ crossover candidates by Southern blot+PCR
- Complementation of correct $2^{nd}$ crossover mutants with pNA0 (Brautaset et al., 2000, Chem. Biol., 7: 395-403).

Complemented recombinant strains were subjected to fermentation and production of corresponding molecules was confirmed via HPLC and MS-TOF analysis.

Compound 1
UV Isoplots

Figure 2A:
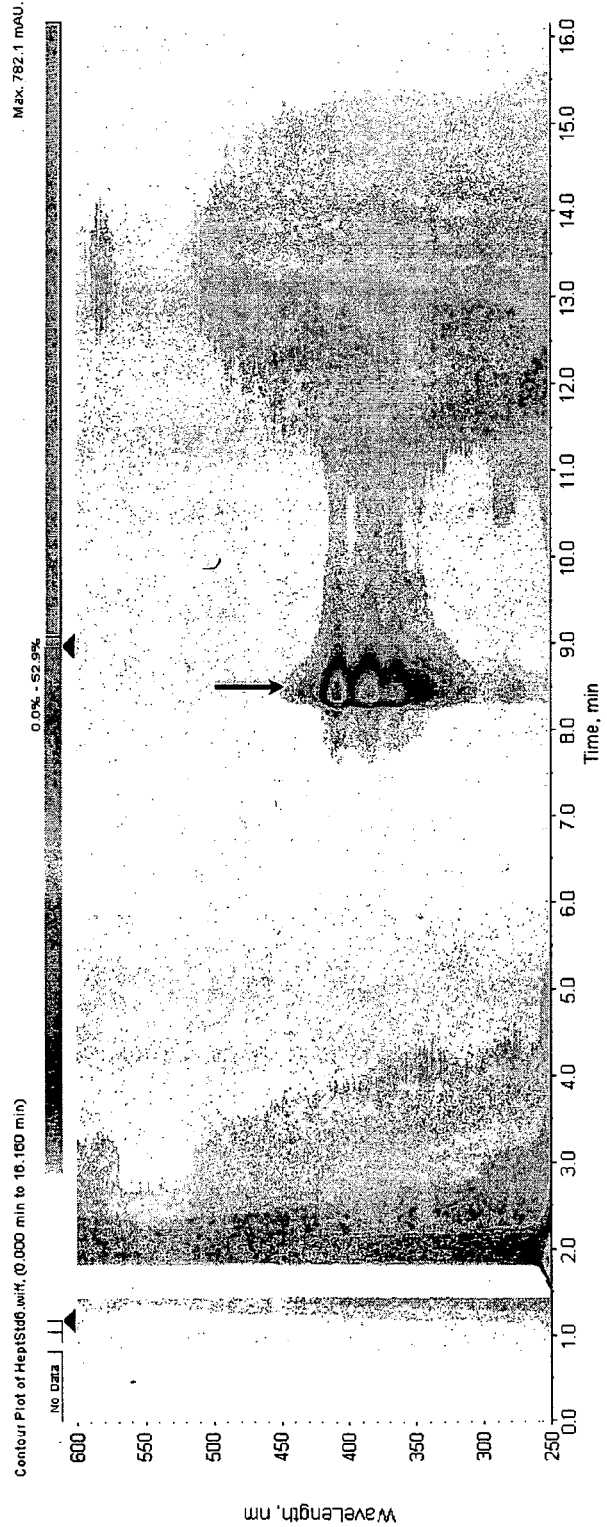
FIG. 2 shows UV-isoplots of S44HP and the DMSO extract from mutant with inactivated ER5 and NysN producing compound 1.
Figure 2B:
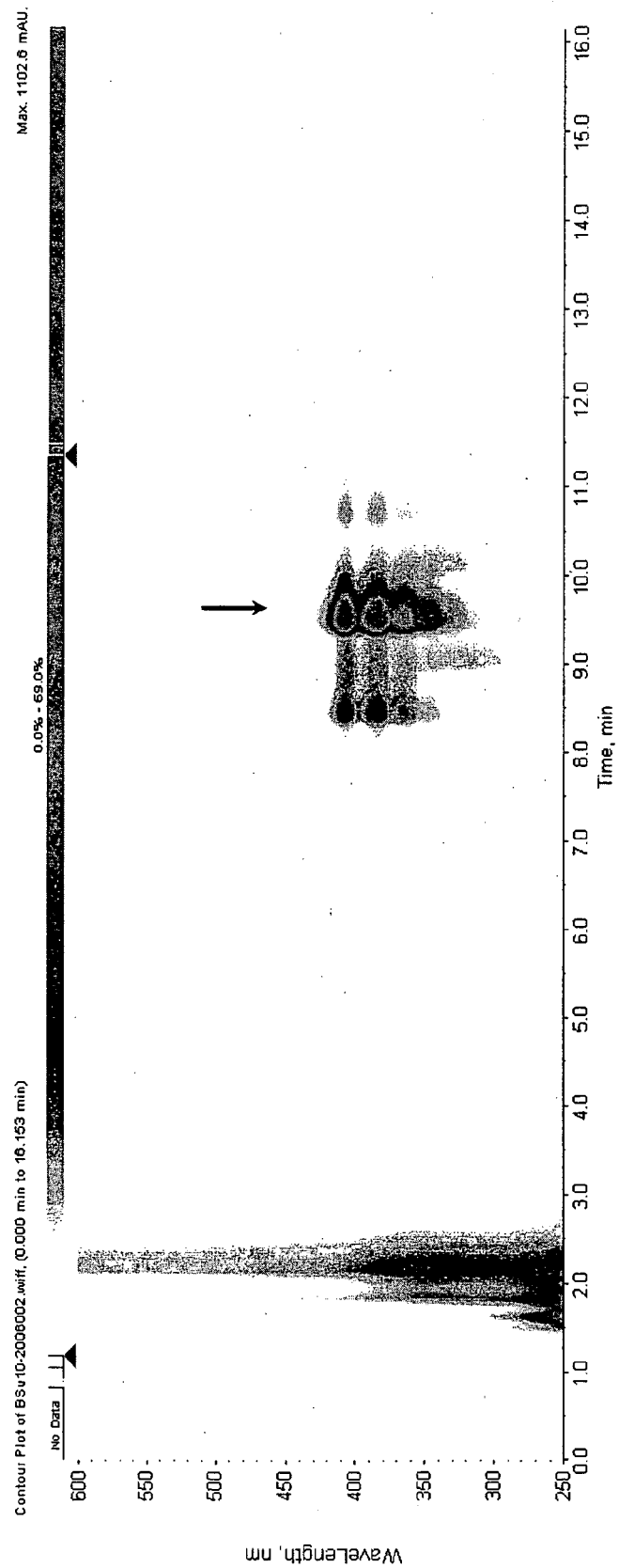

S44HP standard and DMSO extract from *S. noursei* mutant with inactivated ER5 and NysN are shown in the isoplots in FIG. 2.

LC-MS Isoplots:

Column: Zorbax SB-C18 2.1×100 mm, 3.5 µm (Agilent Technologies).

Mobile phase A: 10 mM ammonium acetate (Riedel-de-Haën #25006), pH not adjusted, Mobile phase B: 100% acetonitrile (Rathburn, HPLC grade)

| Time | % B |
|---|---|
| 0.00 | 27 |
| 6.50 | 65 |
| 7.30 | 65 |
| 7.40 | 27 |
| 12.00 | 27 |

Figure 3:
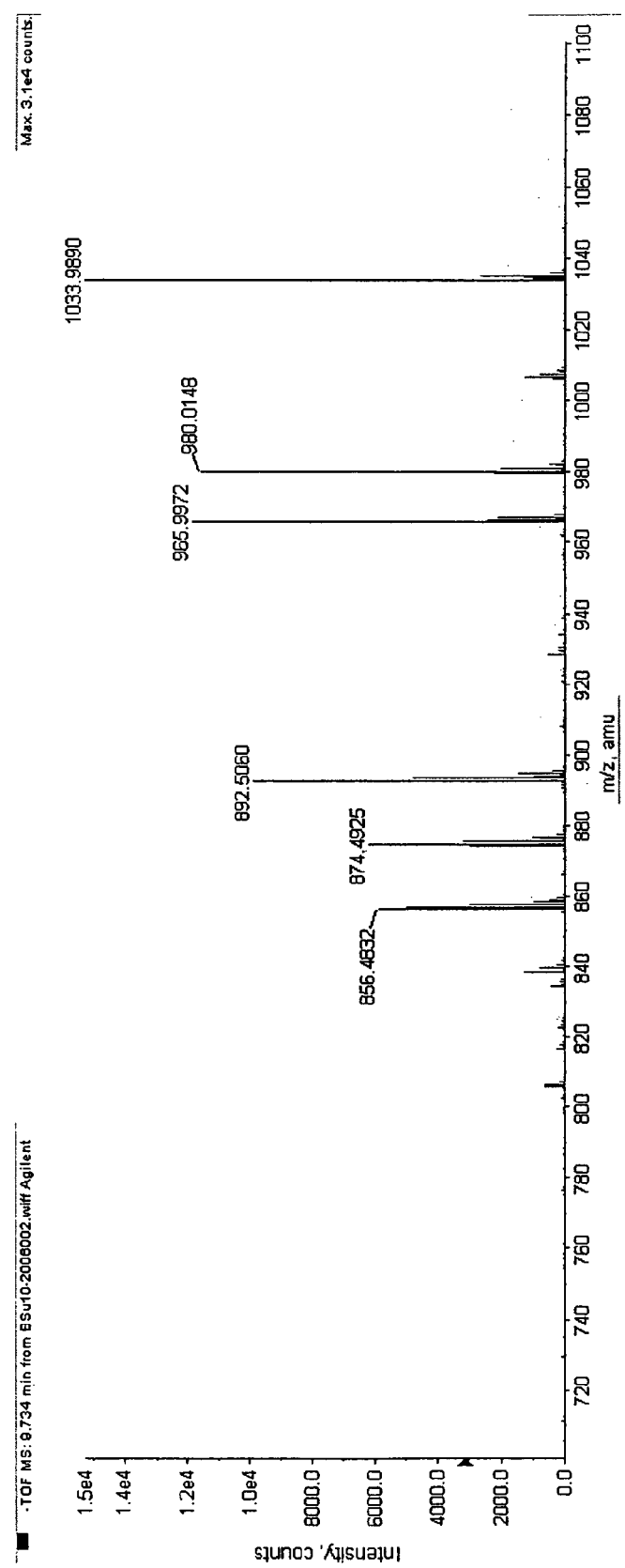
FIG. 3 shows the TOF spectrum of the main polyene peak from the DMSO extract of mutant with inactivated ER5 and NysN. Peaks with m/z=980 and 1034 are internal references.

Flow: 0.22 mL/min
Column temperature: Ambient
TOF-MS Parameters:
Negative API-ES Ionization
    Drying gas: 10 l/min
    Nebulizer pressure: 40 psig
    Drying gas temp.: 350° C.
    Capillary voltage: 3000 V
    Fragmentor: 200 V
TOF-MS Spectrum The TOF-MS spectrum is shown in FIG. 3 wherein peaks of m/z=966, 980 and 1034 are internal mass references. The theoretical m/z (negative ion) of compound 1 ($C_{47}H_{75}NO_{15}$) is 892.5063. This m/z is observed with high accuracy and correlates well with the heptaene UV-peak. Loss of water (1 and 2 molecules) during ionization of compound 1 also yields mass peaks with $\Delta m/z=-18$ and $\Delta m/z=-36$, respectively.

Purification by Preparative LC

Purification was performed on a preparative reverse-phase column.

Preparative Method:

Column: Agilent Prep-C18 50×250 mm, 10 µm (Agilent Technologies).

Mobile phase: 10 mM ammonium acetate (Riedel-de-Haën #25006), pH adjusted to 4.0 with acetic acid (JT Baker #6002), Mobile phase B: 100% methanol (Lab-Scan, HPLC grade)

| Time | % B |
|---|---|
| 0.00 | 78 |
| 6.00 | 78 |
| 6.20 | 100 |
| 11.00 | 100 |
| 11.20 | 78 |

Flow: 85 mL/min
Column temperature: Ambient

After purification by preparative LC, compound 1 was shown to constitute >97% of polyene macrolides in the sample as determined by UV and MS data.

LC-MS Method:

Column: Zorbax Bonus-RP 2.1×50 mm, 3.5 µm (Agilent Technologies).

Mobile phase A: 10 mM ammonium acetate (Riedel-de-Haën #25006), pH adjusted to 4.0 with acetic acid (JT Baker #6002), Mobile phase B: 100% acetonitrile (Rathburn, HPLC grade)

| Time | % B |
|---|---|
| 0.00 | 27 |
| 10.00 | 53 |
| 10.10 | 27 |
| 15.00 | 27 |

Flow: 0.3 mL/min
Column temperature: Ambient
For polyenes without the carboxyl group (notably compound 1), the method was also run with 20 mM ammonium bicarbonate (Fluka #09830) pH adjusted to 7.0 with acetic acid (JT Baker #6002) as mobile phase A, as the elevated pH provided slightly better separation between polyenes with and without the carboxyl ionisable group.

Figure 4A:
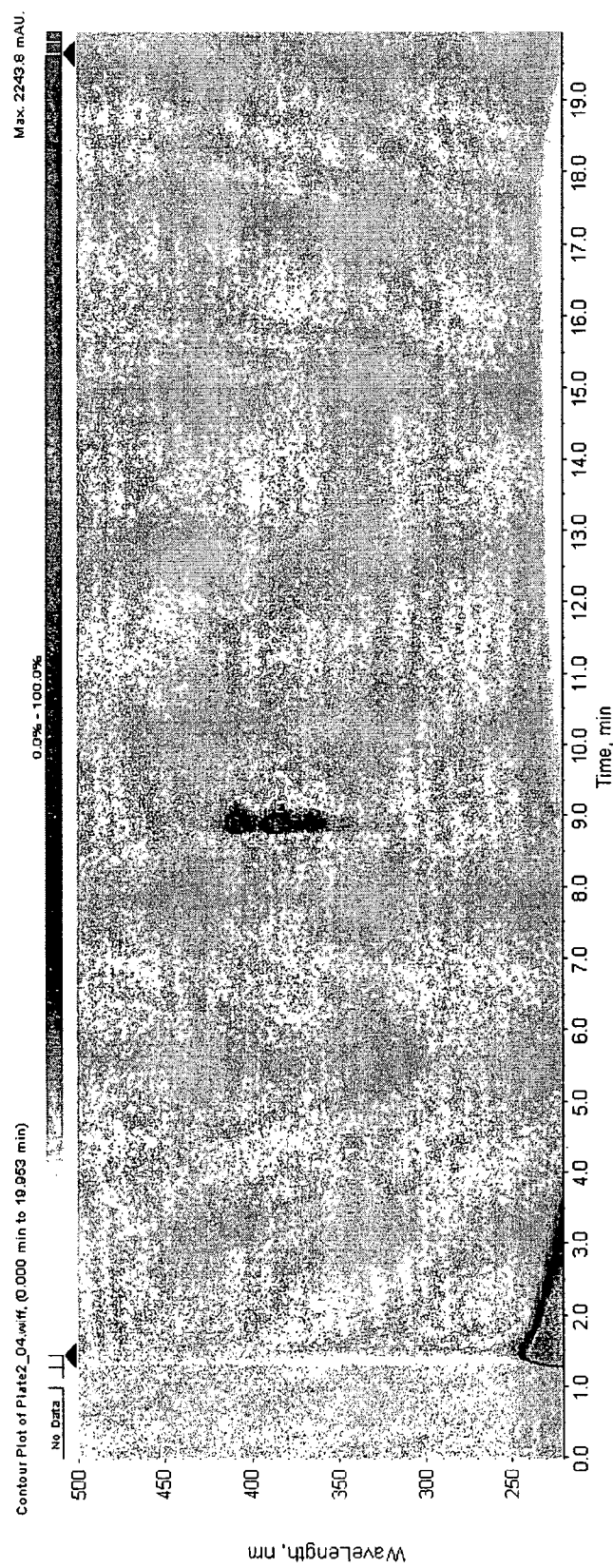
FIG. 4 shows UV-isoplots of DMSO extracts from strain GG5073SP (reference strain) producing S44HP and the mutant with inactivated ER5 and KR17 producing compound 2.
Figure 4B:
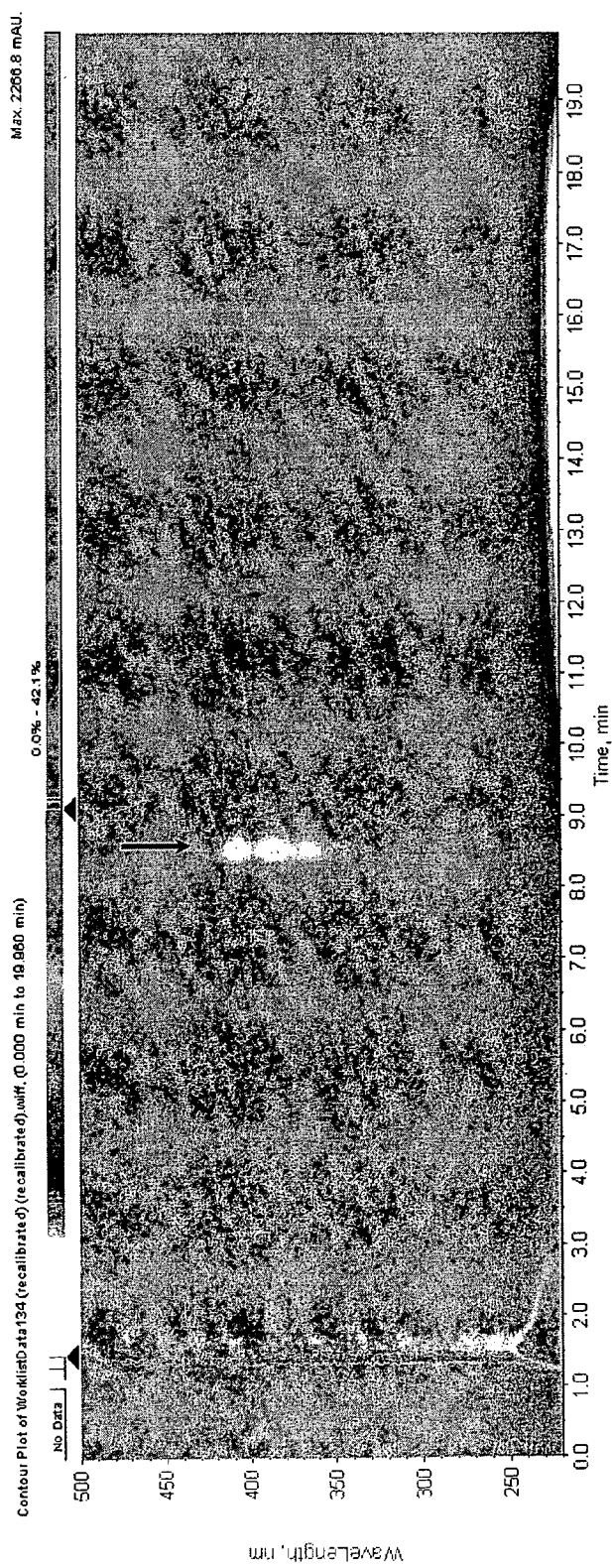

MS Parameters:
Negative API-ES Ionization
  Drying gas: 12 l/min
  Nebulizer pressure: 35 psig
  Drying gas temp.: 350° C.
  Capillary voltage: 3000 V Compound 2
UV Isoplots
DMSO extracts of strain GG5073SP (producing S44HP) and mutant with inactivated ER5 and KR17 domains are shown in the isoplots in FIG. 4.

LC-MS method and TOF-MS parameters: same as for compound 1.

Figure 5:
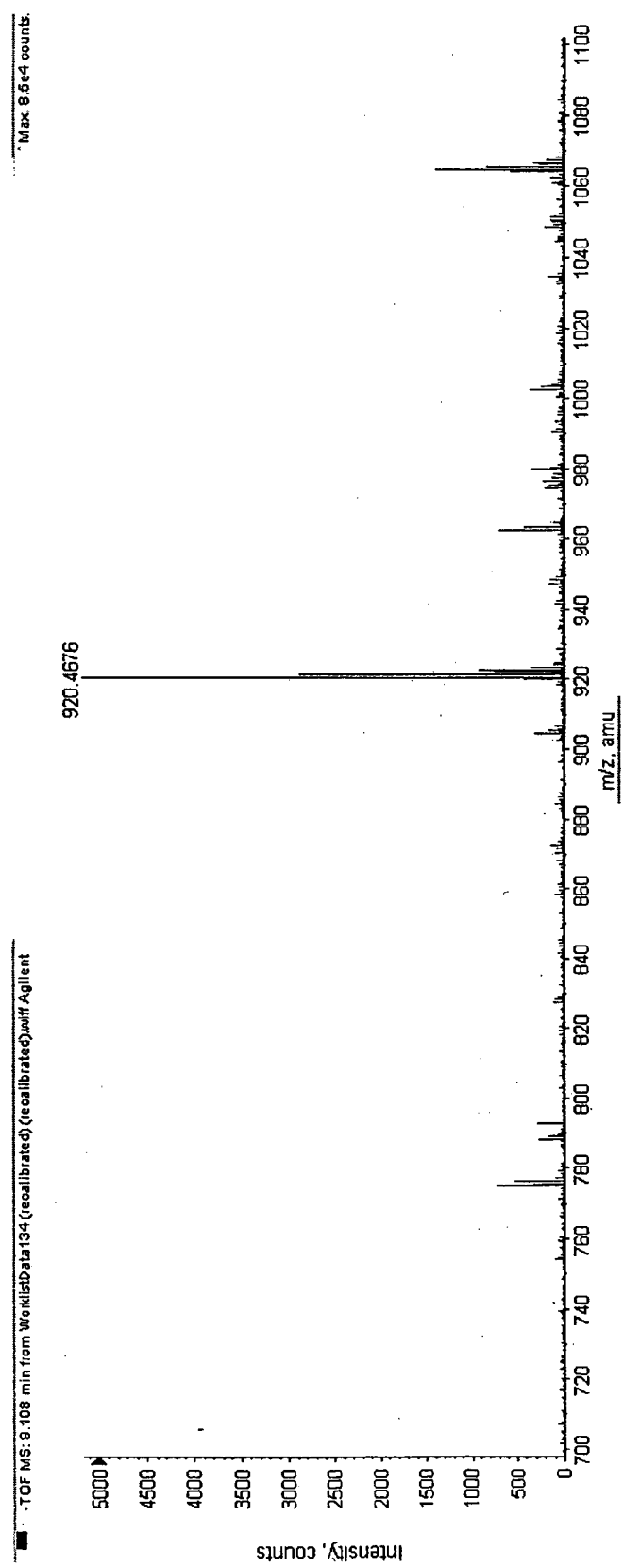
FIG. 5 shows the TOF spectrum of the main polyene peak from the DMSO extract of mutant with inactivated ER5 and KR17.

TOF-MS Data
The TOF-MS spectrum is shown in FIG. 5. The theoretical m/z (negative ion) of compound 2 ($C_{47}H_{71}NO_{17}$) is 920.4649. This m/z is observed with acceptable accuracy (<3 ppm error) and correlates well with the heptaene UV-peak.

Purification by Preparative LC
Purification was performed on a preparative reverse-phase column.

Preparative Method:
Column: Agilent Prep-C18 50×250 mm, 10 μm (Agilent Technologies).
Mobile phase: 10 mM ammonium acetate (Riedel-de-Haën #25006), pH adjusted to 4.0 with acetic acid (JT Baker #6002), Mobile phase B: 100% methanol (Lab-Scan, HPLC grade)

| Time  | % B |
|-------|-----|
| 0.00  | 70  |
| 15.00 | 70  |
| 15.20 | 100 |
| 19.00 | 100 |
| 19.20 | 70  |
| 22.00 | 70  |

Flow: 100 mL/min
Column temperature: Ambient
After purification by preparative LC, compound 2 was shown to constitute >95.2% of polyene macrolides in the sample as determined by UV and MS data.
LC-MS method: same as for compound 1.

Figure 6A:
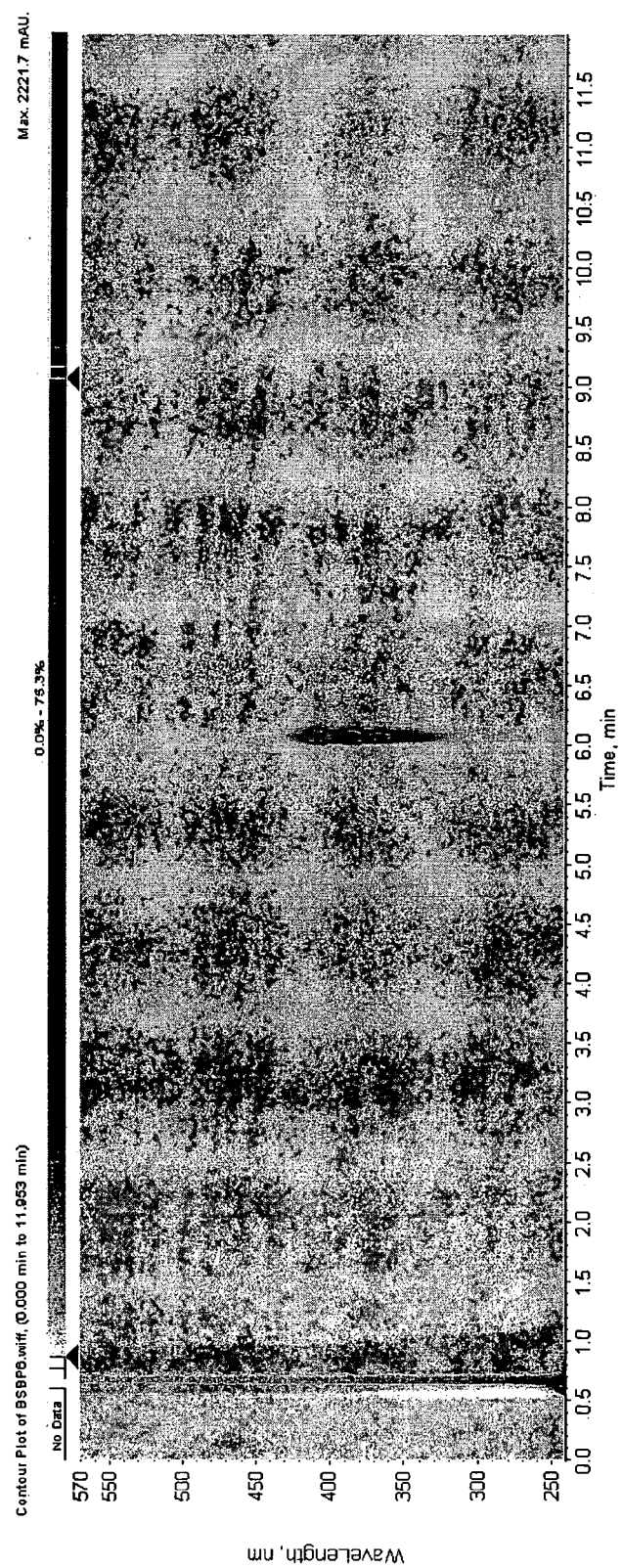
FIG. 6 shows UV-isoplots of DMSO extracts from strain GG5073SP (reference strain) producing S44HP and the mutant with inactivated ER5, KR17 and NysN, producing compound 3.
Figure 6B:
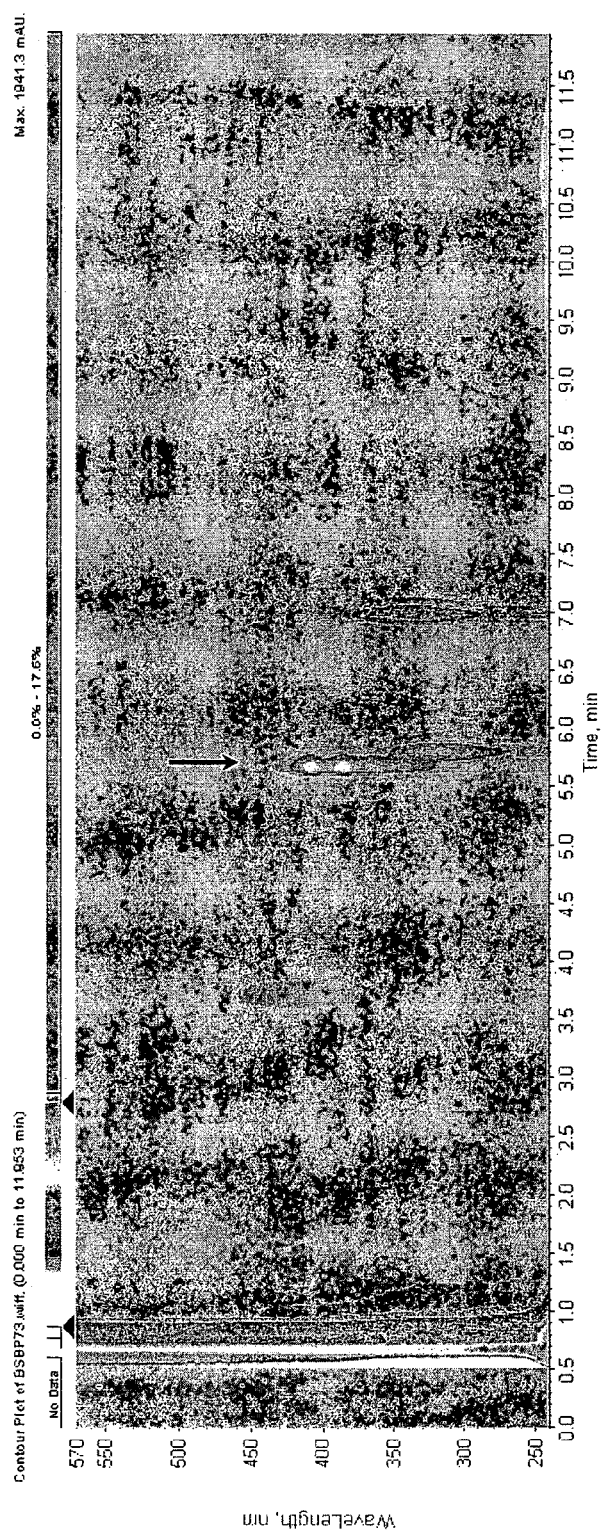

Compound 3
UV Isoplots
DMSO extracts of strain GG5073SP (producing S44HP) and mutant with inactivated ER5 and KR17 domains and inactivated NysN are shown in the isoplots in FIG. 6.

LC-MS Method:
Column: Zorbax Bonus-RP 2.1×50 mm, 3.5 μm (Agilent Technologies).
Mobile phase A: 10 mM ammonium acetate (Riedel-de-Haën #25006), pH adjusted to 4.0 with acetic acid (JT Baker #6002), Mobile phase B: 100% acetonitrile (Rathburn, HPLC grade)

| Time  | % B |
|-------|-----|
| 0.00  | 27  |
| 6.50  | 65  |
| 7.30  | 65  |
| 7.40  | 27  |
| 12.00 | 27  |

Figure 7:
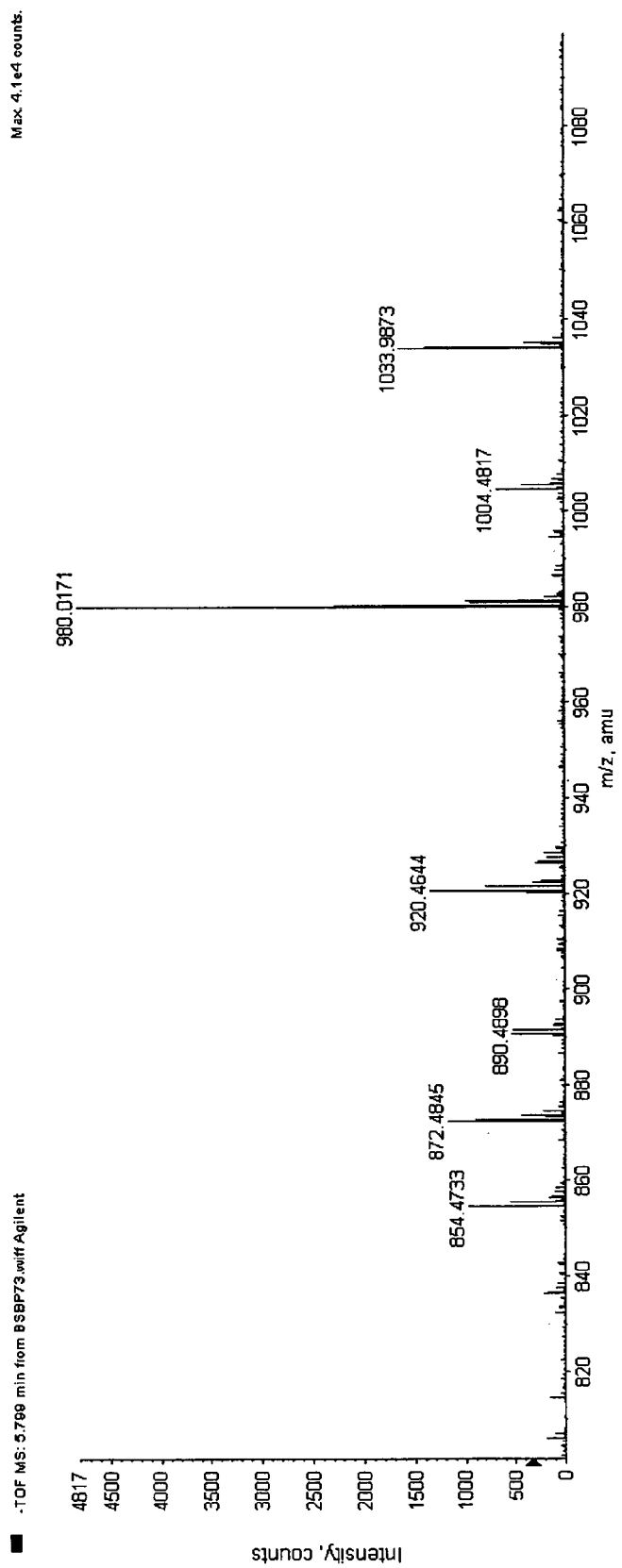
FIG. 7 shows the TOF spectrum of the main polyene peak from the DMSO extract of mutant with inactivated ER5, KR17 and NysN. Peaks with m/z=980 and 1034 are internal references.

Flow: 0.3 mL/min
Column temperature: Ambient
TOF-MS parameters: same as for compound 1
The TOF-MS spectrum is shown in FIG. 7 wherein the peaks of m/z=980 and 1034 are infernal mass references. The theoretical m/z (negative ion) of compound 3 ($C_{47}H_{73}NO_{15}$) is 890.4907. This m/z is observed with high accuracy (see mass spectrum) and correlates well with the heptaene UV-peak. Loss of water (1 and 2 molecules) during ionization of compound 3 also yields mass peaks with $\Delta m/z=-18$ and $\Delta m/z=-36$, respectively. Also, the carboxylated analogue (with m/z=920.4644 in the MS spectrum shown) shows a significant degree of chromatographic co-elution. It is known that the carboxylated compounds have markedly higher ionization efficiency in the negative MS mode, so relative quantification should not be based on the signal intensities in the MS spectrum shown.

Figure 8A:
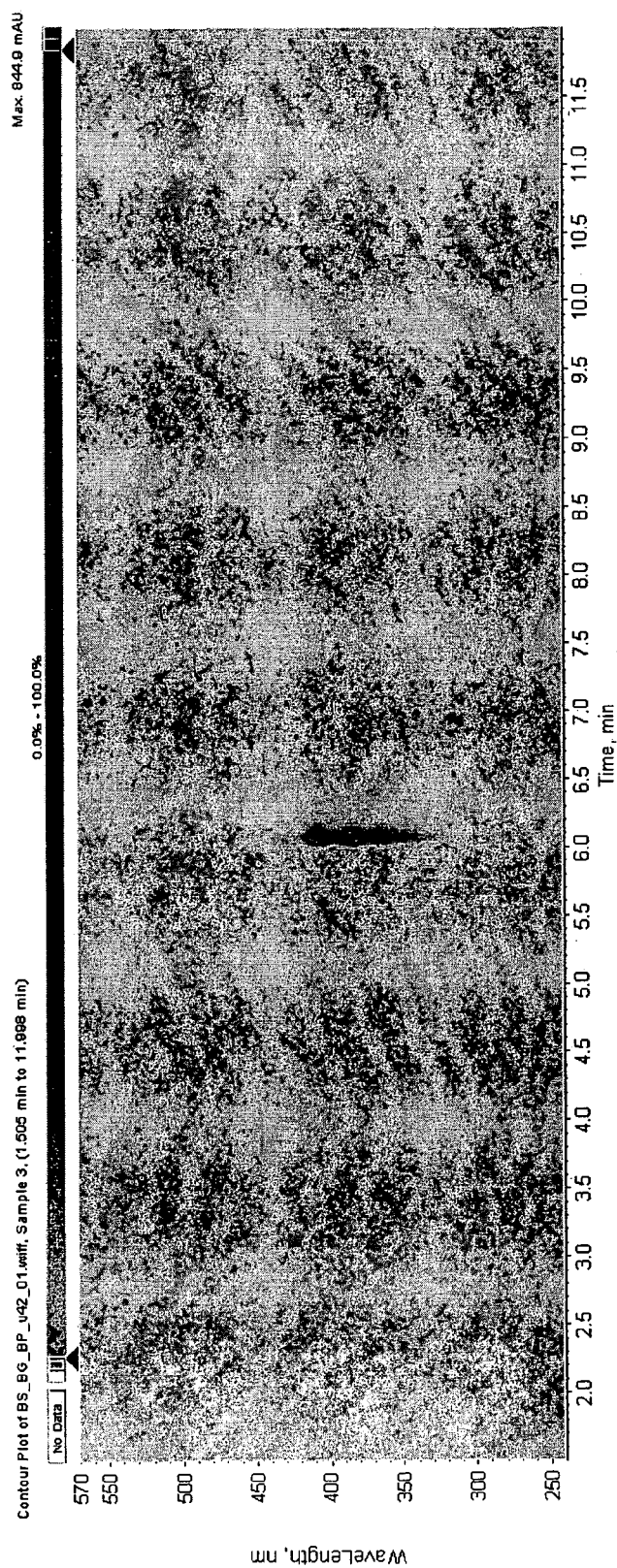
FIG. 8 shows UV-isoplots of DMSO extracts from strain GG5073SP (reference strain) producing S44HP and the mutant with inactivated ER5 and KR15 producing compound 4.
Figure 8B:
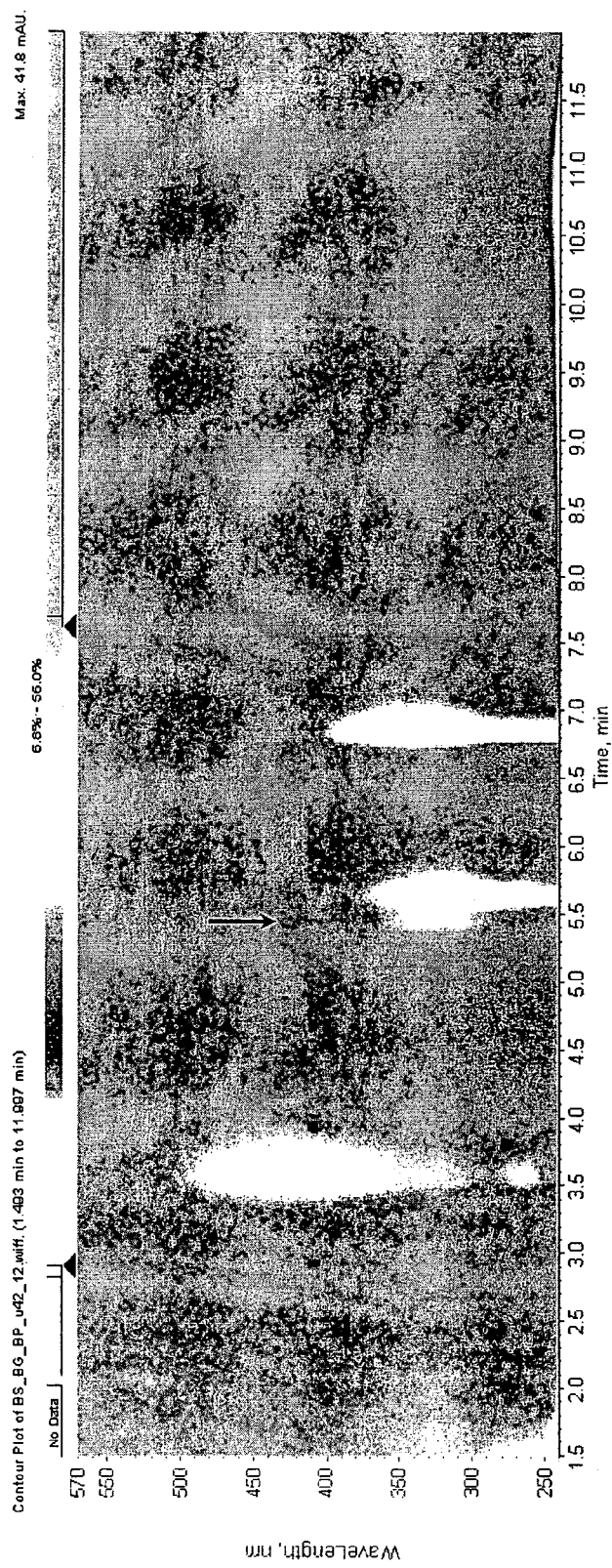

Compound 4
UV Isoplots
DMSO extracts of strain GG5073SP (producing S44HP) and mutant with inactivated ER5 and KR15 domains are shown in the isoplots in FIG. 8.
LC-MS method: same as for compound 3.

Synthesis of Compounds 5-23
General
The reactions were monitored by TLC on Merck Silica Gel 60F254 plates in a solvent system of $CHCl_3$:MeOH:$H_2O$:HCOOH. (13:6:1:0.1). The purity of the resulting products was determined by HPLC and was 80-90%. Analytical reverse phase HPLC was carried out on a Shimadzu HPLC instrument of the LC 10 series on a Kromasil 100-C18 column (4×250 mm, particle size 6 μm) at an injection volume of 20 μL and a wavelength 408 nm. The solvent system comprised 0.01M $H_3PO_4$ at pH 2.6 and acetonitrile. The proportion of acetonitrile varied from 30 to 70% for 30 min with flow rate 1.0 mL/min.

Synthesis of Compounds 5-16
To a mixture of S44HP (18 mg, 0.02 mmol) and 0.06 mmol of the appropriate amine hydrochloride dissolved in 0.3 mL of DMSO was added, portion-wise, $Et_3N$ to adjust pH 8-8.5 and afterwards during 15 minutes 0.03 mmol of PyBOP-reagent. The reaction mixture was stirred at room temperature for 1 hour. Subsequent addition of diethyl ether (~3 mL) to the reaction mixture led to an oily residue, which was shaken successively with diethyl ether (3 mL×2). After addition of 5 mL of acetone to this oil, a yellow precipitate of amide was formed. The precipitate was filtrated, washed with acetone and then dried in vacuo. All samples were obtained in the yields of more than 90%. The analytical data for these compounds is summarised in Table 2 below.

Synthesis of Compounds 17-19
Appropriate monosaccharide (D-glucose or D-galactose) or disaccharide (lactose) (0.086 mmol) was added to a solution of S44HP (40 mg, 0.043 mmol) in DMF (2 mL). The reaction mixture was kept at 37° C. for 20 hours and then the solution was added dropwise to diethyl ether (50 mL). The resulting precipitate was filtered off, washed with diethyl ether and dried. The obtained yellow precipitate was purified by flash chromatography ($CHCl_3$:MeOH:$H_2O$:HCOOH (13:6:1:0.1)). Fractions containing the desired compound were collected and the solution was concentrated. The addition of diethyl ether then gave yellow precipitate which was filtered off, washed with diethyl ether and dried in vacuo. All samples were obtained in yields of 40-45%. The analytical data for these compounds is summarised in Table 2 below.

Synthesis of Compound 20

To a solution of 4-N,N-dimethylaminobenzaldehyde (0.065 mmol) and S44HP (20 mg, 0.022 mmol) in DMF (2 mL) was added NaBH$_3$CN (4.1 mg, 0.065 mmol). The reaction mixture was kept at 37° C. for 20 h. Addition of diethyl ether (10 mL) led to an oily residue, which was shaken successively with diethyl ether (10 mL×2). Yellow precipitate was formed after addition of acetone (10 mL). The precipitate was filtered off, washed with diethyl ester and dried. The obtained solid was purified by flash chromatography (CHCl$_3$:MeOH:H$_2$O:HCOOH (13:6:1:0.1)) on Merck Silica Gel for column chromatography (0.040-0.063 mm). Fractions containing the desired compound were collected, the solution was concentrated down, and the addition of diethyl ether gave yellow precipitate which was filtered off, washed with diethyl ether and dried in vacuo.

Synthesis of Compounds 21 and 22

To a solution of N-(9-fluorenylmethoxycarbonyl)-3-aminopropionaldehyde (160 mg, 0.054 mmol) and S44HP (100 mg, 0.011 mmol) in DMF (3 mL) was added NaBH$_3$CN (34 mg, 0.054 mmol). The reaction mixture was kept at 37° C. for 20 hours and then added dropwise to diethyl ether (200 mL). The yellow precipitate of the mixture of compounds was filtered off and the individual compounds were separated and purified by flash chromatography on Merck Silica Gel for column chromatography (0.040-0.063 mm) in linear gradient system CHCl$_3$:MeOH:HCOOH (3:1:0.01)→CHCl$_3$:MeOH:H$_2$O:HCOOH (13:6:1:0.1) to yield N—[N-(9-fluorenylmethoxycarbonyl)-3-aminopropyl]-S44HP and N,N-di-[N-(9-fluorenylmethoxycarbonyl)-3-aminopropyl]-S44HP as yellow solids.

To a solution of N—[N-(9-fluorenylmethoxycarbonyl)-3-aminopropyl]-S44HP or N,N-di-[N-(9-fluorenylmethoxycarbonyl)-3-aminopropyl]-S44HP in DMSO (3 mL), piperidine (0.1 mL) was added. After 2 h at room temperature, diethyl ether mL) was added and an oily residue formed which was shaken successively with diethyl ether (7 mL×2). Addition of acetone (10 mL) gave yellow precipitate of compound 21 or compound 22 which was filtered off, washed with diethyl ether and dried in vacuo. The analytical data for the resulting compounds 21 and 22 is summarised in Table 2 below.

Synthesis of Compound 23

To a solution of S44HP (100 mg, 0.11 mmol) in dry DMF (2 mL) N$^\alpha$, N$^\epsilon$-di-(9-fluorenylmethoxycarbonyl)-L-lysine N-oxysuccinimide ester (221 mg, 0.33 mmol) and Et$_3$N (15.3 µl, 0.11 mmol) were added. The reaction mixture was kept at 37° C. for 1 h, then H$_2$O (5 mL) was added. The mixture was extracted with n-BuOH (3×5 mL). The organic fractions were combined and washed with 0.01 N HCl (1×5 mL) and H$_2$O (3×5 mL). The solution was concentrated and the addition of diethyl ether gave yellow precipitate, which was filtered off, washed with diethyl ether and purified by flash chromatography on silica gel (CHCl$_3$:MeOH:H$_2$O:HCOOH (13:4:0.5:0.01)). Fractions containing the desired compound were collected, the solution was concentrated and the addition of diethyl ether gave yellow precipitate which was filtered off, washed with diethyl ether and dried in vacuo.

To the isolated yellow solid (30 mg) in DMSO (3 mL) piperidine (0.1 mL) was added. After 2 h at room temperature, diethyl ether (~7 mL) was added, an oily residue formed and was shaken successively with diethyl ether (7 mL×2). Addition of acetone (10 mL) gave yellow precipitate which was filtered off, washed with diethyl ether and dried in vacuo.

TABLE 2

TLC (Rf), HPLC (Rt), MALDI mass spectra and solubility data for compounds 5-23

| | Molecular formula | Rf* | Rt** | MALDI MS Exact Mass Calculated | Found [M + Na]$^+$ | Water Solubility |
|---|---|---|---|---|---|---|
| 5 | $C_{49}H_{78}N_2O_{17}$ | 0.30 | 10.71 | 966.15 | 989.70 | + |
| 6 | $C_{48}H_{76}N_2O_{16}$ | 0.38 | 11.60 | 936.52 | 959.69 | + |
| 7 | $C_{49}H_{78}N_2O_{17}$ | 0.27 | 11.52 | 922.50 | 923.07## | − |
| 8 | $C_{48}H_{76}N_2O_{16}$ | 0.62 | 16.83 | 1036.57 | 1058.15 | − |
| 9 | $C_{57}H_{88}N_2O_{16}$ | 0.47 | 14.33 | 1008.54 | 1032.09 | + |
| 10 | $C_{51}H_{80}N_2O_{18}$ | 0.37 | 13.47 | 1008.54 | 1031.99 | − |
| 11 | $C_{52}H_{85}N_3O_{16}$ | 0.14 | 7.65 | 1007.59 | 1008.60## | + |
| 12 | $C_{50}H_{80}N_2O_{17}$ | 0.38 | 10.86 | 980.55 | 981.55## | ± |
| 13 | $C_{51}H_{80}N_2O_{19}$ | 0.58 | 11.55 | 1024.54 | 1025.57## | + |
| 14 | $C_{51}H_{80}N_2O_{19}$ | 0.58, 0.54 | 12.66, 13.22 | 1024.54 | 1025.48## | + |
| 15 | $C_{53}H_{85}N_3O_{17}$ | 0.55 | 7.43 | 1035.59 | 1059.16 | + |
| 16 | $C_{53}H_{84}N_2O_{21}$ | 0.12 | 9.35 | 1084.56 | 1085.48## | ± |
| 17 | $C_{53}H_{83}NO_{22}$ | 0.22 | 11.54 | 1085.54 | 1109.15 | ± |
| 18 | $C_{53}H_{83}NO_{22}$ | 0.22 | 13.98# | 1085.54 | 1109.00 | ± |
| 19 | $C_{59}H_{93}NO_{27}$ | 0.16 | 11.64 | 1247.59 | 1271.12 | ± |
| 20 | $C_{65}H_{95}N_3O_{17}$ | 0.63 | 14.35 | 1189.67 | 1212.72 | − |
| 21 | $C_{50}H_{80}N_2O_{17}$ | 0.14 | 9.78 | 980.55 | 981.58 | ± |
| 22 | $C_{53}H_{87}N_3O_{17}$ | 0.09 | 7.40 | 1037.60 | 1038.54 | ± |
| 23 | $C_{53}H_{85}N_3O_{18}$ | 0.06 | 7.70 | 1051.58 | 1052.65 | + |

*TLC on the Merck Silica Gel 60F254 plates in system of solvents CHCl$_3$:MeOH:H$_2$O:HCOOH (13:6:1:0.1).
**HPLC was carried out on a Shimadzu HPLC instrument of the LC 10 series on a Kromasil 100-C18 column (4 × 250 mm, particle size 6 µm) at an injection volume of 20 µL and a wavelength 408 nm. System comprised 0.01M H$_3$PO$_4$ at pH 2.6 and acetonitrile. The proportion of acetonitrile varied from 30 to 70% for 30 min with flow rate 1.0 mL/min.
HPLC isocratic system −35% MeCN.
[M + H]$^{+1}$
Water Solubility: + water solubility, ± sparingly soluble, − insoluble Following the synthetic principles set out above or below compounds 24 to 29 were also synthesized. In addition, the following further compounds have been prepared based on the synthetic protocols set out in FIGS. 10-16 and the schemes therein and the description which follows.

TABLE 3

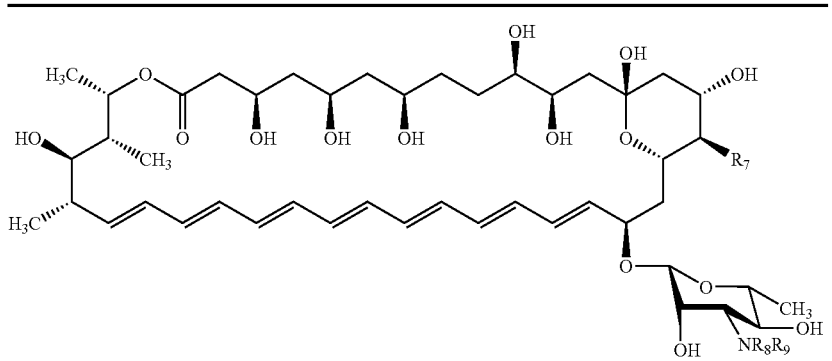

| No | $R_7$ | $R_8, R_9$ |
|----|-------|------------|
| Di-substituted derivatives of S44HP | | |
| 30 | $CONHCH_2CH_2CH_2NMe_2$ | 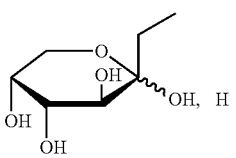 (fructopyranosyl) |
| 31 | $CONHCH_2CH_2CH_2NMe_2$ | 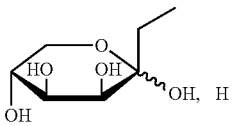 (tagatopyranosyl) |
| 32 | $CONHCH_2CH_2CH_2NMe_2$ | $CH_2C_6H_4NMe_2$-p, H |
| 33 | $CONHCH_2CH_2CH_2NMe_2$ | $COCH[(CH_2)_4NH_2]NH_2$, H (L-lysyl) |
| 34 | $CONHCH_2CH_2CH_2NMe_2$ | $COCH_2NMe_2$, H (N,N-di-Me-glycyl) |
| 35 | $CONHCH_2CH_2CH_2NMe_2$ | $COC_6H_4CH_2NH_2$-p, H |
| 36 | $CONHCH_2CH_2CH_2OH$ | 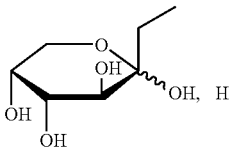 (fructopyranosyl) |
| 37 | $CONHCH_2CH_2CH_2OH$ | $CH_2C_6H_4NMe_2$-p, H |
| 38 | $CONHCH_2CH_2CH_2OH$ | $COCH[(CH_2)_4NH_2]NH_2$, H (L-Lys) |
| 39 | $CONHCH_2CH_2CH_2OH$ | $COCH_2NMe_2$, H (N,N-di-Me-glycyl) |
| 40 | $CONHCH_2CH_2CH_2OH$ | $COC_6H_4CH_2NH_2$-p, H |
| 41 | $CONHCH_2CH_2NMe_2$ | 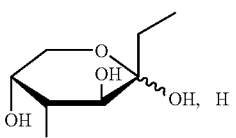 (fructopyranosyl) |

TABLE 3-continued

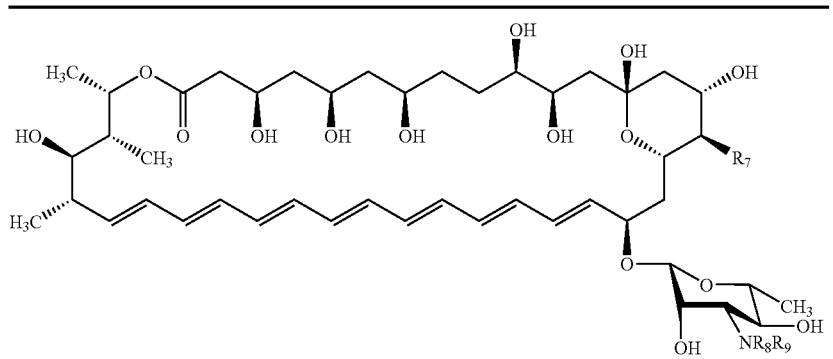

| No | R$_7$ | R$_8$, R$_9$ |
|---|---|---|
| 42 | CONHCH$_2$CH$_2$NMe$_2$ | 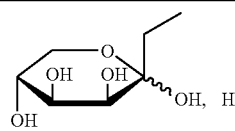 (tagatopyranosyl) |
| 43 | CONHCH$_2$CH$_2$NMe$_2$ | CH$_2$C$_6$H$_4$NMe$_2$-p, H |
| 44 | CONHCH$_2$CH$_2$NMe$_2$ | COCH[(CH$_2$)$_4$NH$_2$]NH$_2$, H (L-lysyl) |
| 45 | CONHCH$_2$CH$_2$NMe$_2$ | COCH$_2$NMe$_2$, H (N,N-di-Me-glycyl) |
| 46 | CONHCH$_2$CH$_2$NMe$_2$ | COC$_6$H$_4$CH$_2$NH$_2$-p, H |
| 47 | COOH | COC$_6$H$_4$CH$_2$NH$_2$-p, H |
| 48 | CONHCH$_2$CH$_2$NMe$_2$ | H, H |
| 49 | CH$_3$ | 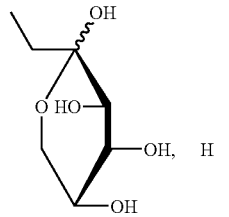 (fructopyranosyl) |
| 50 | CH$_3$ | CH$_2$C$_6$H$_4$NMe$_2$-p, H |
| 51 | CH$_3$ | COCH[(CH$_2$)$_4$NH$_2$]NH$_2$, H (L-lysyl) |
| 52 | CH$_3$ | (CH$_2$)$_3$NH$_2$, (CH$_2$)$_3$NH$_2$ |
| 53 | CH$_3$ | H,H - hydrochloride |
| 54 | CH$_3$ | H,H - D-glutamate |
| 55 | CH$_3$ | H,H - L aspartate |
| 56 | CH$_3$ | H,H - methylsulfonate |
| 57 | CH$_3$ | H,H - dichloroacetate |

Compound 28 is the glutamate salt of compound 48.

TABLE 4

Properties of the derivatives of S44HP and Compound 1: TLC (Rf), HPLC (Rt), MALDI mass spectra and solubility data

| Compounds No. | Molecular formula | Rf* (systems: I, II, III, IV) | Rt** (systems: A, B, C, D, E) | MALDI MS: Exact Mass Calculated | MALDI MS: Exact Mass Found [M + Na]$^+$ | Water Solubility |
|---|---|---|---|---|---|---|
| Di-substituted derivatives of S44HP | | | | | | |
| 30 | C$_{58}$H$_{95}$N$_3$O$_{21}$ | 0.57 (IV) | 14.07 (B) | 1169.65 | 1192.63 | + |
| 31 | C$_{58}$H$_{95}$N$_3$O$_{21}$ | 0.53 (III) | 12.21 (A) | 1169.65 | 1192.47 | + |
| 32 | C$_{61}$H$_{96}$N$_4$O$_{16}$ | 0.55 (III) | 24.78 (B) | 1140.68 | 1163.65 | − |
| 33 | C$_{58}$H$_{97}$N$_5$O$_{17}$ | 0.02 (I) | 9.98 (A) | 1135.69 | 1158.73 | ± |
| 34 | C$_{56}$H$_{92}$N$_4$O$_{17}$ | 0.20 (III) | 11.49 (A) | 1092.65 | 1115.41 | + |
| 35 | C$_{60}$H$_{92}$N$_4$O$_{17}$ | 0.01 (I) | 11.98 (A) | 1140.68 | 1141.54$^\#$ | − |

TABLE 4-continued

Properties of the derivatives of S44HP and Compound 1: TLC (Rf), HPLC (Rt), MALDI mass spectra and solubility data

| Compounds No. | Molecular formula | Rf* (systems: I, II, III, IV) | Rt** (systems: A, B, C, D, E) | MALDI MS: Exact Mass Calculated | Found [M + Na]+ | Water Solubility |
|---|---|---|---|---|---|---|
| 36 | $C_{56}H_{89}NO_{22}$ | 0.57 (IV) | 13.22 (A) | 1142.6 | 1165.58 | ± |
| 37 | $C_{59}H_{90}N_2O_{17}$ | 0.53 (III) | 18.25 (A) | 1113.63 | 1136.53 | − |
| 38 | $C_{56}H_{92}N_4O_{18}$ | 0.02 (I) | 8.50 (C) | 1108.64 | 1109.49# | + |
| 39 | $C_{54}H_{87}N_3O_{18}$ | 0.47 (III) | 13.10 (A) | 1065.60 | 1070.49## | ± |
| 40 | $C_{58}H_{87}N_3O_{18}$ | (0.2) (I) | 14.03 (A) | 1113.63 | 1136.57 | − |
| 41 *** | $C_{57}H_{92}N_2O_{21}$ | 0.53 (IV) | 14.92 (D) | 1155.63 | 1178.55 | + |
| 42 | $C_{57}H_{92}N_2O_{21}$ | 0.52 (III) | 11.00 (A) | 1155.63 | 1156.47# | + |
| 43 | $C_{60}H_{93}N_3O_{16}$ | 0.51 (III) | 14.69 (A) | 1126.67 | 1149.57 | − |
| 44 *** | $C_{57}H_{95}N_5O_{17}$ | 0.01 (I) | 9.93 (A) | 1121.67 | 1122.49# | + |
| 45 | $C_{55}H_{90}N_4O_{17}$ | 0.29 (III) | 11.43 (A) | 1078.63 | 1079.41# | ± |
| 46 | $C_{59}H_{90}N_4O_{17}$ | 0.01 (I) | 12.10 (A) | 1126.63 | 1149.56 | − |
| Mono-substituted derivatives of S44HP | | | | | | |
| 47 | $C_{55}H_{80}N_2O_{18}$ | 0.24 (I) | 14.52 (A) | 1056.54 | 1079.44 | − |
| 48 | $C_{51}H_{83}N_3O_{16}$ | 0.24 (I) | 10.70 (A) | 993.61 | 1016.58 | ± |
| Mono-substituted derivatives of Cmpd 1 | | | | | | |
| 49 *** | $C_{53}H_{85}NO_{20}$ | 0.65 (IV) | 10.20 (A) | 1055.57 | 1060.39## | ± |
| 50 | $C_{56}H_{86}N_2O_{15}$ | 0.85 (III) | 25.39 (B) | 1026.60 | 1049.49 | − |
| 51 | $C_{53}H_{87}N_3O_{16}$ | 0.03 (I) | 13.05 (A) | 1021.61 | 1026.50## | ± |
| 52 | $C_{53}H_{89}N_3O_{15}$ | 0.02 (III) | 10.07 (A) | 1007.63 | 1008.54# | ± |
| Water soluble salts of Cmpd 1 | | | | | | |
| 53 | $C_{47}H_{76}ClNO_{15}$ | 0.31 (III) | 18.30 (B) | 929.49 | — | + |
| 29 | $C_{52}H_{84}N_2O_{19}$ | 0.32 (III) | 18.41 (B) | 1040.57 | — | + |
| 54 | $C_{52}H_{84}N_2O_{19}$ | 0.31 (III) | 18.40 (B) | 1040.57 | — | + |
| 55 | $C_{51}H_{82}N_2O_{19}$ | 0.31 (III) | 18.40 (B) | 1026.55 | — | + |
| 56 | $C_{48}H_{79}NO_{18}S$ | 0.32 (III) | 18.36 (B) | 989.50 | — | + |
| 57 | $C_{49}H_{77}Cl_2NO_{17}$ | 0.31 (III) | 18.36 (B) | 1021.46 | — | + |

Purity of the obtained analogues for the initial testing of antifungal activity was 85-95%.
*TLC on Merck Silica Gel 60F254 plates in a solvent system: I - $CHCl_3$:MeOH:$H_2O$:HCOOH (13:6:1:0.1), II - $CHCl_3$:MeOH:$H_2O$:HCOOH (7:1:0.01:0.01), III - $CHCl_3$:MeOH:$H_2O$:$NH_4OH$ conc. (13:6:0.7:0.01), IV - AcOEt:n-ProOH:$NH_4OH$ conc. (15:10:10).
**Analytical reverse phase HPLC was carried out on a Shimadzu HPLC instrument of the LC 10 series on a Kromasil 100-C18 column (4 × 250 mm, particle size 6 μm) at an injection volume of 20 μL and a wavelength 408 nm with flow rate 1.0 mL/min. The solvent system comprised: A - 0.2% $HCOONH_4$ pH 4.5 and MeCN the proportion of MeCN varied from 30 to 70% for 30 min., B - 0.2% $HCOONH_4$ pH 4.5 and MeCN: 25 → 65%, 40 min.; C - 0.2% $HCOONH_4$ pH 4.5 and MeCN, 30 → 90%, 30 min., 90 → 90%, 10 min.; D - isocratic system −35% MeCN.
***Hydrochloride. Water Solubility: + water solubility, ± sparingly soluble, − insoluble
$[M + H]^{+1}$;
$[M - H_2O + Na]^{+1}$ Synthesis of Further S44HP Derivatives (Compounds 30 to 48).
General The reactions were monitored by TLC on Merck Silica Gel 60F254 plates in a solvent system: I—$CHCl_3$:MeOH:$H_2O$:HCOOH (13:6:1:0.1), II—$CHCl_3$:MeOH:$H_2O$:HCOOH (7:1:0.01:0.01), III—$CHCl_3$:MeOH:$H_2O$:$NH_4OH$ conc. (13:7:1:0.1), IV—AcOEt:n-ProOH:$NH_4OH$ conc. (15:10:10).

Analytical reverse phase HPLC was carried out on a Shimadzu HPLC instrument of the LC 10 series on a Kromasil 100-C18 column (4×250 mm, particle size 6 μm) at an injection volume of 20 μL and a wavelength 408 nm with flow rate 1.0 mL/min. The solvent system comprised: A—0.2% $HCOONH_4$ pH 4.5 and MeCN the proportion of MeCN varied from 30 to 70% for 30 min.; B—0.2% $HCOONH_4$ pH 4.5 and MeCN: 25→65%, 40 min.; C—0.2% $HCOONH_4$ pH 4.5 and MeCN, 30→90%, 30 min., 90→90%, 10 min.; D—isocratic system—35% MeCN; E—0.01M $H_3PO_4$ at pH 2.6 and MeCN, 30→70%, 30 min. F—0.01M $H_3PO_4$ at pH 2.6 and MeCN, 40→80%, 30 min.

Di-Modified Derivatives of S44HP.

N-Fructosyl S44HP N,N-dimethylaminopropyl amide (DMAP), -hydroxypropyl amide (HP) or —N,N-dimethylaminoethyl (DMAE) amide (Compounds 30, 36, 41 respectively); N-tagatopyronosyl S44HP DMAP amide (Compound 31) or N-tagatopyronosyl S44HP DMAE amide (Compound 42) (Scheme 1, left side).

1st Step (Amidation)—S44HP DMAP Amide (Compound 11), HP Amide (Compound 12) or DMAE Amide (Compound 48).

To a mixture of S44HP (36 mg, 0.04 mmol) and 0.12 mmol of the appropriate amine hydrochloride dissolved in 0.6 mL of DMSO was added, portion-wise, $Et_3N$ to adjust pH 8-8.5 and afterwards during 15 minutes 0.06 mmol of PyBOP-reagent. The reaction mixture was stirred at room temperature for 1 hour. Subsequent addition of diethyl ether (~5 mL) to the reaction mixture led to an oily residue, which was shaken successively with diethyl ether (5 mL×2). After addition of 8 mL of acetone to this oil, a yellow precipitate of amide was formed. The precipitate was filtrated, washed with acetone and then dried in vacuo. Crude amide (85-90% of purity by HPLC data, and containing salts) was purified by column chromatography on Sephadex G-25 (Pharmacia Fine Chemicals AB, Uppsala, Sweden). Column was performed using water. Purity of the fraction was controlled by HPLC resulting in target of appropriate S44HP amide purity >92% by HPLC.

2nd Step (Amadori Rearrangement of Amides):

D-Glucose or D-galactose (0.086 mmol) was added to a solution of appropriate S44HP amide (Compound 11, 12, 48) (0.040 mmol) in DMF (2 mL). The reaction mixture was kept at 37° C. for 20 hours. Then the reaction mixture was added dropwise to diethyl ether (50 mL). The resulting precipitate was filtered off, washed with diethyl ether and dried. Crude compound (85-90% of purity by HPLC data, and containing salts) was purified by column chromatography on Sephadex G-25 (Pharmacia Fine Chemicals AB, Uppsala, Sweden). Column was performed using water. Purity of the fraction was controlled by TLC, system IV. Fractions containing the desired compound were collected and the solution was concentrated. The addition acetone gave yellow precipitate which was filtered off, washed with acetone and dried in vacuo. The compound 41 was obtained as hydrochloride. To the solution of Compound 41 in methanol 0.1N HCl in methanol to pH ~4. The addition of diethyl ether gave yellow precipitate which was filtered off, washed with diethyl ether and dried in vacuo. The purity of N-alkyl derivative of S44HP amide was >92%. The analytical data for these compounds (30, 36, 41, 31, 42) is summarized in Table 4 above.

N—(4-N,N-Di-methylaminobenzyl) S44HP DMAP Amide, -HP Amide or -DMAE Amide (Compound 32, 37, 43, Respectively) (Scheme 1 (FIG. 10), Right Side).

1st Step (Amidation).

S44HP DMAP amide (Compound 11), HP amide (Compound 12) or DMAE amide (Compound 48) were obtained as described above for Compound 30 (1st Step).

2nd Step (Reductive N-Alkylation of Amides).

The solution of 4-N,N-dimethylaminobenzaldehyde (0.065 mmol) and appropriate S44HP amide (Compound d11, 12 or 48) (0.022 mmol) in DMF (2 mL) was kept at 37° C. for 2 h then NaBH$_3$CN (4.1 mg, 0.065 mmol) was added. The reaction mixture was kept at 37° C. for 20 h. Addition of diethyl ether (10 mL) led to an oily residue, which was shaken successively with diethyl ether (10 mL×2). Yellow precipitate was formed after addition of acetone (10 mL). The precipitate was filtered off, washed with diethyl ester and dried. Crude compound containing salts was purified by column chromatography on silica gel Merck using the system CHCl$_3$:MeOH:H$_2$O:HCOOH (13:6:1:0.1). Purity of the fraction was controlled by TLC, system I. Fractions containing the desired compound collected and the solution was concentrated. The addition acetone gave yellow precipitate which was filtered off, washed with acetone and dried in vacuo. The purity of N-alkyl derivative of appropriate S44HP amide was >92%. The analytical data for these compounds is summarized in Table 4 above.

Figure 11:
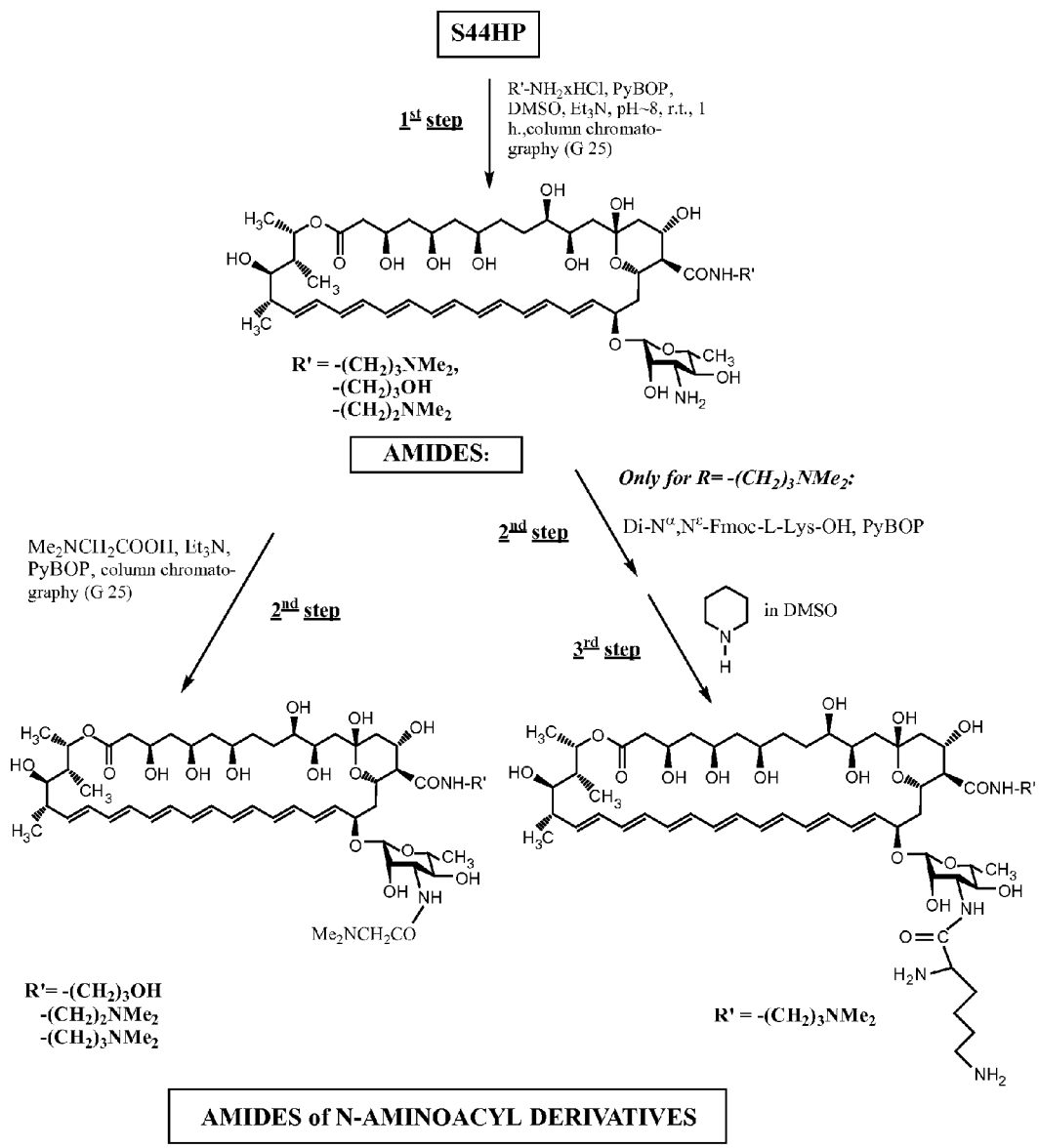
FIG. 11 shows scheme 2, a scheme for the preparation of Amides of N-Aminoacyl derivatives of a compound of the disclosure.

N—(N,N-dimethylglycyl) S44HP DMAE Amide, -HP Amide or -DMAP Amide (Compound 39, 45, 34 Respectively) (N-aminoacylation of Amides, Scheme 2 (FIG. 11, Left Side).

To a mixture of N,N-dimethylglycine (0.04 mmol) and appropriate S44HP DMAE amide (Compound 48), -HP amide (Compound 12) or -DMAP amide (Compound 11) (see Scheme 1) (0.02 mmol) in 0.5 mL of DMSO, Et$_3$N to adjust pH 8 was added, and afterwards 0.03 mmol of PyBOP-reagent portion-wise during 15 minutes. The reaction mixture was stirred at room temperature for 1 hour. Subsequent addition of diethyl ether (~3 mL) to the reaction mixture led to an oily residue, which was shaken successively with diethyl ether (3 mL×2). After addition of 5 mL of acetone to this oil, a yellow precipitate of amide was formed. The precipitate was filtrated, washed with acetone and then dried in vacuo yielding N—(N,N-dimethylglycyl) S44HP DMAE amide, -HP amide or -DMAP amide (Compound 39, 45, 34). The analytical data for these compounds is summarized in Table 4 above.

N—(N-L-Lysyl) S44HP HP Amide and -DMAE Amide (Compound 38 and 44 Respectively) (Scheme 2, Right Side).

1st Step: (N—[N-Fmoc-amino]acylation)—N—(N$^α$,N$^ε$-di-Fmoc-L-lysyl) S44HP.

To the cooled to ~+5° C. solution of N$^α$,N$^ε$-di-(9-fluorenylmethoxycarbonyl)-L-lysine (180 mg, 0.33 mmol), N-hydroxybenzotriazole (54 mg, 0.4 mmol) in dry DMF (1.2 mL) DCC (62 mg, 0.3 mmol) was added, and the reaction mixture was stirred at ~+5° C. for 1 h. The residue of DCU was filtered off, and the obtained eluate was added to S44HP (184 mg, 0.2 mmol) in DMF (1.0 mL). Then to the reaction mixture (i-Pro)$_2$EtN (0.1 mL, 0.81 mmol) was added dropwise during 10 min. under stirring. The reaction mixture was stirring at r.t. for 2 h under TLC control in the system: CHCl$_3$:MeOH:H$_2$O:HCOOH (6:1:0.01:0.02), and then 20 mL of ethyl ether were added. The obtained precipitate was filtered off, washed by the mixture of ethyl ether: acetone (1:1, 10 ml×3) and dried in vacuum yielding 202 mg of yellow powder. The crude compound was purified by column chromatography on silica gel Merck. Column was performed using the system: CHCl$_3$:MeOH:H$_2$O:HCOOH (9:1:0.01:0.02→7:1:0.01:0.02). Purity of the fraction was controlled by TLC in the system II. Fractions containing the desired compound collected and the solution was concentrated. The addition acetone gave yellow precipitate which was filtered off, washed with acetone and dried in vacuo yielding 60 mg of pure N—[N$^α$,N$^ε$-di-(9-fluorenylmethoxycarbonyl)-L-lysyl] S44HP (>96%, HPLC, Rt=22.80, system B). MALDI mass-spectra. Found: 1500.542 [M-H$_2$O+Na]$^{+1}$. Calculated for C$_{83}$H$_{105}$N$_3$O$_{22}$ 1495.72 (exact Mass).

2nd Step (Amidation of N—(N$^α$,N$^ε$-di-Fmoc-L-lysyl) S44HP—N—(N$^α$,N$^ε$-di-Fmoc-L-lysyl) S44HP HP amide or -DMAE amide:

To a mixture of N—(N$^α$,N$^ε$-di-Fmoc-L-lysyl) S44HP (0.02 mmol) and 0.06 mmol of 3-hydroxypropyl amine hydrochloride or 4-(N,N-dimethylamino)propyl amine dihydrochloride dissolved in 0.3 mL of DMSO was added, portion-wise, Et$_3$N to adjust pH 7-7.5 and afterwards during 15 minutes 0.03 mmol of PyBOP-reagent. The reaction mixture was stirred at room temperature for 1 hour under TLC control in the system CHCl$_3$:MeOH:H$_2$O:NH$_4$OH conc.(5:1:0.01:0.01). Subsequent addition of diethyl ether (~3 mL) to the reaction mixture led to an oily residue, which was shaken successively with diethyl ether (3 mL×2). After addition of 5 mL of acetone to this oil, a yellow precipitate of amide was formed. The precipitate was filtrated, washed with acetone and then dried in vacuo yielding the appropriate N—(N$^α$,N$^ε$-di-Fmoc-L-lysyl) S44HP HP-amide or (N$^α$,N$^ε$-di-Fmoc-L-lysyl) S44HP-DMAE amide with the purity ~90%, by HPLC data: Rt=21.43 (C) and 20.39 (B), respectively. TLC data: Rf=0.47 and Rf=0.43, respectively, in the system CHCl$_3$:MeOH:H$_2$O:NH$_4$OH conc. (5:1:0.01:0.01).

3rd Step (Fmoc removal).

The appropriate N—(N$^α$,N$^ε$-di-Fmoc-L-lysyl) S44HP amide (30 mg) was dissolved in DMSO (3 mL) piperidine (0.1 mL) was added. After 2 h at room temperature, diethyl ether (~7 mL) was added, an oily residue formed and was shaken successively with diethyl ether (7 mL×2). Addition of acetone (10 mL) gave yellow precipitate which was filtered off, washed with diethyl ether and dried in vacuo. The compound Compound 44 was obtained as hydrochloride. To the solution of Compound 44 in methanol 0.1N HCl in methanol was added to pH ~4. The addition of diethyl ether gave yellow precipitate which was filtered off, washed with diethyl ether and dried in vacuo. The analytical data for these two compounds is summarized in Table 4 above.

Figure 12:
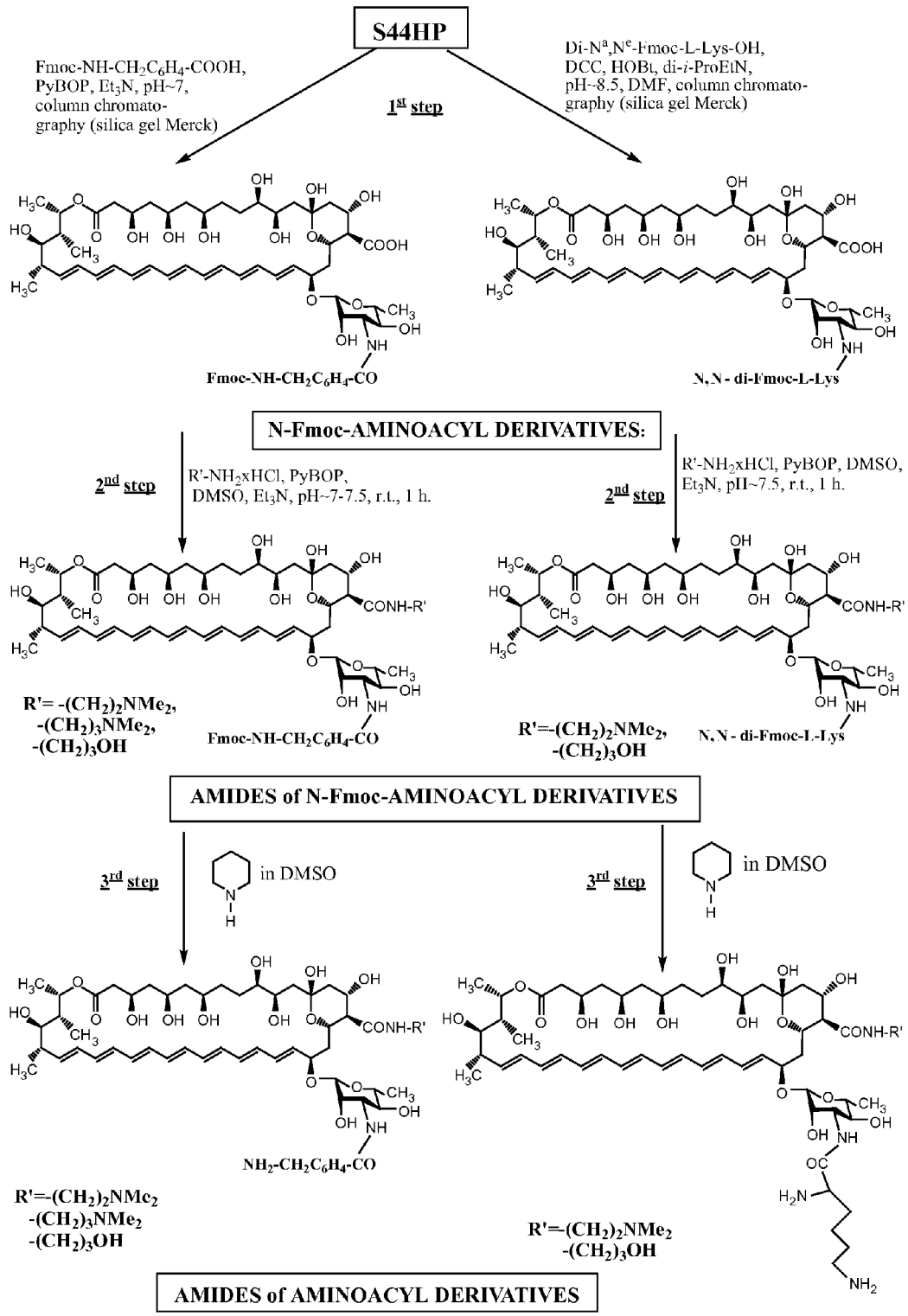
FIG. 12 shows scheme 3, a scheme for the preparation of Amides of N-Aminoacyl derivatives of a compound of the disclosure.
Figure 15:
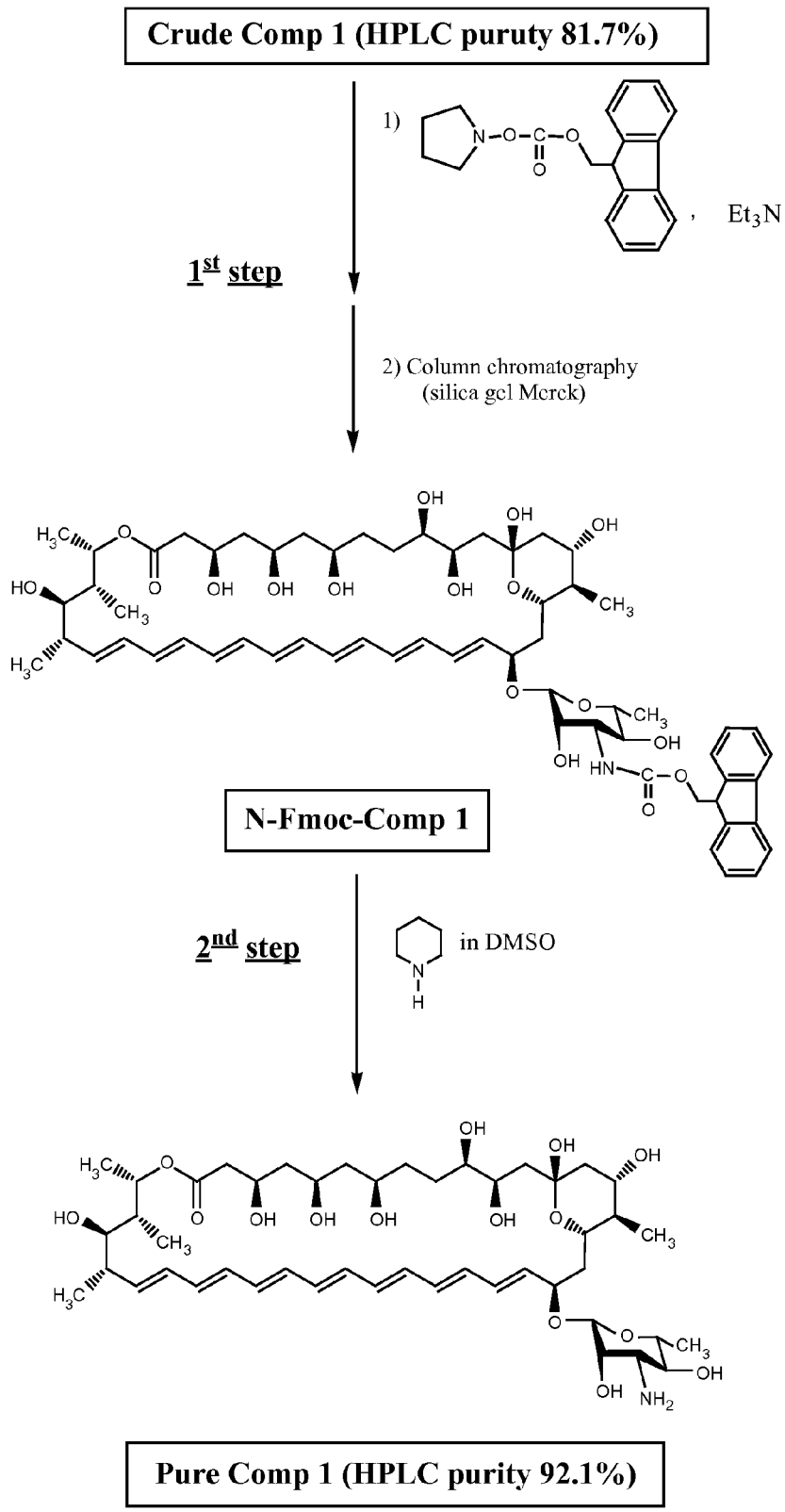
FIG. 15 shows scheme 6, a scheme for the purification of Compound 1, starting from crude Comp 1.
Figure 16:
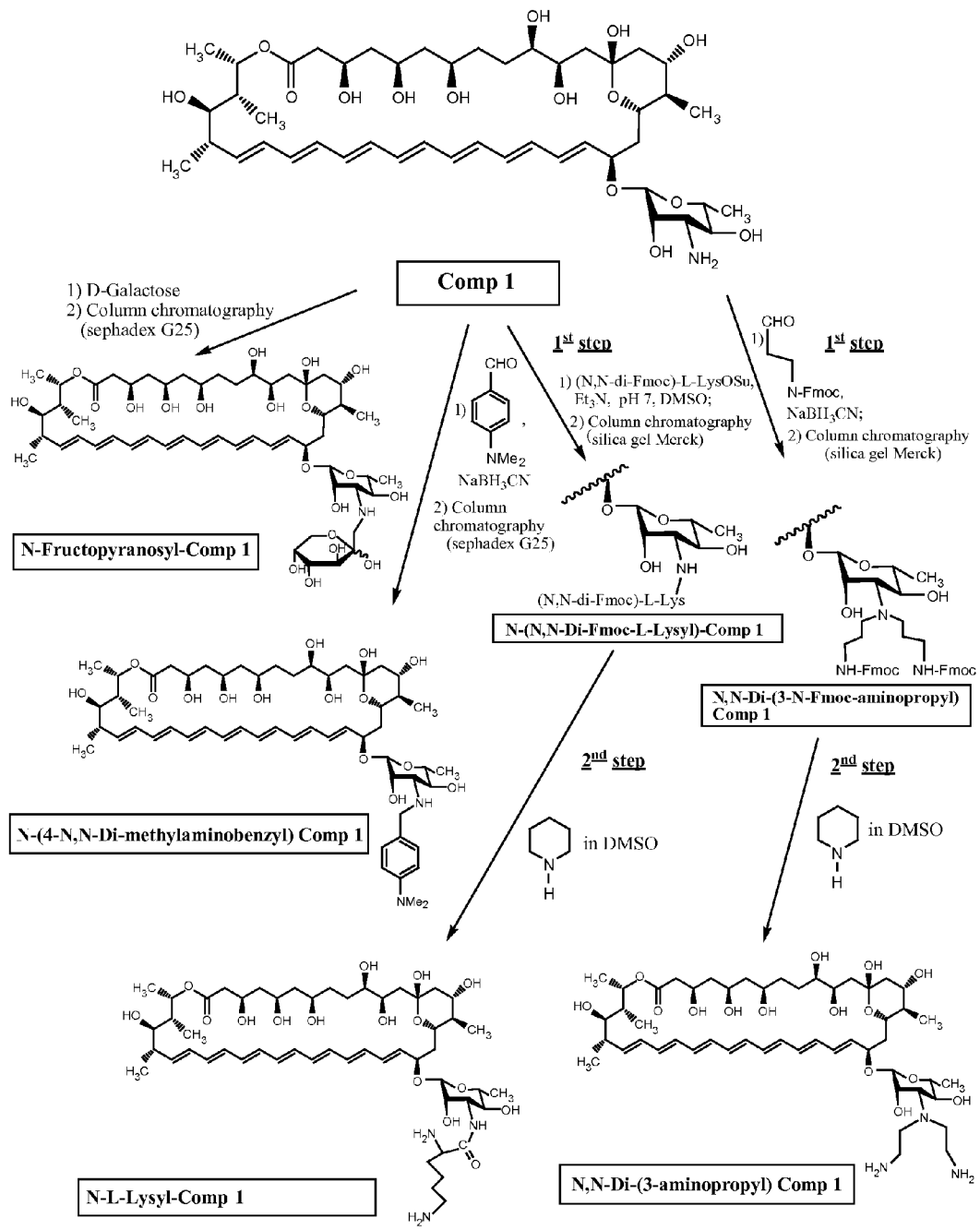
FIG. 16 shows scheme 7, a scheme for the preparation of various compounds of the disclosure.

N-(4-Aminomethyl-benzoyl) S44HP DMAP Amide, -HP Amide, -DMAE Amide (Compound 35, 40, 46 Respectively) (Scheme 3, FIG. 12, Left Side).

1st Step (N-[4-Fmoc-aminomethyl]benzoylation)—N-(4-Fmoc-aminomethyl benzoyl) S44HP:

The derivatives were obtained in the conditions as for Compound 38 (1st Step). To a solution of 4-N-Fmoc-aminomethylbenzoic acid (80 mg, 0.022 mmol) and S44HP (100 mg, 0.11 mmol) in DMSO (3 mL), $Et_3N$ to adjust pH7, and PyBOP (90 mg, 0.165 mmol) was added. The reaction mixture was kept at r.t. for 20 h and then dropwise to diethyl ether (200 mL) was added. The yellow precipitate was filtered off and purified by column chromatography on Merck Silica Gel for column chromatography (0.040-0.063 mm) in the system $CHCl_3$:MeOH:HCOOH (3:1:0.01) to yield N-(4-N-Fmoc-aminomethyl)benzoyl S44HP (Compound 47) with the purity ~95%, by HPLC data (Rt=18.18, system B). TLC (Rf=0.61, I)

2nd Step (Amidation of N-[4-Fmoc-aminomethyl]benzoyl S44HP)—N-(4-Fmoc-aminomethylbenzoyl) S44HP DMAP amide, -HP amide, or -DMAE amide.

The derivatives were obtained in the conditions as for Compound 38 (2nd Step), starting from N-(4-Fmoc-aminomethylbenzoyl) S44HP and appropriate DMAP-, HP- or DMAE amine and using PyBOP reagent. The reaction mixture was stirring for 4 h. The purity was ~85-93%, by HPLC data: N-(4-Fmoc-aminomethylbenzoyl) S44HP DMAP amide (Rt=15.88, B; Rf=0.25, I), N-(4-Fmoc-aminomethyl-benzoyl) S44HP HP amide (Compound 12) (Rt=17.14, B; Rf=0.60, I), or N-(4-Fmoc-aminomethylbenzoyl) S44HP DMAE amide (Rt=15.95, B; Rf=0.24, I), 3rd Step (Fmoc-removal).

The derivatives were obtained in the conditions as for Compound 38 (3rd Step), starting from N-(4-Fmoc-aminomethylbenzoyl) S44HP DMAP amide, -HP amide or -DMAE amide. The analytical data for these three compounds is summarised in Table 2 below.

N-L-lysyl S44HP DMAP-Amide (Compound 33) (Scheme 3, Right Side).

1st Step (Amidation)—S44HP DMAP-amide (Compound 11):

S44HP DMAP amide was obtained as for Compound 33 (Scheme 1, left side). The purity was ~90% (HPLC).

2nd Step (N—[N-Fmoc-amino]acylation of DMAP amide)— N—($N^\alpha,N^\epsilon$-di-Fmoc-L-lysyl) S44HP DMAP-amide:

To a solution of S44HP DMAP amide (0.02 mmol) in DMSO (0.5 mL) $N^\alpha,N^\epsilon$-di-Fmoc-L-lysine (0.04 mmol) and $Et_3N$ were added (pH 7-7.5) and afterwards during 15 minutes 0.03 mmol of PyBOP-reagent. The reaction mixture was stirred at room temperature for 1 hour. Subsequent addition of diethyl ether (~3 mL) to the reaction mixture led to an oily residue, which was shaken successively with diethyl ether (3 mL×2). After addition of 5 mL of acetone to this oil, a yellow precipitate of amide was formed. The precipitate was filtrated, washed with acetone and then dried in vacuo yielding N—($N^\alpha,N^\epsilon$-di-Fmoc-L-lysyl) S44HP DMAP amide with the purity ~95%, by HPLC data (Rt=22.01, system B).

3rd Step (Fmoc-removal).

The derivatives were obtained in the conditions as for Compound 38 (3rd Step), starting from N—($N^\alpha,N^\epsilon$-di-Fmoc-L-lysyl) DMAP amide. The analytical data for these two compounds is summarized in Table 4 above.

Mono-Modified Derivatives of S44HP

N-(4-Aminomethylbenzoyl) S44HP (Compound 47) (see Scheme 4, FIG. 13, Fmoc-removal) was obtained in the conditions as for Compound 38 (3rd Step), starting from N-(4-Fmoc-aminomethylbenzoyl) S44HP (obtained according Scheme 3, 1st Step). The analytical data for these two compounds is summarized in Table 4 above.

N,N-dimethylaminoethyl (DMAE) S44HP Amide (Compound 48) (Alternative Method, Scheme 5, FIG. 14).

1st Step (Fmoc-introduction). N-Fmoc-S44HP.

To a stirred solution of 500 mg (0.5 mmol) of crude S44HP in 6 mL DMF:MeOH (5:1), 0.057 mL (0.65 mmol) pyridine and 360 mg (1.0 mmol) of FmocOSu was added portionwise. The reaction mixture was stirred at room temperature for 4 h. Subsequent addition of diethylether (20 mL) to the reaction mixture led to yellow precipitate of N-Fmoc-S44HP. The precipitate was filtered and washed with diethylether and dried. The crude N-Fmoc-S44HP was purified by column chromatography on Merck silica gel in the system $CHCl_3$:MeOH:$H_2O$:HCOOH (13:6:1:0.05) to yield ~30% of N-Fmoc-S44HP with the purity 94% by HPLC (Rt=20.49, system: 0.01M $H_3PO_4$ at pH 2.6 and MeCN, 40→80%, 30 min. TLC 0.39 (III).

2nd Step (Amidation) N-Fmoc-S44HP DMAE amide.

To a stirred solution of 115 mg (0.10 mmol) of N-Fmoc-S44HP in 2 ml DMSO 37 mg (0.30 mmol) of N,N-dimethylaminoethylamine hydrochloride and $Et_3N$ adjust pH 7-7.5 were added 78 mg (0.15 mmol) PyBOP were added portionwise; pH of reaction mixture was kept 7-7.5 by adding $Et_3N$. The reaction mixture was stirred at room temperature for 1 h. Subsequent addition of diethyl ether (5 mL) to the reaction mixture led to an oily residue, which was shaken successively with diethyl ether (5 mL). Addition of acetone (10 mL) led to the yellow precipitate, which was filtrated off, washed with acetone and dried to give N-Fmoc-S44HP DMAE amide with the purity ~92%, by HPLC data (Rt=14.50, system A).

3rd Step (Fmoc-removal).

The derivative—(Compound 48) was obtained in the conditions as for Compound 38 (3rd Step), starting from N-Fmoc-S44HP DMAE amide. The analytical data for this compound is summarized in Table 4 above.

Pure Compound 1: Purification Compound 1, Starting from the Sample of Crude Compound 1 (Scheme 6, FIG. 15).

1st Step (Fmoc-Introduction and Purification).

N-Fmoc-Compound 1.

To a stirred solution of 2000 mg (2.0 mmol) of crude Compound 1 (containing compound 1-81.5%, S44HP—8.27% and unknown impurity ~10% by HPLC data, system B) in 40 mL DMSO $Et_3N$ was added to adjust pH 7-7.5 1400 mg (4.0 mmol) of FmocOSu were added portionwise; pH of the reaction mixture was kept 7-7.5 by adding of $Et_3N$. The reaction mixture was stirred at room temperature for 2 h. Subsequent addition of diethylether (200 mL) to the reaction mixture led to an oily residue, which was shaken successively with diethylether (150 mL×3). After addition of 50 mL of acetone to this residue diethylether (50 mL) was added to give yellow precipitate. The precipitate was filtered and washed with diethylether and dried in vacuo yielding 2200 mg of crude N-Fmoc-compound 1 which was purified by column chromatography on Merck silica gel in the system $CHCl_3$:MeOH:$H_2O$:25% $NH_4OH$ (13:6:1:0.05) to yield 650 mg (~30%) of N-Fmoc-compound 1 with the purity 86% by HPLC (Rt=18.44, system C).

2nd Step (Fmoc-Removal).

Fmoc-compound 1 (400 mg) was dissolved in DMSO (60 mL) piperidine (0.2 mL) at 15° C. was added. After 2 h at 15° C., diethyl ether (~50 mL) was added; an oily residue formed and was shaken successively with diethyl ether (50 mL×3). Addition of acetone (10 mL) and diethylether (20 mL) gave yellow precipitate which was filtered off, washed with diethyl ether and dried in vacuo yielding 300 mg of pure compound 1. The portion of pure compound 1 for HPLC was obtained as hydrochloride. To the solution of compound 1 (base) in methanol 0.1N HCl in methanol to pH ~4 was added. The addition of diethyl ether gave yellow precipitate which was filtered off, washed with diethyl ether and dried in vacuo with the purity 92.1% by HPLC data (hydrochloride, Rt=11.37, system A).

Mono-Modified Derivatives of Compound 1. (Scheme 7, FIG. 16).

N-Fructopyranosyl-Compound 1 (Compound 49) (Amadori Rearrangement):

D-Glucose (0.086 mmol) was added to a solution of compound 1 (0.040 mmol) in DMF (2 mL). The reaction mixture was kept at 37° C. for 20 hours. Then the reaction mixture was added dropwise to diethyl ether (50 mL). The resulting precipitate was filtered off, washed with diethyl ether and dried. Crude compound (85-90% of purity by HPLC data, and containing salts) was purified by column chromatography on Sephadex G-25 (Pharmacia Fine Chemicals AB, Uppsala, Sweden). Column was performed using water. Purity of the fraction was controlled by TLC, system IV. Fractions containing the desired compound were collected and the solution was concentrated. The addition acetone gave yellow precipitate which was filtered off, washed with acetone and dried in vacuo. The Compound 41 was obtained as hydrochloride. To the solution of Compound 49 in methanol 0.1N HCl in methanol to pH ~4 was added. The addition of diethyl ether gave yellow precipitate which was filtered off, washed with diethyl ether and dried in vacuo. The analytical data for N-Fructopyranosyl-Compound 1 (Compound 49) is summarised in Table 2 below.

N-(4-N,N-Di-methylaminobenzyl) Compound 1 (Compound 50) (Reductive N-alkylation).

The solution of 4-N,N-dimethylaminobenzaldehyde (0.065 mmol) and Compound 1 (0.022 mmol) in DMF (2 mL) was kept at 37° C. for 2 h then $NaBH_3CN$ (4.1 mg, 0.065 mmol) was added. The reaction mixture was kept at 37° C. for 20 h. Addition of diethyl ether (10 mL) led to an oily residue, which was shaken successively with diethyl ether (10 mL×2). Yellow precipitate was formed after addition of acetone (10 mL). The precipitate was filtered off, washed with diethyl ester and dried. Crude compound containing salts was purified by column chromatography on silica gel Merck using the system $CHCl_3$:MeOH:$H_2O$:HCOOH (13:6:1:0.1). Purity of the fraction was controlled by TLC, system I. Fractions containing the desired compound collected and the solution was concentrated. The addition acetone gave yellow precipitate which was filtered off, washed with acetone and dried in vacuo. The analytical data for N-(4-N,N-Di-methylaminobenzyl) Compound 1 (Compound 50) is summarized in Table 4 above.

N-L-Lysyl-Compound 1 (Compound 51)

1$^{st}$ Step (N—[N-Fmoc-amino] acylation). Solution of Compound 1 (50 mg, 0.055 mmol) in dry DMF (1 mL) was cooled at 10° C. and then $Et_3N$ (7.5 µl, 0.055 mmol) and $N^α,N^ε$-di-Fmoc-L-lysine N-oxysuccinimide ester (57 mg, 0.083 mmol) were added. The reaction mixture was stirred at this temperature for 1 hour. The current of the reaction was controlled by TLC in system of solvents $CHCl_3$-MeOH (6:1). Addition of diethyl ether (~5 ml) to the reaction mixture led to yellow precipitate, which was filtered off, washed with diethyl ether, dried in vacuo and purified by column chromatography on silica gel (system $CHCl_3$-MeOH with gradient of MeOH 0→10%). Fractions containing the desired compound were collected, the solution was concentrated and the addition of diethyl ether gave yellow precipitate which was filtered off, washed with diethyl ether and dried in vacuo. TLC: Rf=0.6 ($CHCl_3$-MeOH 6:1). HPLC: Rt=13.08 (0.2% $HCOONH_4$ pH 4.5 and MeCN: 75→90%, 20 min, 90→90%, 10 min)

2$^{nd}$ Step (Fmoc-Removal).

To the isolated yellow solid (22 mg, 0.015 mmol) in DMSO/MeOH 10:1 (1 mL) piperidine (4.5 µl, 0.045 mmol) was added. After 30 min of stirring at room temperature, diethyl ether (~3 mL) was added; an oily residue formed and was shaken successively with diethyl ether (3 mL×2). Addition of acetone (2 mL) gave yellow precipitate which was filtered off, washed with diethyl ether and dried in vacuo. The analytical data for N-L-Lysyl-Compound 1 (Compound 51) is summarized in Table 4 above.

N,N-Di-(3-aminopropyl)-Compound 1 (Compound 52)

1$^{st}$ Step (Reductive N-Alkylation)

To a solution of N-Fmoc-3-aminopropionaldehyde (160 mg, 0.054 mmol) and Compound 1 (100 mg, 0.011 mmol) in DMF (3 mL) was added $NaBH_3CN$ (34 mg, 0.054 mmol). The reaction mixture was kept at 37° C. for 20 hours and then added dropwise to diethyl ether (200 mL). The yellow precipitate was filtered off and purified by flash chromatography on Merck Silica Gel for column chromatography (0.040-0.063 mm) in linear gradient system $CHCl_3$:MeOH:HCOOH (3:1:0.01)→$CHCl_3$:MeOH:$H_2O$:HCOOH (13:6:1:0.1) to yield the yellow precipitate of N,N-Di-(N-Fmoc-3-aminopropyl) Compound 1. HPLC data: Rt=27.43 (C).

2$^{nd}$ Step (Fmoc-Removal).

To a solution of N,N-di-[3-(N-Fmoc)-aminopropyl]-S44HP in DMSO (3 mL), piperidine (0.1 mL) was added. After 2 h at room temperature, diethyl ether (~7 mL) was added and an oily residue formed which was shaken successively with diethyl ether (7 mL×2). Addition of acetone (10 mL) gave yellow precipitate which was filtered off, washed with diethyl ether and dried in vacuo. The analytical data for N,N-Di-(3-aminopropyl) Compound 1 (Compound 52) is summarized in Table 4 above.

Salts of Compound 1

L-aspartate (55), Compound 1 L-glutamate (29), D-glutamate (54)

Compound 1 (13 mg, 0.015 mmol) was dissolved in 0.2 ml DMSO and then the solution corresponding amino acid (0.015 mmol) in 0.1 ml water was added. The reaction mixture was kept at room temperature for 15 minutes. Addition of diethyl ether (~2 ml) to the reaction mixture led to an oily residue, which was shaken successively with diethyl ether (2 ml×2). After addition of 3 ml of acetone to this oil a yellow precipitate of salt was formed. The precipitate was filtrated, washed by acetone and then dried in vacuo.

Methylsulfonate (56), Dichloroacetate (57)

Corresponding acid (0.015 mmol) was dissolved in 0.1 ml DMSO and then was added to the solution Compound 1 (13 mg, 0.015 mmol) in 0.1 ml DMSO. The reaction mixture was kept at room temperature for 5 minutes. Addition of diethyl ether (~2 ml) to the reaction mixture led to an oily residue, which was shaken successively with diethyl ether (2 ml×2). After addition of 3 ml of acetone to this oil a yellow precipitate of salt was formed. The precipitate was filtrated, washed by acetone and then dried in vacuo.

Compound 1 Hydrochloride (53)

To the solution Compound 1 (13 mg, 0.015 mmol) in 0.2 ml DMSO was added 0.15 ml (0.015 mmol) of water solution 0.1N HCl. The reaction mixture was kept at room temperature for 5 minutes. Addition of diethyl ether (~2 ml) to the reaction mixture led to an oily residue, which was shaken successively with diethyl ether (2 ml×2). After addition of 3 ml of acetone to this oil a yellow precipitate of salt was formed. The precipitate was filtrated, washed by acetone and then dried in vacuo. All samples were obtained in the yields of about 90% and were water soluble.

Determination of Anti-Fungal Activity and Toxicity

Antifungal Susceptibility Study (1)

Antifungal susceptibility testing of yeasts and filamentous fungi (moulds) were determined by using the broth microdilution method described in NCCLS documents M27-A [*Reference method for Broth Dilution Antifungal Susceptibility Testing of Yeasts*, ISBN 1-56238-328-0, Pennsylvania, 1997] and M38-A [*Reference method for Broth Dilution Antifungal Susceptibility Testing of Filamentous Fungi: Approved Standard*, ISBN 1-56238-470-8, Pennsylvania, 2002], accordingly.

Medium and Buffer.

The medium RPMI 1640 with L-glutamine and phenol red, without sodium bicarbonate, supplemented with 0.2% glucose (ICN Biomedicals Inc., Ohio, USA), buffered with 0.165 M morpholinepropanesulfonic acid (MOPS; ACROS ORGANICS, New Jersey, USA), pH 7.0, was used in study.

Antifungal Agents.

The compounds were initially solubilized in dimethyl sulfoxide (DMSO) at a starting concentration of 1600 µg/mL. Series of dilutions (1600 to 3.13 µg/mL) were prepared from the stock solutions in the same solvent. Then these DMSO solutions were diluted 50-fold (first 10-fold and then 5-fold) in the test medium. Finally they were diluted 2-fold when inoculated, which reduced the final solvent concentration to 1% (final concentratioins of antifungal agents were 16 to 0.13 µg/mL). The solutions were prepared just before using.

Organisms.

The organisms used for susceptibility testing were: *Candida albicans* ATCC 14053, *Cryptococcus humicolus* ATCC 9949, *Aspergillus niger* ATCC 16404 and *Fusarium oxysporum* VKM F-140 (=CMI, IMI 90473). Organisms were stored on potato dextrose agar slants and in 50% glycerol solution at −70° C. For short-term storage, stock cultures were stored on agar slants at 4° C. The cultures of yeasts were sub-cultured onto Sabouraud dextrose (SAB) agar and incubated for 24 hours at 35° C. (*Candida albicans*) or for 48 hours at 25° C. (*Cryptococcus humicolus*) to obtain a freshly grown pure culture. The cultures of moulds were sub-cultured onto potato dextrose agar and incubated for 7 days at 35° C. (*Aspergillus niger*) or for 2 days at 35° C. then 5 days at 25° C. (*Fusarium oxysporum*) to ensure maximum sporulation.

Inoculum Preparation.

For yeasts, starting inoculum was prepared by suspending colonies of cultures in sterile 0.85% saline. The resulting suspension was vortexed and adjusted with a spectrophotometer at 530 nm to match the turbidity of 0.5 McFarland (1×106 to 5×106 CFU/mL). The stock yeast suspension was diluted 1:1000 with medium to obtain the two times test inoculum (1×103 to 5×103 CFU/mL).

For moulds, the stock suspensions were prepared by covering the mature fungal colonies with sterile 0.85% saline and scraping gently. 1% (v/v) of the wetting agent Tween 20 was added to the saline for the preparation of *Aspergillus* inoculum. Finally, the suspensions were vortexed for 15 s to break up clumps of cells and then filtered through four layers of sterile gauze. The densities of conidial spore suspensions was measured at 530 nm and adjusted to 0.09-0.11 for *Aspergillus niger* and 0.15-0.17 for *Fusarium oxysporum*. These suspensions were diluted 1:50 with the standard medium. The 1:50 inoculum dilutions corresponded to 2× the density needed of approximately 0.4×104 to 5×104 CFU/mL.

Inoculum quantitation was performed by plating dilution of the inoculum on Sabouraud dextrose agar to determine the viable number of CFU per milliliter.

Microdilution Technique.

Sterile 96-well flat-bottomed microtitration plates were used for testing. 100 µl of diluted inocula were dispensed into each microdilution well containing 100 µl of the double dilutions of compounds. Drug-free and yeast/mould-free controls were included. Microdilution trays were incubated at 35° C. (*Candida albicans* and moulds) or 25° C. (*Cryptococcus humicolus*) without agitation and observed for the presence or absence of visible growth. A numerical score from 0 to 4 was given to each well using the following scale: 0=optically clear or absence of growth, 1=slight growth (25% of growth control), 2=prominent reduction in growth (50% of growth control), 3=slight reduction in growth (75% of growth control), 4=no reduction in growth. Minimal inhibitory concentrations (MICs) were read at 48 hours.

The MICs for each of the compounds tested were defined as the lowest concentration of antifungal agents that prevent any visible growth of the organism (growth score=0). To elucidate the slight differences between agents in some cases the MIC's for moulds were additionally defined as the lowest concentrations with a growth score=1 (25% of growth control). The results are shown in Table 5 below.

TABLE 5

Antifungal activity of compounds

| | MIC µg/mL* | | | |
|---|---|---|---|---|
| Compound | Candida albicans ATCC 14053 | Cryptococcus humicolus ATCC 9949 | Aspergillus niger ATCC 16404 | Fusarium oxysporum VKM F-140 |
| AmB | 1 | 1 | 1 | 4 |
| S44HP | 1 | 1 | 1 | 4 |
| 1 | 1 | 1 | 1 | 2 |
| 5 | 2 | 4 | 4 | 4 |
| 6 | 2 | 2 | 4 | 4 |
| 7 | 2 | 1 | 2 | 8 |
| 8 | 2 | 2 | 4 | 8 |
| 9 | 1 | 1 | 2 | 4 |
| 10 | 2 | 2 | 4 | 8 |
| 11 | 1 | 1 | 2 | 2 |
| 12 | 1 | 1 | 2 | 2 |
| 13 | 1 | 1 | 1 | 4 |
| 14 | 1 | 1 | 2 | 4 |
| 15 | 1 | 2 | 2 | 4 |
| 16 | 1 | 1 | 2 | 8 |
| 17 | 1 | 1 | 2 | 8 |
| 18 | 1 | 1 | 2 | 8 |
| 19 | 2 | 2 | 2 | 8 |
| 20 | 2 | 2 | 4 | >16 |
| 21 | 2 | 4 | 4 | 4 |
| 22 | 1 | 1 | 1 | 1 |
| 23 | 4 | 4 | 8 | 8 |

*MICs are measured as the lowest concentrations of agents that prevent any visible growth. The results of the experiments were reproducible. In cases of full coincidence of the data obtained the MIC is represented as a single number.

The results show that the compounds of the invention have anti-fungal activity. More specifically these tests suggest that a number of nystatin derivatives have comparable anti-fungal activity to Amphotericin B and S44HP (e.g. compound nos. 1, 9, 11, 12, 13, 14 and 22).

Antifungal Susceptibility Study (2)

The anti-fungal activity of several of the nystatin derivatives was further investigated. The method used in study (1) is the Internationally accepted method for testing anti-fungal activity, but it is not very sensitive so does not readily distinguish between compounds of comparable activity. The anti-fungal activity of a number of the nystatin derivatives was therefore determined in a method which is designed to be more sensitive.

The test organism used for the further testing of polyene macrolide bioactivity was *Candida albicans* ATCC 10231, grown in 120 µl of standard M19 medium without NaCl (with an inoculum of 1000 cfu per well) and 30 µl of diluted polyene macrolide samples. The antibiotics were diluted in MeOH in series ensuring a spectrum of concentrations which yielded results ranging from complete growth inhibition to no inhibition of the test organism. The test organism cultures with antibiotic dilutions were incubated in 96-well microtiter plates at 30° C. without shaking, and growth was measured as $OD_{490}$ after 12, 14 and 16 hours on a SpectraMax Plus microtiter plate reader. OD was plotted against antibiotic concentration, and $MIC_{50}$ was estimated from the regression curve at 50% growth inhibition.

The results are shown in Table 6 below.

TABLE 6

| Compound | $MIC_{50}$ (µg/mL) |
| --- | --- |
| AmB | 0.12 |
| S44HP | 0.12 |
| 1 | 0.07 |
| 9 | 0.13 |
| 11 | 0.12 |
| 12 | 0.14 |
| 15 | 0.20 |
| 22 | 0.07 |

The results confirm that a number of nystatin analogues of the invention actually have improved anti-fungal activity compared to both amphotericin B and S44HP.

Antifungal Activities of Compound 1 Salts (Table 7)
The following water soluble salt are tested
COMPOUND 1 hydrochloride (53),
COMPOUND 1 L-glutamate (29),
COMPOUND 1 D-glutamate (54)
COMPOUND 1 L-aspartate (55),
COMPOUND 1 dichloroacetate (57)

TABLE 7

| | Compound No./MIC (µg/ml) | | | | | | |
| --- | --- | --- | --- | --- | --- | --- | --- |
| Organism | 55 | 29 | 53 | 54 | 57 | 1 | S44HP |
| *Candida albicans* ATCC 14053 | 2 | 1 | 2 | 2 | 2 | 1 | 1 |
| *Cryptococcus humicolus* ATCC 9949 | 2 | 1 | 2 | 2 | 2 | 1 | 1 |

TABLE 7-continued

| | Compound No./MIC (µg/ml) | | | | | | |
| --- | --- | --- | --- | --- | --- | --- | --- |
| Organism | 55 | 29 | 53 | 54 | 57 | 1 | S44HP |
| *Aspergillus niger* ATCC 16404 | 2 | 2 | 4 | 2 | 2 | 2 | 1 |
| *Fusarium oxysporum* VKM F-140 | 2 | 2 | 4 | 2 | 2 | 2 | 4 |

Compound 1 L-glutamate (29) is the most active salt of Compound 1,

Antifungal Activities of Compound Derivatives (Tables 8 and 9)

TABLE 8

| Comp 50 | p-Dimethylaminobenzyl-Compound 1 | | |
| --- | --- | --- | --- |
| Comp 51 | N-(L-Lysyl)-Compound 1 | | |
| | MIC (µg/ml) | | |
| Organism | Comp 50 | Comp 51 | Comp 1 |
| *Candida albicans* ATCC 14053 | 2 | 1 | 1 |
| *Cryptococcus humicolus* ATCC 9949 | 2 | 1 | 1 |
| *Aspergillus niger* ATCC 16404 | 2 | 1 | 2 |
| *Fusarium oxysporum* VKM F-140 | 8 | 2 | 2 |

Compound 51 is the most active derivative in this series with antifungal activity slightly higher than the parent antibiotic.

TABLE 9

| | Compound No./MIC (µg/ml) | | | | | | | | | | | | | | | | | | | |
| --- | --- | --- | --- | --- | --- | --- | --- | --- | --- | --- | --- | --- | --- | --- | --- | --- | --- | --- | --- | --- |
| Organism | 32 | 37 | 43 | 30 | 36 | 41 | 39 | 45 | 34 | 38 | 44 | 35 | 40 | 46 | 47 | 33 | 48 | 31 | 42 | S44HP |
| *Candida albicans* ATCC 14053 | 2 | 2 | 1 | 1 | 4 | 0.5 | 1 | 1 | 1 | 1 | 1 | 2 | 2 | 2 | 2 | 1 | 0.5 | 1 | 0.5 | 1 |
| *Cryptococcus humicolus* ATCC 9949 | 2 | 1 | 1 | 1 | 4 | 1 | 1 | 2 | 2 | 1 | 2 | 2 | 2 | 2 | 2 | 1 | 0.5 | 2 | 1 | 1 |
| *Aspergillus niger* ATCC 16404 | 2 | 2 | 1 | 1 | 4 | 1 | 2 | 1 | 1 | 2 | 2 | 4 | 4 | 2 | 4 | 1 | 1 | 2 | 1 | 1 |
| *Fusarium oxysporum* VKMF-140 | 8 | 4 | 4 | 4 | 16 | 2 | 16 | 4 | 4 | 4 | 4 | 4 | 16 | 4 | 16 | 2 | 1 | 4 | 2 | 4 |

In Vitro Toxicity Study

The toxicity of various nystatin derivatives was tested at 2 and 5 µg/mL and at 25 µM.

Compounds were dissolved in DMSO at 5 mg/mL and 0.1 mL samples with different concentrations were prepared in DMSO. The samples were mixed with 0.9 mL PBS buffer containing 2.5% horse blood (PBS-HB; kept on ice) and incubated at 37° C. for 30 min without agitation.

Cells were pelleted by centrifugation at 5000 rpm for 5 min and haemolysis was evaluated by measuring $OD_{545}$. 100% haemolysis was defined as the $OD_{545}$ value obtained from a suspension of 2.5% horse blood in distilled water.

The results are shown in Tables 10-12 below.

TABLE 10

Haemolysis of human blood erythrocytes (M ± SE, %) under the action of 2 and 5 μg/mL of antibiotics.

| Blood sample # | Conc. μg/mL | Amp B | S44HP | 13 | 14 | 16 | DMSO |
|---|---|---|---|---|---|---|---|
| 1 | 5 | 30 | 34.6 | 15.5 | 4.8 | 3.1 | 2.2 |
| 2 | | 29.5 | 39.7 | 14 | 4.5 | 2.9 | 1.7 |
| 3 | | 31.5 | 50.4 | 14.2 | 5.3 | 3.4 | 1.4 |
| MEAN ± SE | | 30.3 ± 0.6 | 41.6 ± 4.6 | 14.5 ± 0.5 | 4.9 ± 0.2 | 3.1 ± 0.14 | 1.7 ± 0.2 |
| 1 | 2 | 4.4 | 12.3 | 3.3 | 2.7 | | 2.3 |
| 2 | | 5.9 | 6.4 | 3.0 | 2.5 | | 2.2 |
| 3 | | 8.0 | 7.5 | 4.9 | 2.5 | | 2.6 |
| MEAN ± SE | | 6.1 ± 1.0 | 8.7 ± 1.8 | 3.7 ± 0.6 | 2.5 ± 0.07 | 2.4 ± 0.12 | |

TABLE 11

Haemolysis of erythrocytes (M ± SEM, %) under the action of 5 μg/mL of antibiotics.

| Blood sample # | Amp B | S44HP (92%) | 7 | 15 | 11 | 12 | DMSO |
|---|---|---|---|---|---|---|---|
| 1 | 39 | 73 | 5.8 | 2.8 | 3 | 5 | 1.4 |
| 2 | 38 | 64 | 5.0 | 2.4 | 3.4 | 4.3 | 2.2 |
| 3 | 42 | 56 | 5.0 | 2.7 | 3.3 | 4.0 | 1.5 |
| Mean ± SE | 39.7 ± 1.2 | 64.3 ± 4.9 | 5.2 ± 0.2 | 2.6 ± 0.1 | 3.2 ± 0.1 | 4.4 ± 0.3 | 1.7 ± 0.25 |

TABLE 12

Haemolysis of erythrocytes (M ± SEM, %) under the action of 25 μM of antibiotics.

| Blood sample # | 5 | 6 | 7 | 9 | 17 | 18 |
|---|---|---|---|---|---|---|
| | 2 | 2 | 0.9 | | | |
| | 1.8 | 2.4 | | | | |
| | 2.1 | 3.3 | 1.9 | | | |
| | 1.0 | 7 | 1.9 | 12.2 | | |
| | 1 | 3.7 | 1.7 | 18.0 | 1.7 | 3.0 |
| | 1.9 | 4.3 | 1.3 | 16.7 | 1.7 | 3.2 |
| | | | 1.9 | 22.4 | 2.1 | 9.7 |
| | 1.3 | 3.2 | 1.0 | 25 | 0.8 | 1.0 |
| | | | | 16.2 | 3.3 | 1.5 |
| Mean ± S.E.M. | 1.6 ± 0.2 | 3.7 ± 0.6 | 1.5 ± 0.17 | 18.4 ± 1.9 | 2.4 ± 0.6 | 3.9 ± 1.3 |
| N | 7 | 7 | 7 | 6 | 6 | 6 |
| P | <0.001 | <0.01 | <0.001 | <0.001 | <0.001 | <0.05 |

These results show that the compounds of the invention are significantly less toxic that S44HP or Amphotericin B. This is highly advantageous since the compounds of the invention can therefore be used in higher amounts without adverse effect.

In Vivo Testing of Compounds 1 and 11 et al

Animals.

Male mice of hybrids of first generation (C57B1/6xDBA/2)F1 B6D2F1, weight 20-22 g., received from the Central farm. "Kryukovo" of Russian Academies of Medical Science (RAMS) were used. Animals were maintained in a vivarium in plastic cages (with hardwood bedding in environmentally controlled conditions: 24±1° C., 12/12 hours light/dark cycle) on a standard diet of bricketed forages with easy access to drinking water (ad libitum). After a 2-week quarantine period, healthy animals were used in experimental work.

Infectious Agent.

*Candida albicans* (strain 14053 ATCC) was used.

Antifungal Agents.

Solutions of compounds 1 and 11 (et al) were prepared "ex temporae" and were kept in dark glass vials to avoid ingress of light. The solutions were prepared as follows: dry antibiotic substances (5 mg) were mixed with dry sodium deoxycholate (4.1 mg) in a sterile glass vial. 10 mL of phosphate buffer ($NaH_2PO_4$—1.59 g; $Na_2HPO_4$—0.96 g; $H_2O$—to 100 mL) was added to the mix and the suspension was immediately subjected to vigorous shaking for 10 minutes until homogeneous suspensions were formed. The obtained suspensions (2 mL) were placed into the new sterile glass vials, 6 mL of 5% neutral sterile glucose solution was added, and the resulting solutions (0.125 mg/mL) were used for intravenous administration.

Preparations of amphotericin B and S44HP were also prepared in the same way.

Acute Toxicity

The acute toxicity of compounds 1 and 11 (et al), as well as amphotericin B and S44HP was determined.

The antibiotic preparations were singly injected into the mice's tail vein within 1-1.5 hours after the preparation of solutions. The speed of injection did not exceed 0.5 mL per minute. Each antibiotic was used in a range of doses resulting in 0% to 100% lethality and a minimum of 3 intermediate doses. Animals were randomized into groups, each containing 6 mice. Toxicity-characterizing doses MTD and $LD_{50}$ were calculated with the method of "probit analysis" according to Litchfield-Wilcoxon (J Pharmacol Exp Ther 96:99) by statistical analysis program "StatPlus-3.5.0.—2005". The results are shown in Table 13 below.

TABLE 13

Acute Toxicity

| Compound | $LD_{50}$ (mg/kg) | MTD (mg/kg) |
|---|---|---|
| Amphotericin B | 2.8 | 2.01 |
| S44HP | 2.05 | 0.64 |
| 1 | 15.4 | 7.8 |
| 11 | 16.4 | 11.9 |
| 29 | 17.8 | 11.0 |
| 51 | 5.3 | 4.48 |
| 41 | 38.6 | 21.2 |
| 48 | 32.2 | 25.9 |
| 25 | 50.8 | 42.8 |
| 26 | 50.0 | 43.1 | venously administered (in the same volume as antifungal agent preparations) 0.2 mL of solvent (phosphatic buffer +5% glucose (1:1)).

No activity was identified on any of the "placebo" group. Also *Candida albicans* was never found out in not infected animals.

On the 5th day of experiment, mice were weighed and euthanized (killed) by a cervical dislocation. Then, in sterile conditions, the *Candida albicans* burden of each mouse was determined by counting of viable homogenates from the kidneys. The kidneys were removed aseptically and weighed, then pounded in porcelain mortars with sterile corundum. Dilutions of the resulting suspensions were prepared and sowed on Petri dishes with agar Saburo, incubated for 24 hours at a temperature of 35° C. Developed colonies of *Candida albicans* were then counted and their quantity calculated on the basis of 1 g of kidney tissue.

Statistical analysis was carried out with Microsoft Office Excel 2003. Significant distinctions had a $P \leq 0.05$ at comparison by Student t-criterion.

Figure 9:
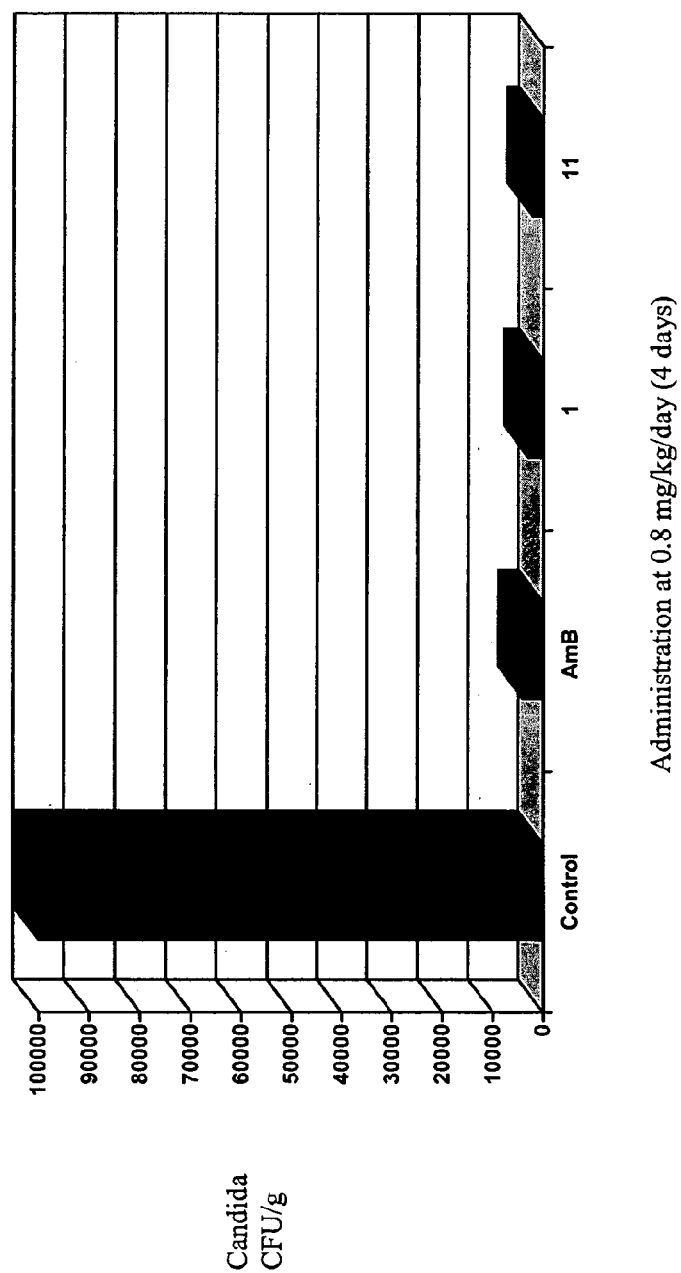
FIG. 9 shows the results of in vivo antifungal activity testing on compounds 1 and 11.
Figure 10:
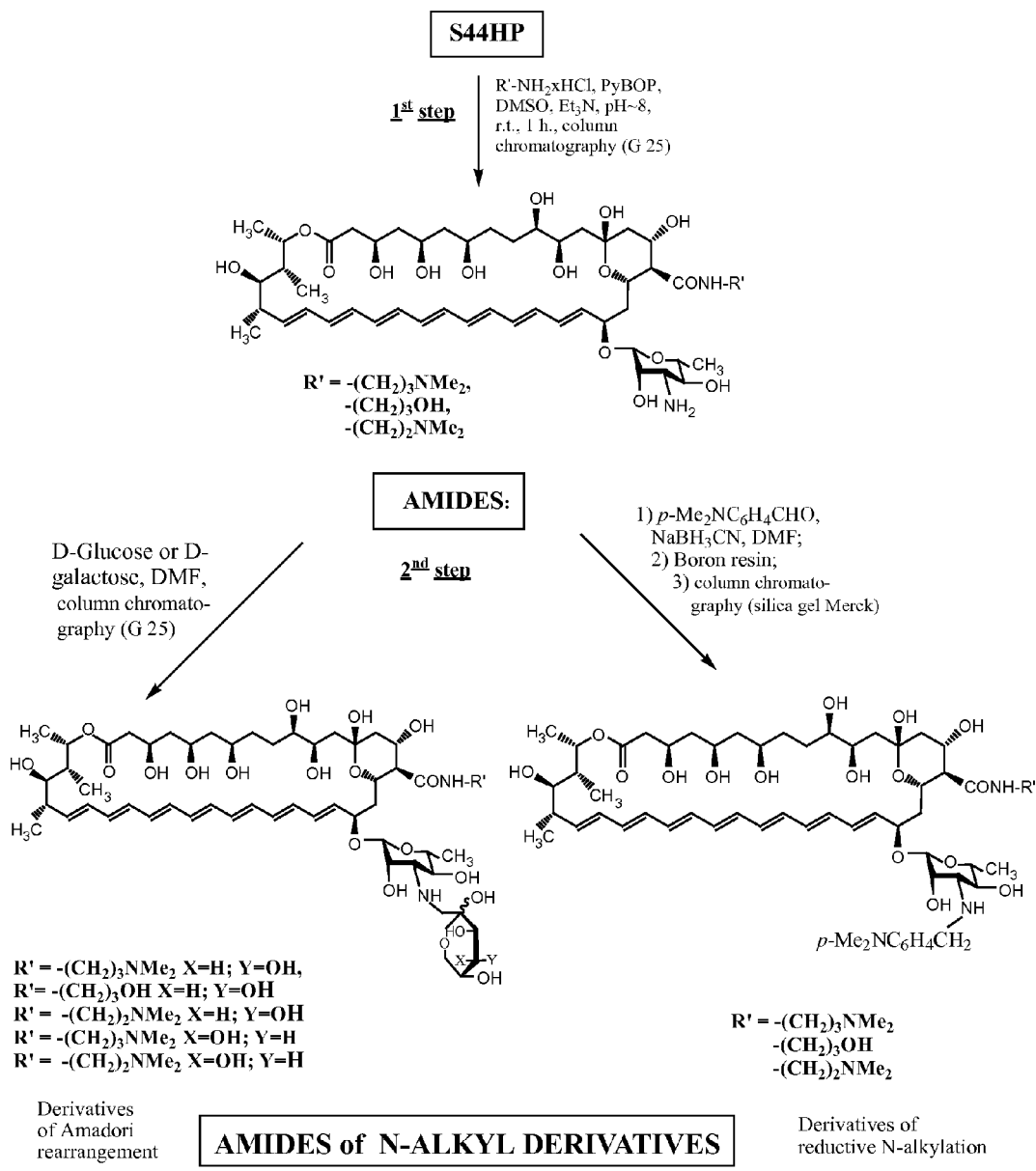
FIG. 10 shows scheme 1, a scheme for the preparation of Amides of N-Alkyl derivatives of a compound of the disclosure.

The results are shown in Table 14 below and in FIG. 9.

TABLE 14

| | Dose | | | |
|---|---|---|---|---|
| Compound | 5 mg/kg × 4/24 | 2.5 mg/kg × 4/24 | 0.8 mg/kg × 4/24 | 0.08 mg/kg × 4/24 |
| | | Number of Colonies | | |
| untreated | $1.2 \times 10^5$ | $1.0 \times 10^5$ | $4.5 \times 10^4$ | $6.0 \times 10^4$ |
| | $5.0 \times 10^4$ | $4.0 \times 10^4$ | $5.0 \times 10^4$ | $2.5 \times 10^5$ |
| | $4.0 \times 10^4$ | $6.0 \times 10^4$ | $1.0 \times 10^5$ | $5.0 \times 10^4$ |
| Amp B | — | $2.8 \times 10^2$ | $4 \times 10^3$ | $3.4 \times 10^4$ |
| | — | $1.0 \times 10^3$ | $2 \times 10^3$ | $1.8 \times 10^4$ |
| | — | $2.2 \times 10^2$ | $6 \times 10^3$ | $2.6 \times 10^4$ |
| 1 | $1.0 \times 10^1$ | $2.0 \times 10^1$ | $2.5 \times 10^3$ | $2.4 \times 10^4$ |
| | 0 | $1.0 \times 10^1$ | $1.2 \times 10^3$ | $2.8 \times 10^4$ |
| | $1.0 \times 10^1$ | $2.0 \times 10^1$ | $5.0 \times 10^3$ | $2.4 \times 10^4$ |
| 11 | 0 | $<10^1$ | $1.2 \times 10^3$ | $3.0 \times 10^4$ |
| | 0 | $1.0 \times 10^1$ | $3.0 \times 10^3$ | $2.7 \times 10^4$ |
| | $<10^1$ | $1.0 \times 10^1$ | $2.5 \times 10^3$ | $1.5 \times 10^4$ |

| | Dose of S44HP | | | |
|---|---|---|---|---|
| | 0.6 mg/kg × 4/24 | 0.3 mg/kg × 4/24 | 0.15 mg/kg × 4/24 | 0.08 mg/kg × 4/24 |
| | | Number of Colonies | | |
| S44HP | $2.5 \times 10^3$ | $2.7 \times 10^3$ | $8.0 \times 10^3$ | $2.7 \times 10^4$ |
| | $8.8 \times 10^3$ | $9.4 \times 10^3$ | $6.4 \times 10^3$ | $8.0 \times 10^4$ |
| | $1.2 \times 10^3$ | $1.3 \times 10^4$ | $1.6 \times 10^4$ | $8.2 \times 10^4$ |

TABLE 13-continued

Acute Toxicity

| Compound | $LD_{50}$ (mg/kg) | MTD (mg/kg) |
|---|---|---|
| 27 | 20.6 | 10.8 |
| 28 | 22.1 | 14.7 |

In Vivo Antifungal Activity

Animals were infected intravenously with *Candida albicans* culture at a dose of 1.0 million CFU/mouse (volume 0.1 mL). 30 minutes after infection, the antifungal agents were introduced intravenously into the mice at various doses in a volume of 0.2 mL (at a rate of 0.2 mL/30 second). Each dose was administered daily for four days including the day of infection (0, 1, 2 and 3 days).

As a control, there was a group of untreated mice (infected in the same way with *Candida albicans*). Also there was a "placebo" group of non-infected animals which were intra- Study of Specific Activity of Compound 29, 51, 41, 48 on Model of the Candidiasis Sepsis of Mice Animals.

In experiments used female mice of hybrids of first generation (C57B1/6xDBA/2)F1 (B6D2F1), weight 18-20 g., received from the Central farm "Kryukovo" of Russian Academies of Medical Science (RAMS). Animals were maintained in Institute' vivarium in plastic cages (with hardwood bedding in environmentally controlled room: 24±1° C., 12/12 hours light/dark cycle) on a standard diet of bricketed forages with an easy approach to drinking water (ad libitum). After 2-week quarantine healthy animals were used in experimental work.

As the infectious agent used *Candida albicans* (strain 14053 ATCC). Tested preparations were Compounds 29, 51, 41, 48. A preparation of comparison was amphotericin B (pure). Solutions of tested preparations prepared ex tempore by the technique specified by the customer.

Statement of Experiment

Animals were housed on 3 mice and infected intravenously with culture *Candida albicans* in a doze 1.0 million CFU/mouse in volume of 0.1 ml. It is necessary to note, that doze *Candida albicans* remained a constant in all experiments. In 30 minutes after infection to mice carried out the first intravenous introduction of tested preparations in corresponding dozes in volume of 0.2 ml (with a speed of 0.2 ml/30 second).

Experiment has been planned in such a manner that in each experiment one doze (both for amphotericin B was used, and for tested preparations), each doze entered daily within four days, since day of infection (0, 1, 2 and 3 days). At each experiment there was a group untreated, infected with *Candida albicans* animals. Also there was a group "placebo", intact (not infected) animals, which intravenously (in the same volume as medical preparations) injected 0.2 ml of solvent—phosphatic buffer +5% glucose (1:1). Data on activity of the "placebo" have not shown any activity. *Candida albicans* was never found out in not infected animals.

On the post challenge 5th day of experiment, mice were weighed and euthanized (killed) by a cervical dislocation.

Then, in sterile conditions, *Candida albicans* burdens were determined by viable counting of homogenates from the kidneys. The kidneys, which were removed aseptically and weighed, pounded in porcelain mortars with sterile corundum, did dilutions of the received suspensions and sowed on Petri dishes with agar Saburo, incubated for 48 hours at temperature 35° C., then counted up developed colonies *Candida albicans* and recalculated their quantity on 1 g of kidney' tissue. The first dilution was $10^{-1}$. Zero result at this cultivation accepted for 5 CFU/g.

For the basic criterion of an assessment of the investigated preparations the maximal effect of the Amphotricin B was accepted (effective dose, ED).

Statistical processing carried out with the help of computer program Microsoft Office Excel 2003. For significant accepted distinctions of average at $P \leq 0.05$ at comparison by Student t-criterion.

The received results are presented in table 15. Amphotericin B has shown the maximal activity, accepted for criterion of activity, in highest of its studied dozes (1.25 mg/kg/d, ≈62% from MTD).

TABLE 1

Activity of Compounds 29, 51, 41, 48 in comparison with Amphotericin B (pure) on model of the candidiasis sepsis of mice.

| Drug | n | 0 | 0.08 | 0.16 | 0.31 | 0.62 | 1.25 | 2.5 | 5 | 10 |
|---|---|---|---|---|---|---|---|---|---|---|
| untreated | 24 | 99042 ± 15255 | | | | | | | | |
| AMF | 3 | | 105000 ± 48563 | 85667 ± 9770 | 34667 ± 12914 | 10667 ± 4807 | 1667 ± 441* | | | |
| 29 | 3 | | | 102667 ± 58769 | | 12500 ± 6614* | 2557 ± 1281* | 133 ± 33* | 5 ± 1* | |
| 51 | 3 | | 56667 ± 22040 | | 22667 ± 3844* | 17833 ± 9011* | 9400 ± 6416* | 5 ± 1* | | |
| 41 | 3 | | | 67000 ± 8622 | | 22667 ± 2906* | 2767 ± 1974* | 1667 ± 1167* | 5 ± 1* | |
| 48 | 3 | | | 51667 ± 25221 | | 3233 ± 888* | 1487 ± 417* | 63 ± 19* | 5 ± 1* | |

Notes:
*significant difference from untreated/Dataq presented as Mean ± standard error. n—number of the mice/

Synthesis of Further Compounds Based on Genetic Manipulation

Various further manipulable backbone structures have been prepared. Using the chemistry above, various different functional groups can be attached to the free COOH and amine groups. These base structures all form further preferred compounds of the invention. (H atoms are not shown)

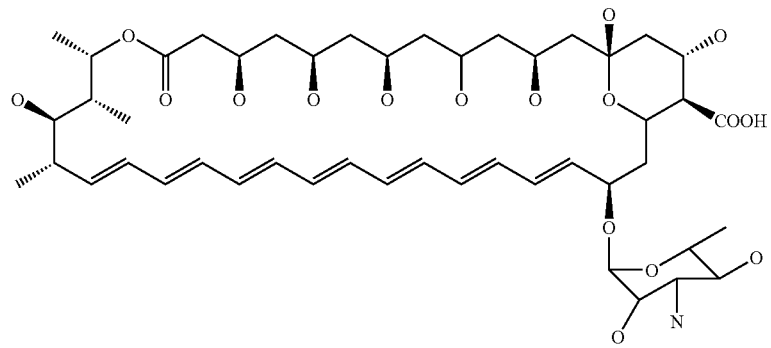

B1

Inactivation of ER5 and DH15 Domains in Nystatin PKS, No C-10 Hydroxylation
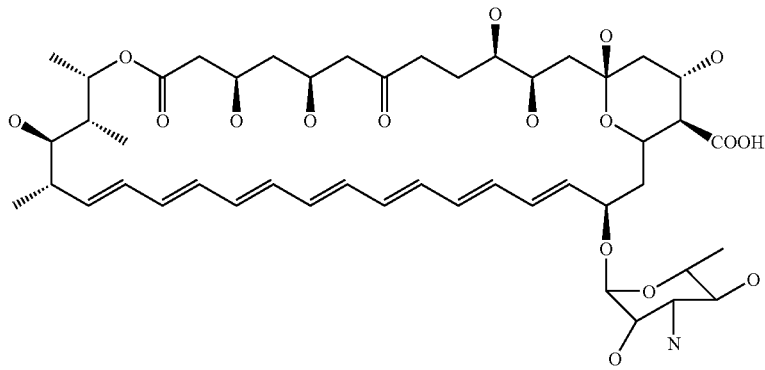
B2
Inactivation of ER5 and KR16 Domains in Nystatin PKS
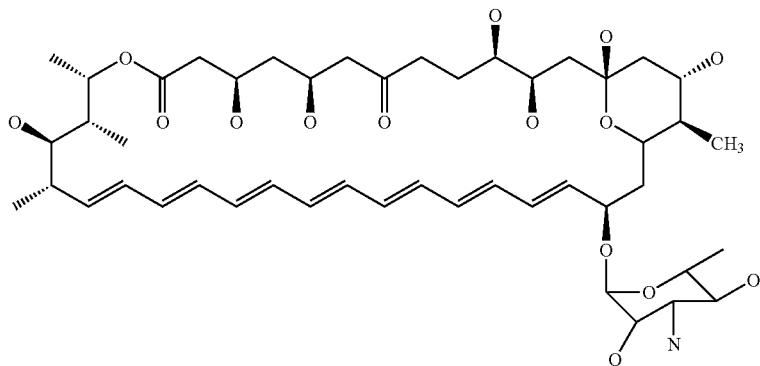
B3
Inactivation of ER5, DH15 Domains in Nystatin PKS and NysN Monooxygenase, No C-10 Hydroxylation
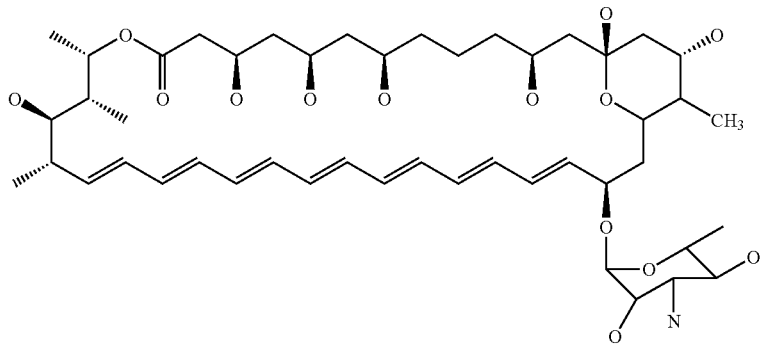
B4

Inactivation of ER5 Domain in Nystatin PKS and NysN and NysL Monooxygenases

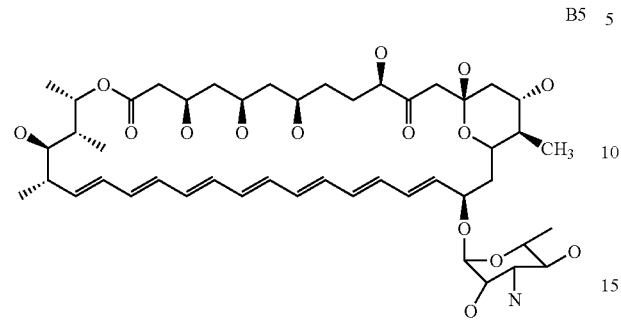

Inactivation of ER5 and KR14 Domains in Nystatin PKS and NysN Monooxygenase.

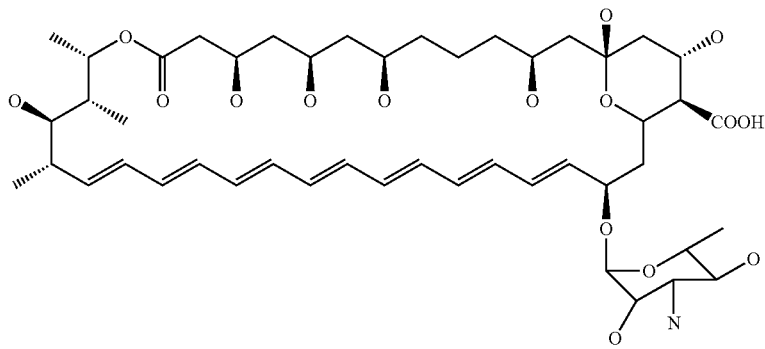

Inactivation of ER5 Domain in Nystatin PKS and NysL Monooxygenase.

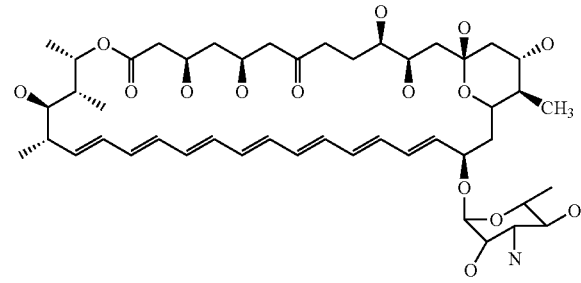

Inactivation of ER5 and KR16 Domains in Nystatin PKS and NysN Monooxygenase
Construction of Mutant B2
Construction of Gene Replacement Vector for KR16 Inactivation The entire 14 kb insert of recombinant phage N20 (Brautaset et al., 2000) was excised by XbaI and cloned into plasmid pGEM-3zf, yielding pL20X. From this plasmid, the 3.7 kb BamHI fragment was excised and ligated into pGEM-3zf, resulting in plasmid pGEMB3.7. A 0.8 kb DNA fragment (including the KR16 active site residue Y3404) was then PCR amplified from pGEMB3.7 by using the following primers:

```
                                      (SEQ ID NO: 15)
KR16-F1: 5'-ttttctgCAGCCGACCGGCACCGTCC-3'
(sense),
and (SEQ ID NO: 16)
KR16-1R: 5'-ttttaaGCTTCCTGGACCGCGCGGG-3'
(antisense)
```

The PCR product was end-digested with PstI and HindIII (new recognition sites underlined in the two PCR primers), and cloned into the corresponding sites of pLITMUS28, yielding pLITPH0.8. The latter plasmid served as a template for site-directed mutagenesis of the KR16 active site by using the following mutagenic oligonucleotides:

```
mutKR16-1F:
                                      (SEQ ID NO: 17)
5'-CCCCGGCCAGGCCGGCTTCGAAGCCGCCAACGCGGTCC-3'
(sense)

mutKR16-1R:
                                      (SEQ ID NO: 18)
5'-GGACCGCGTTGGCGGCTTCGAAGCCGGCCTGGCCGGGG-3'
(antisense)
```

Mutated nucleotides are shown in bold and the new BstBI recognition site introduced is underlined. By using these two oligonucleotides the KR16 active site Tyr is substituted into Phe and simultaneously the next downstream Ala is substituted with Glu, yielding double mutation YA3404FE. A plasmid with the correct mutation was identified with BstBI digestion and the entire cloned insert was sequenced to unravel any other undesired mutations. From the correctly mutated plasmid the 627 bp Bpu102I/Bpu10I fragment was excised and used to substitute for the corresponding fragment of plasmid pGEMB3.7, yielding plasmid pGEMB3.7 m. From the latter plasmid, the entire 3.7 kb insert was excised with EcoRI/HindIII and ligated together with the 3.1 kb EcoRI/HindIII backbone of pSOK201, yielding gene replacement vector pKR16 m.
Gene Replacement The latter vector was introduced into the nysA-deficient S. noursei mutant GG5073SP (Borgos et al., 2006) by double homologous recombination. The correct chromosomal KR16 mutation was verified by using PCR+BstBI digestion as well as Southern blot, before polyene production was restored by introducing the nysA gene in trans as described elsewhere (Brautaset et al., 2003). The resulting mutant was designated B2.

Construction of Mutant B7

Plasmid pKOnysN-CL346AS (see PNAS-manus) was introduced into the nysA-deficient B2 by double homologous recombination. The correct chromosomal nysN mutation was verified by using PCR and NheI digestion as well as Southern blot, before polyene production was restored by introducing the nysA gene in trans as described elsewhere (Brautaset et al., 2003). The resulting mutant was designated B7.

Construction of Mutant B5

Construction of Gene Replacement Vector for KR14 Inactivation:

The 4.0 BclI/EcoRI fragment of plasmid pL20X (see strategy B2, above) was excised and ligated into pGEM-3zf digested with BamHI/EcoRI, yielding pBE4.0. A 1 kb fragment was PCR amplified from the latter plasmid by using the following primers:

```
                                         (SEQ ID NO: 19)
    KR14-F1: 5'-TTCGGCGGCGTAATCTCC-3' (sense),
    and (SEQ ID NO: 20)
    KR14-R1: 5'-ttttaaGCTTCCACGGCGAGGTGC-3'
    (antisense)
```

The PCR fragment was digested with SacI and HindIII (new recognition site is underlined in the primer) and ligated into pLITMUS28, yielding pLITHS1.0, and the latter plasmid was used as a template for site-directed mutagenesis of the KR14 active site by using the following mutagenic oligonucleotides:

```
KR14-mut1:
                                         (SEQ ID NO: 21)
5'-CCCGGGCCAGGCCAACTTCGAAGCTGCCAACGCCGTC
CTG-3' (sense), KR14-mut2:
                                         (SEQ ID NO: 22)
5'-CAGGACGGCGTTGGCAGCTTCGAAGTTGGCCTGGCCC
GGG-3' (antisense)
```

Mutated nucleotides are shown in bold and the new BstBI recognition site introduced is underlined. By using these two oligonucleotides the KR14 active site Tyr is substituted into Phe and simultaneously the next downstream Ala is substituted with Glu, yielding double mutation YA9197FE. A plasmid with the correct mutation was identified with BstBI digestion and the entire cloned insert was sequenced to unravel any other undesired mutations. From the correctly mutated plasmid the 0.7 kb FseI/AscI fragment was excised and used to substitute for the corresponding fragment of plasmid pBE4.0, yielding pBE4.0mut. From the latter plasmid, the entire 4.0 kb insert was excised with EcoRI/HindIII and ligated together with the 3.1 kb EcoRI/HindIII backbone of pSOK201, yielding gene replacement vector pKR14 m.

Gene Replacements

The latter vector was introduced into the nysA-deficient S. noursei mutant GG5073SP (Borgos et al., 2006) by double homologous recombination. The correct chromosomal KR14 mutation was verified by using PCR+BstBI digestion as well as Southern blot, before polyene production was restored by introducing the nysA gene in trans as described elsewhere (Brautaset et al., 2003). The resulting mutant was designated BSG015.

Next, the nysN inactivation vector pKOnysN-CL346AS (see PNAS-manus) was introduced into the nysA-deficient BSG015 by double homologous recombination. The correct chromosomal nysN mutation was verified by using PCR and NheI digestion as well as Southern blot, before polyene production was restored by introducing the nysA gene in trans as described elsewhere (Brautaset et al., 2003). The resulting mutant was designated B5.

Construction of Mutant B4

Construction of Gene Replacement Vector for nysL Inactivation.

The nysL gene replacement in-frame deletion plasmid pNLD1 has been described (Volokhan et al., 2006), and the 4.2 kb cloned insert of this plasmid includes regions of the S. noursei nysN coding region. In order to introduce the nysL mutation into a nysN-CL346ST mutant background, we had to modify this plasmid to include this nysN mutation as well. This was done as follows: The 1011 bp AgeI/FspaI fragment of plasmid pSOK201 nysN4.1-CL346ST (see Biosergen patent application May 2007) was excised and used to substitute with the corresponding fragment of plasmid pNLD1, yielding gene replacement plasmid pNLD2.

Gene Replacement:

Plasmid pNLD2 was introduced into the nysA-deficient Compound 1 by double homologous recombination. The correct chromosomal nysL mutation was verified by using PCR and NheI digestion as well as Southern blot, before polyene production was restored by introducing the nysA gene in trans as described elsewhere (Brautaset et al., 2003). The resulting mutant was designated B4.

B1 and B3

Inactivation of DH15 Active Site His966 of NysJ:

Aim: Introduce a Site-Specific Mutation into the nysJ DH15 Active Site Leading to Substitution Mutation H966F in the DH15 Domain Procedure:
  Digest pL20X with BclI+SphI and clone 3.33 kb fragment into pGEM11-zf digested with BamHI/SphI=pDH15-A
  Digest pDH15-A with EcoRI+HindIII and clone 3.34 kb fragment into the corresponding sites pGEM3-zf=pDH15-B
  Perform site-directed mutagenesis using pDH15-B template and with the following mutagenic oligonucleotides:

```
Mut-DH15-1:
                                         (SEQ ID NO: 23)
5'-CACCCCTGGCTCGCCGACTTCGTCGTCGGCGGCATGGTC-3'

Mut-DH15-2:
                                         (SEQ ID NO: 24)
5'-GACCATGCCGCCGACGACGAAGTCGGCGAGCCAGGGGTG-3'
```

Mutated nucleotides are indicated in bold. The mutation destroys natural BtrI site in this position.
  Verify correct mutation with BrtI digestion and DNA sequencing=pDH15-Bmut.
  Isolate the 1.6 kb EcoRI/SacI fragment-1 of pDH15-B; The 1.1 kb HindIII/BglII fragment-2 from pDHI5-B, and the SacI/BglII fragment-3 from pDH15-Bmut, and ligate all three fragments together with the 3.1 kb pSOK201 EcoRI/HindIII backbone; pDH15-123
  Proceed with gene replacement into S. noursei.
  Verifications of correct S. noursei DH15 mutations
  1$^{st}$ crossover mutants can be verified by Southern blot after NotI digestion of total DNA and using the labelled 3.33 insert of pDH15-A as a probe. Wild type shall give 5.2+8 kb signals, while correct 1$^{st}$ crossover mutant (both theoretical variants) should give 5.2+6.4+8 kb signals.

2$^{nd}$ crossover mutants can be analysed by PCR using the following primers:

```
                                       (SEQ ID NO: 25)
    DH15-F: 5'-CCTTCCTCGAACTCGGCC-3'

(SEQ ID NO: 26)
    DH15-R: 5'-GCGTAGATCTCGGTGTCG-3'
``` which shall give 817 bp product. The PCR product from the parent strain can be digested with BtrI, giving 392 bp and 425 bp fragments, while the PCR product from the mutant can not be cut with BtrI. Additionally, the 2$^{nd}$ mutant can be also verified by Southern blot using labelled 817 bp PCR product as a probe. The parent's strain DNA digested with BtrI shall give 0.95 kb+0.45 kb hybridizing fragment, while BtrI-digested DNA from the mutant shall give one 1.4 kb hybridizing fragment.

Construction of Mutant B1

The DH15 mutation was introduced into the nysA-deficient GG5073SP strain, and the correct mutant was then complemented with the nysA gene in trans.

Construction of Mutants B3

The nysN-CL346ST mutation was introduced into the nysA-deficient B1-S1 genetic background, and the resulting correct mutant strain was complemented with the nysA gene in trans, yielding mutant B3-1S.

In Vivo Efficacy of Amphotericin B and Novel S44HP Analogues in a Neutropenic Mouse Model of Disseminated Candidosis Mice were rendered neutropenic by injection with cyclophosphamide monohydrate (Fluka, BioChemika, Sigma-Aldrich, Switzerland) intraperitoneally 2×100 mg/kg of body weight 1 day before infection.

Figure 17:
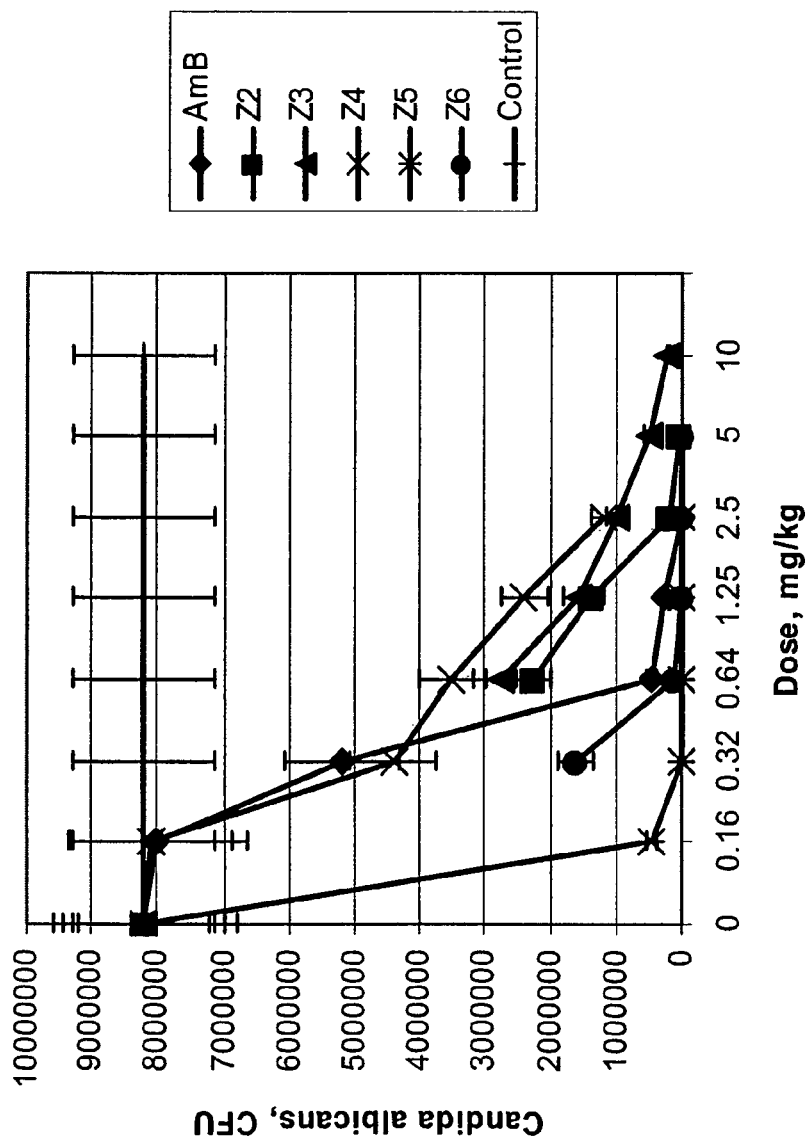
FIG. 17 shows the results of in vivo testing of novel compounds of the invention in a neutropenic mouse model of disseminated candidosis.

Disseminated infection with the *Candida albicans* was achieve by injection of 3×10$^5$ CFU/ml of inoculum via the lateral tail vein of neutropenic mice 2 h prior the start of antibiotic therapy. The efficacy of antibiotics in eliminating *C. albicans* infection was assessed by evaluation of fungal load in kidneys after 4 days treatment (1 dose per day). Results are presented in FIG. 17.

Amphotericin B was administered at the highest dose of 2 mg/kg (just below MTD).

These results clearly show that Compound 28 and compound 29 are considerably better than amphotericin B since:
1) They show ca 5-7 times lower acute toxicity;
2) They demonstrate 5-10 times better efficacy in treatment of disseminated candidosis in neutropenic mouse model;
3) They are soluble in 5% glucose (>10 mg/ml), while solubility of amphotericin B is <1 mg/ml.

Although compound 25 and compound 26 are less active than amphotericin B in the neutropenic mouse model of candidosis, they display much lower acute toxicity (ca 20 times lower than amphotericin B), and therefore are still considered interesting candidates.

The invention claimed is:

1. A compound of formula:

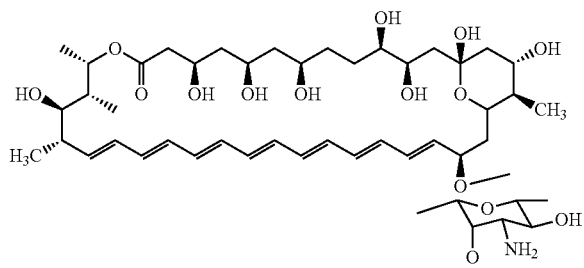

or a pharmaceutically acceptable salt thereof.

2. A compound as claimed in claim 1 in the form of a salt which is formed with a physiologically acceptable organic or inorganic acid selected from the group consisting of acetic, aspartic, benzenesulfonic, benzoic, bicarbonic, bisulfuric, bitartaric, butyric, calcium edetate, camsylic, carbonic, chlorobenzoic, citric, edetic, edisylic, estolic, esyl, esylic, formic, fumaric, gluceptic, gluconic, glutamic, glycollylarsanilic, hexamic, hexylresorcinoic, hydrabamic, hydrobromic, hydrochloric, hydroiodic, hydroxynaphthoic, isethionic, lactic, lactobionic, maleic, malic, malonic, mandelic, methanesulfonic, methylnitric, methylsulfuric, mucic, muconic, napsylic, nitric, oxalic, p-nitronnethanesulfonic, pamoic, pantothenic, phosphoric, monohydrogen phosphoric, dihydrogen phosphoric, phthalic, polygalactouronic, propionic, salicylic, stearic, succinic, sulfamic, sulfanilic, sulfonic, sulfuric, tannic, tartaric, teoclic and toluenesulfonic acid.

3. A compound as claimed in claim 1 in the form of a salt which is formed with a base selected from the group consisting of primary amine, secondary amine, tertiary amine, substituted amine, cyclic amine, arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resin, procaine, purine, theobromine, triethylamine, trimethylamine and tripropylamine.

4. A compound as claimed in claim 1 in the form of a glutamate salt.

5. A process for making a compound of claim 1, comprising:
 (i) modifying a gene cluster encoding the polyketide synthase system responsible for nystatin synthesis by inactivation of the ER domain in module 5 of polyketide synthase to produce a nystatin derivative having a double bond between C28 and C29; and
 (ii) additionally modifying said gene cluster by inactivation of P450 monooxygenase-encoding genes nysN to produce a nystatin derivative which is modified at C16, or
 (iii) modifying the resulting derivative at C16 by reductive alkylation.

6. A pharmaceutical composition comprising a compound as claimed in claim 1 and a carrier, a diluent or an excipient.

7. A method of treatment of a fungal infection in a human, comprising administering to a human a compound as defined in claim 1.

8. A method of disinfecting or preserving an item comprising applying to or incorporating in said item an effective amount of a compound of claim 1.

* * * * *

UNITED STATES PATENT AND TRADEMARK OFFICE
CERTIFICATE OF CORRECTION

| | | |
|---|---|---|
| PATENT NO. | : 8,415,312 B2 | Page 1 of 1 |
| APPLICATION NO. | : 12/667434 | |
| DATED | : April 9, 2013 | |
| INVENTOR(S) | : Zotchev et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 215 days.

Signed and Sealed this
Eighth Day of October, 2013

Teresa Stanek Rea
*Deputy Director of the United States Patent and Trademark Office*